(12) United States Patent
Ellmark et al.

(10) Patent No.: US 10,577,425 B2
(45) Date of Patent: *Mar. 3, 2020

(54) ANTI-CD40 ANTIBODIES

(71) Applicant: ALLIGATOR BIOSCIENCE AB, Lund (SE)

(72) Inventors: Peter Ellmark, Lund (SE); Karin Enell Smith, Lund (SE); Niina Veitonmaki, Lund (SE)

(73) Assignee: ALLIGATOR BIOSCIENCE AB, Lund (SE)

( * ) Notice: Subject to any disclaimer, the term of this patent is extended or adjusted under 35 U.S.C. 154(b) by 435 days.

This patent is subject to a terminal disclaimer.

(21) Appl. No.: 15/103,156

(22) PCT Filed: Dec. 18, 2014

(86) PCT No.: PCT/EP2014/078555
§ 371 (c)(1),
(2) Date: Jun. 9, 2016

(87) PCT Pub. No.: WO2015/091853
PCT Pub. Date: Jun. 25, 2015

(65) Prior Publication Data
US 2016/0311916 A1 Oct. 27, 2016

(30) Foreign Application Priority Data
Dec. 19, 2013 (GB) .................................. 1322583.4

(51) Int. Cl.
*C07K 16/28* (2006.01)
*A61K 47/68* (2017.01)
*C07K 16/30* (2006.01)
*A61K 39/00* (2006.01)

(52) U.S. Cl.
CPC ...... *C07K 16/2878* (2013.01); *A61K 47/6849* (2017.08); *C07K 16/30* (2013.01); *C07K 16/303* (2013.01); *C07K 16/3015* (2013.01); *C07K 16/3023* (2013.01); *C07K 16/3038* (2013.01); *C07K 16/3069* (2013.01); *A61K 2039/505* (2013.01); *C07K 2317/21* (2013.01); *C07K 2317/33* (2013.01); *C07K 2317/565* (2013.01); *C07K 2317/622* (2013.01); *C07K 2317/73* (2013.01); *C07K 2317/732* (2013.01); *C07K 2317/75* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 2004/0120948 A1 | 6/2004 | Mikayama et al. | |
| 2010/0098694 A1* | 4/2010 | Bedian | C07K 16/2878 424/133.1 |
| 2011/0243932 A1* | 10/2011 | Barrett | A61K 9/0019 424/133.1 |
| 2017/0304437 A1* | 10/2017 | Ellmark | C07K 16/2878 |

FOREIGN PATENT DOCUMENTS

| | | |
|---|---|---|
| WO | 01/83755 A1 | 11/2001 |
| WO | 2014/207064 A1 | 12/2014 |

OTHER PUBLICATIONS

Rudikoff et al. Proc Natl Acad Sci USA 79:1979-1983 (1982). (Year: 1982).*
Colman, Research in Immunology 145: 33-36 (1994). (Year: 1994).*
Kussie et al., J. Immunol. 152: 146-152 (1994). (Year: 1994).*
Chen et al., EMBO J., 14: 2784-2794 (1995). (Year: 1995).*
Law, C.L., et al., "Preclinical Antilymphoma Activity of a Humanized Anti-CD40 Monoclonal Antibody, SGN-40" Cancer Res. (2005) 65(18):8331-8338.
Francisco, J.A., et al., "Agonistic Properties and in Vivo Antitumor Activity of the Anti-CD40 Antibody SGN-14" Cancer Res. (2000) 60:3225-3231.
White, A.L., et al., "Interaction with FcgRIIB Is Critical for the Agonistic Activity of Anti-CD40 Monoclonal Antibody" J. Immunol. (2011) 187:1754-1763.
Ellmark, P., et al., "Modulation of the CD40-CD40 ligand interaction using human anti-CD40 single-chain antibody fragments obtained from the n-CoDeR phage display library" Immunology (2002) 106:456-463.
Malmborg-Hager, A.G., et al., "Affinity and Epitope Profiling of Mouse Anti-CD40 Monoclonal Antibodies" Scandinavian J. Immunol. (2003) 57:517-524.
Neron, S., et al., "Tuning of CD40-CD154 Interactions in Human B-Lymphocyte Activation: A Broad Array of in Vitro Models for a Complex in Vivo Situation" Archivum Immunologiae et Therapiae Experimentalis (2011) 59:25-40.

* cited by examiner

*Primary Examiner* — Phillip Gambel
(74) *Attorney, Agent, or Firm* — Robert C. Netter, Jr.; Dann, Dorfman, Herrell & Skillman

(57) ABSTRACT

The invention provides an antibody or fragment thereof that specifically binds to human CD40.

8 Claims, 9 Drawing Sheets
Specification includes a Sequence Listing.

D

ANTI-CD40 ANTIBODIES

This application is a § 371 application of PCT/EP2014/078555, filed Dec. 18, 2014, which in turn claims priority to GB Application 1322583.4, filed Dec. 19, 2013. The entire disclosure of each of the foregoing applications is incorporated by reference herein.

FIELD OF THE INVENTION

The present invention relates to antibodies that specifically bind to CD40, and in particular to human CD40.

BACKGROUND TO THE INVENTION

Cancer is a leading cause of premature deaths in the developed world. The aim of immunotherapy in cancer is to mount an effective immune response by the body against a tumour. This may be achieved by, for example, breaking tolerance against tumour antigen, augmenting anti-tumor immune responses, and stimulating local cytokine responses at the tumor site. The key effector cell of a long lasting anti-tumor immune response is the activated tumor specific effector T cell. Incomplete activation of effector T cells by, for example, dendritic cells can cause T-cell anergy, which results in an inefficient anti-tumor response, whereas adequate induction by dendritic cells can generate a potent expansion of activated effector T cells, redirecting the immune response towards the tumor.

The cell surface CD40 receptor molecule is a member of the tumour necrosis factor receptor superfamily (TNFR) and is a key regulator in both innate and adaptive immune responses. It is expressed on human antigen presenting cells, in particular B cells, dendritic cells and macrophages, as well as on normal cells, such as fibroblasts, smooth muscle cells, endothelial cells and epithelial cells. Moreover, is it expressed on a wide range of tumor cells including all B-lymphomas, 30-70% of solid tumours, melanomas and carcinomas.

The natural ligand of CD40, designated CD154 or CD40L, is mainly expressed on mature T lymphocytes. CD40L-mediated signalling triggers several biological events, including immune cell activation, proliferation, and production of cytokines and chemokines. Thus, stimulation via the CD40 receptor enhances cellular and immune functions. Its role in cell-mediated immune responses is well known. For example, the activation of dendritic cells via CD40 stimulation, induces activation of effector T cells. Treatment with CD40 agonists may thus provide the means to redirect the immune response and expand effector T cells directed to tumour cells Antitumour effects have been reported for some anti-CD40 antibodies, with several mechanisms having been identified. An indirect effect is observed for CD40 negative tumors, involving the activation of antigen presenting cells, in particular increased activity by tumor specific cytotoxic T lymphocytes and natural killer cells (NK cells). A direct antitumor mechanism is observed for CD40 positive tumours, wherein the CD40 antibody binding to tumour cells induces cell apoptosis. These mechanisms for anti-tumour activity may be complemented by the stimulation of a humoral response leading to enhanced antibody mediated cellular cytotoxicity (ADCC). However, the systemic administration of anti-CD40 antibodies has also been associated with adverse side effects, such as shock syndrome and cytokine release syndrome.

Accordingly there remains a need for improved cancer therapies, in particular anti-CD40 antibodies suitable for use in therapy.

SUMMARY OF THE INVENTION

The present inventors have produced antibodies which are suitable for use in therapy. The antibodies of the present invention specifically bind to human CD40. The antibodies of the present invention typically bind to human CD40 when localised on the surface of a cell.

The invention provides a human antibody, or fragment thereof, specific for human CD40 that:
(a) specifically binds to human CD40 when localised on the surface of a cell; and/or
(b) enhances antibody dependent cellular cytotoxicity (ADCC)-mediated lysis of a cell expressing CD40; and/or
(c) enhances apoptosis of a cell expressing CD40; and/or
(d) modulates the activity of a cell expressing CD40, wherein said modulation is an increase or decrease in the activity of said cell; and/or
(e) blocks binding of CD40L to CD40, reduces binding of CD40L to CD40, or does not block or reduce binding of CD40L to CD40.

The antibody or fragment of the invention may comprise:
(a) a heavy chain CDR3 sequence which is 12 amino acids in length and which comprises the consensus sequence of A, R, G, P, F/V/A, Y, S, S/T, V/Y/F, F/I/L, D, Y a heavy chain CDR1 sequence which consists of the sequence GFTFSSYA, and a light chain CDR3 sequence which consists of the sequence QQSYSTPYT, which antibody or fragment does not block or reduce CD40L binding to CD40, and/or binds to module B of domain 3 of CD40; or
(b) a heavy chain CDR3 sequence which is 9 or 10 amino acids in length and which comprises the consensus sequence of A, R, A/Y/R, V, -/N, F, G, F/M/I, D, Y, which antibody or fragment reduces CD40L binding to CD40 and/or binds to to module B of domain 1 of CD40.

The antibody or fragment typically has at least one CDR sequence selected from:
(a) SEQ ID NOs 43, 44, 45, 46, 47 and 48 (CDRs of antibody 1140/1135); or
(b) SEQ ID NOs 13, 14, 15, 16, 17 and 18 (CDRs of antibody 1132/1133); or
(c) SEQ ID NOs 1, 2, 3, 4, 5 and 6 (CDRs of antibody 1146/1147); or
(d) SEQ ID NOs 7, 8, 9, 10, 11 and 12 (CDRs of antibody 1142/1135); or
(e) SEQ ID NOs 19, 20, 21, 22, 23 and 24 (CDRs of antibody 1148/1149); or
(f) SEQ ID NOs 25, 26, 27, 28, 29 and 30 (CDRs of antibody 1138/1135); or
(g) SEQ ID NOs 31, 32, 33, 34, 35 and 36 (CDRs of antibody 1134/1135); or
(h) SEQ ID NOs 37, 38, 39, 40, 41 and 42 (CDRs of antibody 1136/1137); or
(i) SEQ ID NOs 49, 50, 51, 52, 53 and 54 (CDRs of antibody 1150/1151); or
(j) SEQ ID NOs 55, 56, 57, 58, 59 and 60 (CDRs of antibody 1107/1108).

Accordingly the antibody or fragment thereof may comprises the CDRs of SEQ ID NOs 43, 44 and 45 and/or SEQ ID NOs 46, 47 and 48.

Alternatively the antibody or fragment thereof may comprise the CDRs of SEQ ID NOs 13, 14 and 15 and/or SEQ ID NOs 16, 17 and 18.

Alternatively the antibody or fragment thereof may comprise the CDRs of SEQ ID NOs 1, 2 and 3 and/or SEQ ID NOs 4, 5 and 6

Alternatively the antibody or fragment thereof may comprise the CDRs of SEQ ID NOs 7, 8 and 9 and/or SEQ ID NOs 10, 11 and 12.

Alternatively the antibody or fragment thereof may comprise the CDRs of SEQ ID NOs 19, 20 and 21 and/or SEQ ID NOs 22, 23 and 24.

Alternatively the antibody or fragment thereof may comprise the CDRs of SEQ ID NOs 25, 26 and 27 and/or SEQ ID NOs 28, 29 and 30.

Alternatively the antibody or fragment thereof may comprise the CDRs of SEQ ID NOs 31, 32 and 33 and/or SEQ ID NOs 34, 35 and 36.

Alternatively the antibody or fragment thereof may comprise the CDRs of SEQ ID NOs 37, 38 and 39 and/or SEQ ID NOs 40, 41 and 42.

Alternatively the antibody or fragment thereof may comprise the CDRs of SEQ ID NOs 49, 50 and 51 and/or SEQ ID NOs 52, 53 and 54.

Alternatively the antibody or fragment thereof may comprise the CDRs of SEQ ID NOs 55, 56 and 57 and/or SEQ ID NOs 58, 59 and 60.

An antibody of the invention preferably has an isoelectric point (pI) of 9.0 or above, preferably 9.2 or above, most preferably 9.25 or above.

The antibodies and fragments thereof can be used in the treatment of diseases and disorders, and in particular in the treatment of cancer.

BRIEF DESCRIPTION OF THE SEQUENCE LISTING

SEQ ID NOs 1 to 80 Provide the Following Amino Acid Sequences:
SEQ ID NO: 1, 2 and 3 are CDRs 1, 2 and 3 respectively of the heavy chain of the antibody 1146/1147.
SEQ ID NO: 4, 5 and 6 are the CDRs 1, 2 and 3 respectively of the light chain of the antibody 1146/1147.
SEQ ID NO: 7, 8 and 9 are CDRs 1, 2 and 3 respectively of the heavy chain of the antibody 1142/1135.
SEQ ID NO: 10, 11 and 12 are the CDRs 1, 2 and 3 respectively of the light chain of the antibody 1142/1135
SEQ ID NO: 13, 14 and 15 are CDRs 1, 2 and 3 respectively of the heavy chain of the antibody 1132/1133.
SEQ ID NO: 16, 17 and 18 are the CDRs 1, 2 and 3 respectively of the light chain of the antibody 1132/1133.
SEQ ID NO: 19, 20 and 21 are CDRs 1, 2 and 3 respectively of the heavy chain of the antibody 1148/1149.
SEQ ID NO: 22, 23 and 24 are the CDRs 1, 2 and 3 respectively of the light chain of the antibody 1148/1149.
SEQ ID NO: 25, 26 and 27 are CDRs 1, 2 and 3 respectively of the heavy chain of the antibody 1138/1135.
SEQ ID NO: 28, 29 and 30 are the CDRs 1, 2 and 3 respectively of the light chain of the antibody 1138/1135.
SEQ ID NO: 31, 32 and 33 are CDRs 1, 2 and 3 respectively of the heavy chain of the antibody 1134/1135.
SEQ ID NO: 34, 35 and 36 are the CDRs 1, 2 and 3 respectively of the light chain of the antibody 1134/1135.
SEQ ID NO: 37, 38 and 39 are CDRs 1, 2 and 3 respectively of the heavy chain of the antibody 1136/1137.
SEQ ID NO: 40, 41 and 42 are the CDRs 1, 2 and 3 respectively of the light chain of the antibody 1136/1137.
SEQ ID NO: 43, 44 and 45 are CDRs 1, 2 and 3 respectively of the heavy chain of the antibody 1140/1135.
SEQ ID NO: 46, 47 and 48 are the CDRs 1, 2 and 3 respectively of the light chain of the antibody 1140/1135.
SEQ ID NO: 49, 50 and 51 are CDRs 1, 2 and 3 respectively of the heavy chain of the antibody 1150/1151.
SEQ ID NO: 52, 53 and 54 are the CDRs 1, 2 and 3 respectively of the light chain of the antibody 1150/1151.
SEQ ID NO: 55, 56 and 57 are CDRs 1, 2 and 3 respectively of the heavy chain of the antibody 1107/1108.
SEQ ID NO: 58, 59 and 60 are the CDRs 1, 2 and 3 respectively of the light chain of the antibody 1107/1108.
SEQ ID NO: 61 is the variable region of the heavy chain of the antibody 1146/1147.
SEQ ID NO: 62 is the variable region of the light chain of the antibody 1146/1147.
SEQ ID NO: 63 is the variable region of the heavy chain of the antibody 1142/1135.
SEQ ID NO: 64 is the variable region of the light chain of the antibody 1142/1135.
SEQ ID NO: 65 is the variable region of the heavy chain of the antibody 1132/1133.
SEQ ID NO: 66 is the variable region of the light chain of the antibody 1132/1133.
SEQ ID NO: 67 is the variable region of the heavy chain of the antibody 1148/1149.
SEQ ID NO: 68 is the variable region of the light chain of the antibody 1148/1149.
SEQ ID NO: 69 is the variable region of the heavy chain of the antibody 1138/1135.
SEQ ID NO: 70 is the variable region of the light chain of the antibody 1138/1135.
SEQ ID NO: 71 is the variable region of the heavy chain of the antibody 1134/1135.
SEQ ID NO: 72 is the variable region of the light chain of the antibody 1134/1135.
SEQ ID NO: 73 is the variable region of the heavy chain of the antibody 1136/1137.
SEQ ID NO: 74 is the variable region of the light chain of the antibody 1136/1137.
SEQ ID NO: 75 is the variable region of the heavy chain of the antibody 1140/1135.
SEQ ID NO: 76 is the variable region of the light chain of the antibody 1140/1135.
SEQ ID NO: 77 is the variable region of the heavy chain of the antibody 1150/1151.
SEQ ID NO: 78 is the variable region of the light chain of the antibody 1150/1151.
SEQ ID NO: 79 is the variable region of the heavy chain of the antibody 1107/1108.
SEQ ID NO: 80 is the variable region of the light chain of the antibody 1107/1108.
SEQ ID NOs: 81 to 100 Provide the Following Nucleotide Sequences:
SEQ ID NO: 81 encodes the variable region of the heavy chain of antibody 1146/1147.
SEQ ID NO: 82 encodes the variable region of the light chain of antibody 1146/1147.
SEQ ID NO: 83 encodes the variable region of the heavy chain of antibody 1142/1135.
SEQ ID NO: 84 encodes the variable region of the light chain of antibody 1142/1135.
SEQ ID NO: 85 encodes the variable region of the heavy chain of antibody 1132/1133.
SEQ ID NO: 86 encodes the variable region of the light chain of antibody 1132/1133.
SEQ ID NO: 87 encodes the variable region of the heavy chain of antibody 1148/1149.

SEQ ID NO: 88 encodes the variable region of the light chain of antibody 1148/1149.
SEQ ID NO: 89 encodes the variable region of the heavy chain of antibody 1138/1135.
SEQ ID NO: 90 encodes the variable region of the light chain of antibody 1138/1135.
SEQ ID NO: 91 encodes the variable region of the heavy chain of antibody 1134/1135.
SEQ ID NO: 92 encodes the variable region of the light chain of antibody 1134/1135.
SEQ ID NO: 93 encodes the variable region of the heavy chain of antibody 1136/1137.
SEQ ID NO: 94 encodes the variable region of the light chain of antibody 1136/1137.
SEQ ID NO: 95 encodes the variable region of the heavy chain of antibody 1140/1135.
SEQ ID NO: 96 encodes the variable region of the light chain of antibody 1140/1135.
SEQ ID NO: 97 encodes the variable region of the heavy chain of antibody 1150/1151.
SEQ ID NO: 98 encodes the variable region of the light chain of antibody 1150/1151.
SEQ ID NO: 99 encodes the variable region of the heavy chain of antibody 1107/1108.
SEQ ID NO:100 encodes the variable region of the light chain of antibody 1107/1108.
SEQ ID NO: 101 is the amino acid sequence of an exemplary heavy chain constant region.
SEQ ID NO: 102 is the amino acid sequence of an exemplary heavy chain constant region.
SEQ ID NO: 103 is the amino acid sequence of an exemplary light chain constant region.
SEQ ID NO: 104 is the amino acid sequence of human CD40.
SEQ ID NO: 105 is the amino acid sequence of the monomeric extracellular domain of human wildtype CD86, excluding a 23 amino acid signal sequence from the N terminus.
SEQ ID NOs: 106 to 108 are exemplary variants of the amino acid sequence of SEQ ID NO: 105.

DETAILED DESCRIPTION OF THE INVENTION

Figure 1:
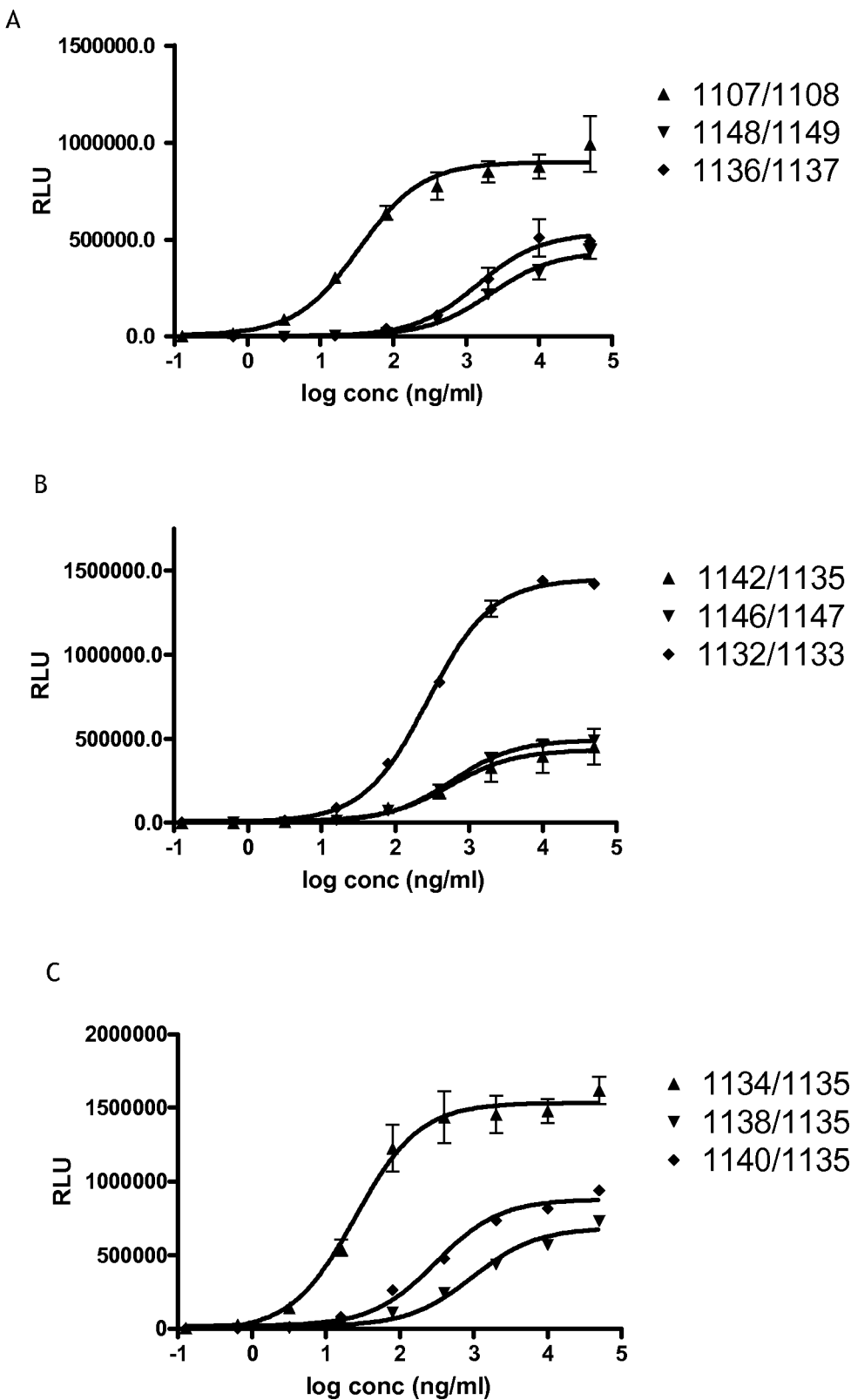
FIG. 1 shows the results of a CD40 binding ELISA for (A) antibodies 1107/1108, 1148/1149, 1136/1137; (B) antibodies 1142/1135, 1146/1147, 1132/1133; (C) antibodies 1134/1135, 1138/1135, 1140/1135; and (D) antibody 1150/1151.
Figure 1:
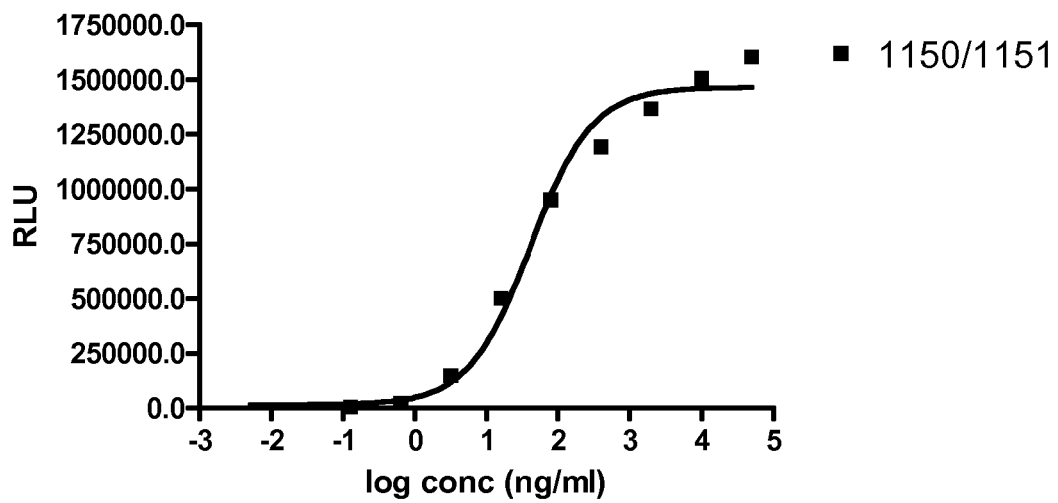

The present invention relates to antibodies that bind to CD40. The invention also relates to uses for such antibodies, such as therapeutic uses. The antibodies preferably specifically bind to CD40, that is they bind to CD40 but they do not bind, or bind at a lower affinity, to other molecules. The term CD40 as used herein refers to human CD40. The sequence of human CD40 is set out in SEQ ID NO: 104. An antibody of the present invention may have some binding affinity for CD40 from other mammals, for example primate or murine CD40. The antibodies preferably bind to human CD40 when localised on the surface of a cell.

An antibody of the invention has the ability to bind to CD40 in its native state and in particular to CD40 localised on the surface of a cell. Preferably, an antibody of the invention will bind specifically to CD40. That is, an antibody of the invention will preferably bind to CD40 with greater binding affinity than that at which it binds to another molecule.

By "localised on the surface of a cell" it is meant that CD40 is associated with the cell such that one or more region of CD40 is present on the outer face of the cell surface. For example, CD40 may be inserted into the cell plasma membrane (i.e. orientated as a transmembrane protein) with one or more regions presented on the extracellular surface. This may occur in the course of expression of CD40 by the cell. Thus, in one embodiment, "localised on the surface of a cell" may mean "expressed on the surface of a cell." Alternatively, CD40 may be outside the cell with covalent and/or ionic interactions localising it to a specific region or regions of the cell surface.

An antibody of the invention may enhance ADCC-mediated lysis of a cell expressing CD40 and/or enhance apoptosis of a cell expressing CD40. The cell is typically a tumour cell. By "enhance" it is meant that the number of cells lysed or apoptosed increases in the presence of an antibody of the invention, relative to the number of cells lysed or apoptosed in the presence of an appropriate control substance. Methods for determining the level of ADCC-mediated lysis or apoptosis in a sample of cells are well known in the art. For example, a chromium-51 release assay, europium release assay or sulphur-35 release assay may be used. In such assays, a previously labelled target cell line expressing the antigen (in this case CD40) is incubated with an antibody to be tested. After washing, effector cells (typically expressing Fc receptor CD16) are co-incubated with the antibody-labelled target cells. Target cell lysis is subsequently measured by release of intracellular label by a scintillation counter or spectrophotometry.

As an alternative to the labelling with radioisotopes required in such assays, methods may be used in which lysis is detected by measuring the release of enzymes naturally present in the target cells. This may be achieved by detection (for example bioluminescent detection) of the products of an enzyme-catalysed reaction. No previous labelling of the cells is required in such an assay. A typical cellular enzyme detected with such an assay is GAPDH.

An antibody of the invention may modulate the activity of a cell expressing CD40, wherein said modulation is an increase or decrease in the activity of said cell. The cell is typically a dendritic cell, a B cell, a macrophage, a monocyte, or any myeloid cell. The cell may be CD11b-positive or CD11c-positive.

Professional APCs, such as dendritic cells, are activated when signaling via CD40 occurs, which triggers several biological events, including immune cell activation, proliferation, and production of cytokines and chemokines. Methods for determining dendritic cell activation associated with CD40 are known in the art (discussed, for example, in Schonbeck et al., 2001, Cell Mol Life Sci., 58:40-43; van Kooten et al., 2000, J. Leuk., Biol., 67: 2-17) and are described further below, including in the Examples.

Stimulation of human B cells with recombinant CD40L or anti-CD40 antibodies induces up-regulation of surface markers, such as CD23, CD30, CD80, CD86, Fas and MHC II, secretion of soluble cytokines, e.g. IL-6, TNF-$\gamma$ and TNF-$\alpha$, and homeotypic aggregation. Methods for determining CD40-related B cell activation are known in the art (discussed, for example, in Schonbeck et al., 2001, supra) and are described further below, including in the Examples.

Methods and assays for determining the ability of an antibody to modulate the activity of dendritic cells and B cells are well known in the art. For example, the activation of dendritic cells may be assessed by measuring the level of cell surface markers such as CD86 and CD80 and/or by measuring anti-CD40 antibody-induced secretion of IFN-$\gamma$ from T cells, wherein in an increase in any of these parameters indicates increased activation and a decrease represents decreased activation. Similarly, the ability of an antibody to modulate the activity of B cells may be assessed by measuring the level of cell surface markers (such as CD86) and/or by measuring anti-CD40 antibody-induced B cell proliferation (see Example 3 below), wherein in an increase in any of these parameters indicates increased activation and a decrease represents decreased activation.

Preferably, an antibody of the invention which increases the activation of dendritic cells or B cells has a potency for dendritic cell or B cell activation (measured as an EC50, as described in Example 3) of 5 µg/ml or lower, 4 µg/ml or lower, 3 µg/ml or lower, 2.5 µg/ml or lower, 1.5 µg/ml or lower, 1.0 µg/ml or lower, 0.5 µg/ml or lower, 0.4 µg/ml or lower, 0.3 µg/ml or lower, or 0.2 µg/ml or lower. The EC50 will typically be higher than 0.1 µg/ml and thus the EC50 may be between 0.1 µg/ml and any of the upper limits specified in the preceding sentence.

The terms "binding activity" and "binding affinity" are intended to refer to the tendency of an antibody molecule to bind or not to bind to a target. Binding affinity may be quantified by determining the dissociation constant (Kd) for an antibody and its target. Similarly, the specificity of binding of an antibody to its target may be defined in terms of the comparative dissociation constants (Kd) of the antibody for its target as compared to the dissociation constant with respect to the antibody and another, non-target molecule.

Typically, the Kd for the antibody with respect to the target will be 2-fold, preferably 5-fold, more preferably 10-fold less than Kd with respect to the other, non-target molecule such as unrelated material or accompanying material in the environment. More preferably, the Kd will be 50-fold less, even more preferably 100-fold less, and yet more preferably 200-fold less.

The value of this dissociation constant can be determined directly by well-known methods, and can be computed even for complex mixtures by methods such as those, for example, set forth in Caceci et al. (Byte 9:340-362, 1984). For example, the Kd may be established using a double-filter nitrocellulose filter binding assay such as that disclosed by Wong & Lohman (Proc. Natl. Acad. Sci. USA 90, 5428-5432, 1993).

A preferred method for the evaluation of binding affinity for CD40 is by ELISA. Preferably, an antibody of the invention has an affinity for CD40 (measured as an EC50, as described in Example 3) of 2500 ng/ml or lower, 1500 ng/ml or lower, 1000 ng/ml or lower, 600 ng/ml or lower, 350 ng/ml or lower, 50 ng/ml or lower, 40 ng/ml or lower, 30 ng/ml or lower, 20 ng/ml or lower, or 10 ng/ml or lower. The EC50 will typically be higher than 1 ng/ml and thus the EC50 may be between 1 ng/ml and any of the upper limits specified in the preceding sentence. Other standard assays to evaluate the binding ability of ligands such as antibodies towards targets are known in the art, including for example, Western blots, RIAs, and flow cytometry analysis. The binding kinetics (e.g., binding affinity) of the antibody also can be assessed by standard assays known in the art, such as by surface plasmon resonance (e.g. Biacore™ system) analysis. This form of analysis is also described in the Examples. The affinity constant (KD) for binding to CD40 for an antibody of the invention is preferably in the range 1-10 nM. The association rate (ka) is preferably in the range 0.4-3.4×10$^6$ 1/M. The dissociation rate (kd) is preferably in the range the range 1-10×10$^{-3}$ 1/s. These values may typically be determined by surface plamson resonance.

A competitive binding assay can be conducted in which the binding of the antibody to the target is compared to the binding of the target by another, known ligand of that target, such as another antibody. The concentration at which 50% inhibition occurs is known as the Ki. Under ideal conditions, the Ki is equivalent to Kd. The Ki value will never be less than the Kd, so measurement of Ki can conveniently be substituted to provide an upper limit for Kd.

An antibody of the invention is preferably capable of binding to its target with an affinity that is at least two-fold, 10-fold, 50-fold, 100-fold or greater than its affinity for binding to another non-target molecule.

An antibody of the invention will typically have the ability to:

(a) specifically bind to human CD40 when localised on the surface of a cell; and/or
(b) enhance antibody dependent cellular cytotoxicity (ADCC)-mediated lysis of a cell expressing CD40; and/or
(c) enhance apoptosis of a cell expressing CD40; and/or
(d) modulate the activity of a cell expressing CD40, wherein said modulation is an increase or decrease in the activity of said cell; and/or
(e) blocks binding of CD40L to CD40, reduces binding of CD40L to CD40, or does not block or reduce binding of CD40L to CD40.

These characteristics may be assessed by any suitable method, such as the methods described herein including in the Examples.

An antibody of the invention typically binds to the same epitope as the antibody having the sequences of SEQ ID NOs: 61 and 62; or of SEQ ID NOs: 63 and 64; or of SEQ ID NOs: 65 and 66; or of SEQ ID NOs: 67 and 68; or of SEQ ID NOs: 69 and 70; or of SEQ ID NOs: 71 and 72; or of SEQ ID NOs: 73 and 74; or of SEQ ID NOs: 75 and 76; or of SEQ ID NOs: 77 and 78; or of SEQ ID NOs: 79 and 80. As used herein, the term "epitope" generally refers to the site on a target antigen which is recognised by an immune receptor such as an antibody. Preferably it is a short peptide derived from or as part of a protein. However the term is also intended to include peptides with glycopeptides and carbohydrate epitopes. A single antigenic molecule, such as a target protein as described herein, may comprise several different epitopes. Epitopes can be identified from knowledge of the amino acid and corresponding DNA sequences of the peptide, as well as from the nature of particular amino acids (e.g., size, charge, etc.) and the codon dictionary, without undue experimentation. See, e.g., Ivan Roitt, Essential Immunology, 1988; Janis Kuby, Immunology, 1992 e.g., pp. 79-81.

The location of an epitope may be identified by routine methods. For example, the general location of an epitope may be determined by assessing the ability of an antibody to bind to different fragments or variant CD40 polypeptides. The specific amino acids within CD40 that make contact with an antibody may also be determined using routine methods, such as that described in the Examples. For example, the antibody and target molecule may be combined and the antibody/target complex may be crystallised. The crystal structure of the complex may be determined and used to identify specific sites of interaction between the antibody and its target.

An antibody of the invention may bind to the same epitope or region as another antibody of the invention. For example, where an antibody of the invention is known, other antibodies of the invention may be identified by comparing their binding to CD40 with that of the known antibody.

An antibody of the invention may be an antibody that binds to the same epitope in CD40 as the antibodies described herein having the sequences of SEQ ID NOs: 61 and 62; or of SEQ ID NOs: 63 and 64; or of SEQ ID NOs: 65 and 66; or of SEQ ID NOs: 67 and 68; or of SEQ ID NOs: 69 and 70; or of SEQ ID NOs: 71 and 72; or of SEQ ID NOs: 73 and 74; or of SEQ ID NOs: 75 and 76; or of SEQ ID NOs: 77 and 78; or of SEQ ID NOs: 79 and 80. The antibody of the invention may comprise a heavy chain and/or a light chain.

An antibody of the invention may have the ability to cross-compete with another antibody of the invention for binding to CD40 or another appropriate target as described herein. For example, an antibody of the invention may cross-compete with one or more of the antibodies described herein, for example an antibody having the sequences of SEQ ID NOs: 61 and 62, for binding to CD40 or to a suitable fragment or variant of CD40 that is bound by the antibodies. Such cross-competing antibodies can be identified based on their ability to cross-compete with a known antibody of the invention in standard binding assays. For example, BIAcore™ analysis, ELISA assays or flow cytometry may be used to demonstrate cross-competition. Such cross-competition may suggest that the two antibodies bind to the same or similar epitopes.

An antibody of the invention may therefore be identified by a method that comprises a binding assay which assesses whether or not a test antibody is able to cross-compete with a known antibody of the invention for a binding site on the target molecule. Methods for carrying out competitive binding assays are well known in the art. For example they may involve contacting together a known antibody of the invention and a target molecule under conditions under which the antibody can bind to the target molecule. The antibody/target complex may then be contacted with a test antibody and the extent to which the test antibody is able to displace the antibody of the invention from antibody/target complexes may be assessed. An alternative method may involve contacting a test antibody with a target molecule under conditions that allow for antibody binding, then adding an antibody of the invention that is capable of binding that target molecule and assessing the extent to which the antibody of the invention is able to displace the test antibody from antibody/target complexes.

The ability of a test antibody to inhibit the binding of an antibody of the invention to the target demonstrates that the test compound can compete with an antibody of the invention for binding to the target and thus that the test antibody binds to the same epitope or region on the CD40 protein as the known antibody of the invention. A test antibody that is identified as cross-competing with a known antibody of the invention in such a method is also a potential antibody according to the present invention. The fact that the test antibody can bind CD40 in the same region as a known antibody of the invention and cross-compete with the known antibody of the invention suggests that the test antibody may act as a ligand at the same binding site as the known antibody and that the test antibody may therefore mimic the action of the known antibody.

The known antibody of the invention may be an antibody as described herein, such as one of the CD40 antibodies as described herein or any variant or fragment thereof as described herein that retains the ability to bind to CD40. An antibody of the invention may bind to the same epitope as one or more of the antibodies as described herein or any variant or fragment thereof as described herein that retains the ability to bind to CD40.

Specific binding may be assessed with reference to binding of the antibody to a molecule that is not the target. This comparison may be made by comparing the ability of an antibody to bind to the target and to another molecule. This comparison may be made as described above in an assessment of Kd or Ki. The other molecule used in such a comparison may be any molecule that is not the target molecule. Preferably the other molecule is not identical to the target molecule. Preferably the target molecule is not a fragment of the target molecule.

The term "antibody" as referred to herein includes whole antibodies and any antigen binding fragment (i.e., "antigen-binding portion") or single chains thereof. An antibody refers to a glycoprotein comprising at least two heavy (H) chains and two light (L) chains inter-connected by disulfide bonds, or an antigen binding portion thereof. Each heavy chain is comprised of a heavy chain variable region (abbreviated herein as VH) and a heavy chain constant region. Each light chain is comprised of a light chain variable region (abbreviated herein as VL) and a light chain constant region. The variable regions of the heavy and light chains contain a binding domain that interacts with an antigen. The VH and VL regions can be further subdivided into regions of hypervariability, termed complementarity determining regions (CDR), interspersed with regions that are more conserved, termed framework regions (FR). The constant regions of the antibodies may mediate the binding of the immunoglobulin to host tissues or factors, including various cells of the immune system (e.g., effector cells) and the first component (Clq) of the classical complement system.

An antibody of the invention may be a monoclonal antibody or a polyclonal antibody. In one embodiment, an antibody of the invention is a monoclonal antibody. Polyclonal antibodies are antibodies that are derived from different B cell lines. A polyclonal antibody may comprise a mixture of different immunoglobulin molecules that are directed against a specific antigen. The polyclonal antibody may comprise a mixture of different immunoglobulin molecules that bind to one or more different epitopes within an antigen molecule. Polyclonal antibodies may be produced by routine methods such as immunisation with the antigen of interest. For example a mouse capable of expressing human antibody sequences may be immunised with human CD40. Blood may be subsequently removed and the Ig fraction purified.

Monoclonal antibodies are immunoglobulin molecules that are identical to each other and have a single binding specificity and affinity for a particular epitope. Monoclonal antibodies (mAbs) of the present invention can be produced by a variety of techniques, including conventional monoclonal antibody methodology, for example those disclosed in "Monoclonal Antibodies; A manual of techniques", H Zola (CRC Press, 1988) and in "Monoclonal Hybridoma Antibodies: Techniques and Application", SGR Hurrell (CRC Press, 1982).

The term "antigen-binding portion" of an antibody refers to one or more fragments of an antibody that retain the ability to specifically bind to an antigen, such as CD40. It has been shown that the antigen-binding function of an antibody can be performed by fragments of a full-length antibody. Examples of binding fragments encompassed within the term "antigen-binding portion" of an antibody include a Fab fragment, a F(ab')$_2$ fragment, a Fab' fragment, a Fd fragment, a Fv fragment, a dAb fragment and an isolated complementarity determining region (CDR). Single chain antibodies such as scFv and heavy chain antibodies such as VHH and camel antibodies are also intended to be encompassed within the term "antigen-binding portion" of an antibody. These antibody fragments may be obtained using conventional techniques known to those of skill in the art, and the fragments may be screened for utility in the same manner as intact antibodies.

An antibody of the invention may be prepared, expressed, created or isolated by recombinant means, such as (a) antibodies isolated from an animal (e.g., a mouse) that is transgenic or transchromosomal for the immunoglobulin genes of interest or a hybridoma prepared therefrom, (b) antibodies isolated from a host cell transformed to express the antibody of interest, e.g., from a transfectoma, (c) antibodies isolated from a recombinant, combinatorial antibody library, and (d) antibodies prepared, expressed, created or isolated by any other means that involve splicing of immunoglobulin gene sequences to other DNA sequences.

An antibody of the invention may be a human antibody. The term "human antibody", as used herein, is intended to include antibodies having variable regions in which both the framework and CDR regions are derived from human germline immunoglobulin sequences. Furthermore, if the antibody contains a constant region, the constant region also is derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

Such a human antibody may be a human monoclonal antibody. Such a human monoclonal antibody may be produced by a hybridoma which includes a B cell obtained from a transgenic nonhuman animal, e.g., a transgenic mouse, having a genome comprising a human heavy chain transgene and a light chain transgene fused to an immortalized cell.

Human antibodies may be prepared by in vitro immunisation of human lymphocytes followed by transformation of the lymphocytes with Epstein-Barr virus.

The term "human antibody derivatives" refers to any modified form of the human antibody, e.g., a conjugate of the antibody and another agent or antibody.

Antibodies of the invention can be tested for binding to the target protein by, for example, standard ELISA or Western blotting. An ELISA assay can also be used to screen for hybridomas that show positive reactivity with the target protein. The binding specificity of an antibody may also be determined by monitoring binding of the antibody to cells expressing the target protein, for example by flow cytometry.

The specificity of an antibody of the invention for target protein may be further studied by determining whether or not the antibody binds to other proteins. For example, where it is desired to produce an antibody that specifically binds CD40 or a particular part, e.g. epitope, of CD40, the specificity of the antibody may be assessed by determining whether or not the antibody also binds to other molecules or modified forms of CD40 that lack the part of interest.

Once a suitable antibody has been identified and selected, the amino acid sequence of the antibody may be identified by methods known in the art. The genes encoding the antibody can be cloned using degenerate primers. The antibody may be recombinantly produced by routine methods.

A "polypeptide" is used herein in its broadest sense to refer to a compound of two or more subunit amino acids, amino acid analogs, or other peptidomimetics. The term "polypeptide" thus includes short peptide sequences and also longer polypeptides and proteins. As used herein, the term "amino acid" refers to either natural and/or unnatural or synthetic amino acids, including glycine and both the D or L optical isomers, and amino acid analogs and peptidomimetics.

The present inventors have identified antibodies as described in the examples. The present invention encompasses these antibodies and variants and fragments thereof which retain one or more activities of these antibodies. The activities of these antibodies include the ability to bind to CD40, and the ability to bind to human CD40 when expressed on the surface of a cell.

A suitable fragment or variant of this antibody will retain the ability to bind to CD40. It will preferably retain the ability to specifically bind to CD40. It will preferably retain the ability to specifically bind to the same epitope or region of the CD40 molecule as the antibody, for example an antibody having the sequence of SEQ ID NOs: 61 and 62, from which it is derived. It will also retain one or more additional functions of the antibody from which it is derived, such as the ability to:

(a) specifically bind to human CD40 when localised on the surface of a cell; and/or
(b) enhance antibody dependent cellular cytotoxicity (ADCC)-mediated lysis of a cell expressing CD40; and/or
(c) enhance apoptosis of a cell expressing CD40; and/or
(d) modulate the activity of a cell expressing CD40, wherein said modulation is an increase or decrease in the activity of said cell; and/or
(e) block binding of CD40L to CD40, reduce binding of CD40L to CD40, or not block or reduce binding of CD40L to CD40.

Polypeptide or antibody "fragments" according to the invention may be made by truncation, e.g. by removal of one or more amino acids from the N and/or C-terminal ends of a polypeptide. Up to 10, up to 20, up to 30, up to 40 or more amino acids may be removed from the N and/or C terminal in this way. Fragments may also be generated by one or more internal deletions.

An antibody of the invention may be, or may comprise, a fragment of the antibodies or a variant thereof. The antibody of the invention may be or may comprise an antigen binding portion of these antibodies or a variant thereof as discussed further above. For example, the antibody of the invention may be a Fab fragment of one of these antibodies or a variant thereof or may be a single chain antibody derived from one of these antibodies or a variant thereof.

The amino acid sequences of the variable regions of the heavy and light chain chains of a particular antibody of the invention are given in SEQ ID NOs: 61 and 62. The CDRs for the VH chain are shown in SEQ ID NOs: 1, 2 and 3. The CDRs for the VL chain are shown in SEQ ID NOs: 4, 5 and 6.

The amino acid sequences of the variable regions of the heavy and light chain chains of another antibody of the invention are given in SEQ ID NOs: 63 and 64. The CDRs for the VH chain are shown in SEQ ID NOs: 7, 8 and 9. The CDRs for the VL chain are shown in SEQ ID NOs: 10, 11 and 12.

The amino acid sequences of the variable regions of the heavy and light chain chains of another antibody of the invention are given in SEQ ID NOs: 65 and 66. The CDRs for the VH chain are shown in SEQ ID NOs: 13, 14 and 15. The CDRs for the VL chain are shown in SEQ ID NOs: 16, 17 and 18.

The amino acid sequences of the variable regions of the heavy and light chain chains of another antibody of the invention are given in SEQ ID NOs: 67 and 68. The CDRs for the VH chain are shown in SEQ ID NOs: 19, 20 and 21. The CDRs for the VL chain are shown in SEQ ID NOs: 22, 23 and 24.

The amino acid sequences of the variable regions of the heavy and light chain chains of another antibody of the invention are given in SEQ ID NOs: 69 and 70. The CDRs for the VH chain are shown in SEQ ID NOs: 25, 26 and 27. The CDRs for the VL chain are shown in SEQ ID NOs: 28, 29 and 30.

The amino acid sequences of the variable regions of the heavy and light chain chains of another antibody of the invention are given in SEQ ID NOs: 71 and 72. The CDRs for the VH chain are shown in SEQ ID NOs: 31, 32 and 33. The CDRs for the VL chain are shown in SEQ ID NOs: 34, 35 and 36.

The amino acid sequences of the variable regions of the heavy and light chain chains of another antibody of the invention are given in SEQ ID NOs: 73 and 74. The CDRs for the VH chain are shown in SEQ ID NOs: 37, 38 and 39. The CDRs for the VL chain are shown in SEQ ID NOs: 40, 41 and 42.

The amino acid sequences of the variable regions of the heavy and light chain chains of another antibody of the invention are given in SEQ ID NOs: 75 and 76. The CDRs for the VH chain are shown in SEQ ID NOs: 43, 44 and 45. The CDRs for the VL chain are shown in SEQ ID NOs: 46, 47 and 48.

The amino acid sequences of the variable regions of the heavy and light chain chains of another antibody of the invention are given in SEQ ID NOs: 77 and 78. The CDRs for the VH chain are shown in SEQ ID NOs: 49, 50 and 51. The CDRs for the VL chain are shown in SEQ ID NOs: 52, 53 and 54.

The amino acid sequences of the variable regions of the heavy and light chain chains of another antibody of the invention are given in SEQ ID NOs: 79 and 80. The CDRs for the VH chain are shown in SEQ ID NOs: 55, 56 and 57. The CDRs for the VL chain are shown in SEQ ID NOs: 58, 59 and 60.

An antibody of the invention may comprise the VH amino acid sequence of SEQ ID NO: 61, 63, 65, 67, 69, 71, 73, 75, 77 or 79, or a fragment or variant of any thereof. An antibody of the invention may comprise the VL amino acid sequence of SEQ ID NO: 62, 64, 66, 68, 70, 72, 74, 76, 78 or 80. or a fragment or variant of any thereof.

An antibody of the invention may comprise both (a) the VH amino acid sequence of SEQ ID NO: 61, or a fragment or variant thereof and (b) the VL amino acid sequence of SEQ ID NO: 62, or a fragment or variant thereof.

Alternatively an antibody of the invention may comprise both (a) the VH amino acid sequence of SEQ ID NO: 63, or a fragment or variant thereof and (b) the VL amino acid sequence of SEQ ID NO: 64, or a fragment or variant thereof.

Alternatively an of the invention may comprise both (a) the VH amino acid sequence of SEQ ID NO: 65, or a fragment or variant thereof and (b) the VL amino acid sequence of SEQ ID NO: 66, or a fragment or variant thereof.

Alternatively an of the invention may comprise both (a) the VH amino acid sequence of SEQ ID NO: 67, or a fragment or variant thereof and (b) the VL amino acid sequence of SEQ ID NO: 68, or a fragment or variant thereof.

Alternatively an of the invention may comprise both (a) the VH amino acid sequence of SEQ ID NO: 69, or a fragment or variant thereof and (b) the VL amino acid sequence of SEQ ID NO: 70, or a fragment or variant thereof.

Alternatively an of the invention may comprise both (a) the VH amino acid sequence of SEQ ID NO: 71, or a fragment or variant thereof and (b) the VL amino acid sequence of SEQ ID NO: 72, or a fragment or variant thereof.

Alternatively an of the invention may comprise both (a) the VH amino acid sequence of SEQ ID NO: 73, or a fragment or variant thereof and (b) the VL amino acid sequence of SEQ ID NO: 74, or a fragment or variant thereof.

Alternatively an of the invention may comprise both (a) the VH amino acid sequence of SEQ ID NO: 75, or a fragment or variant thereof and (b) the VL amino acid sequence of SEQ ID NO: 76, or a fragment or variant thereof.

Alternatively an of the invention may comprise both (a) the VH amino acid sequence of SEQ ID NO: 77, or a fragment or variant thereof and (b) the VL amino acid sequence of SEQ ID NO: 78, or a fragment or variant thereof.

Alternatively an of the invention may comprise both (a) the VH amino acid sequence of SEQ ID NO: 79, or a fragment or variant thereof and (b) the VL amino acid sequence of SEQ ID NO: 80, or a fragment or variant thereof.

An antibody of the invention may comprise a fragment of one of the VL or VH amino acid sequences shown above. For example, an antibody of the invention may comprise a fragment of at least 7, at least 8, at least 9, at least 10, at least 12, at least 15, at least 18, at least 20 or at least 25 consecutive amino acids from said VL or VH amino acid sequence. Such a fragment will preferably retain one or more of the functions discussed above, such as the ability to bind to CD40.

The SEQ ID NO identifiers for the sequences of the specific antibodies identified herein are summarised Table 1.

TABLE 1

| Antibody | CDR1 | CDR2 | CDR3 | Variable region (protein) | Variable region (nucleotide) |
|---|---|---|---|---|---|
| HEAVY CHAIN | | | | | |
| 1146/1147 | 1 | 2 | 3 | 61 | 81 |
| 1142/1135 | 7 | 8 | 9 | 63 | 83 |
| 1132/1133 | 13 | 14 | 15 | 65 | 85 |
| 1148/1149 | 19 | 20 | 21 | 67 | 87 |
| 1138/1135 | 25 | 26 | 27 | 69 | 89 |
| 1134/1135 | 31 | 32 | 33 | 71 | 91 |
| 1136/1137 | 37 | 38 | 39 | 73 | 93 |
| 1140/1135 | 43 | 44 | 45 | 75 | 95 |
| 1150/1151 | 49 | 50 | 51 | 77 | 97 |
| 1107/1108 | 55 | 56 | 57 | 79 | 99 |
| LIGHT CHAIN | | | | | |
| 1146/1147 | 4 | 5 | 6 | 62 | 82 |
| 1142/1135 | 10 | 11 | 12 | 64 | 84 |
| 1132/1133 | 16 | 17 | 18 | 66 | 86 |
| 1148/1149 | 22 | 23 | 24 | 68 | 88 |
| 1138/1135 | 28 | 29 | 30 | 70 | 90 |
| 1134/1135 | 34 | 35 | 36 | 72 | 92 |
| 1136/1137 | 40 | 41 | 42 | 74 | 94 |
| 1140/1135 | 46 | 47 | 48 | 76 | 96 |
| 1150/1151 | 52 | 53 | 54 | 78 | 98 |
| 1107/1108 | 58 | 59 | 60 | 80 | 100 |

An antibody of the invention may comprise one, two, three, four, five or six CDR sequences from any one of the specific antibodies identified herein, for example any one of antibodies 1146/1147, 1142/1135, 1132/1133, 1148/1149, 1138/1135, 1134/1135, 1136/1137, 1140/1135, 1150/1151 and 1107/1108 as listed in Table 1. Such an antibody will preferably have one or more of the functions described herein. For example, the antibody may:

(a) specifically bind to human CD40 when localised on the surface of a cell; and/or
(b) enhance antibody dependent cellular cytotoxicity (ADCC)-mediated lysis of a cell expressing CD40; and/or
(c) enhance apoptosis of a cell expressing CD40; and/or
(d) modulate the activity of a cell expressing CD40, wherein said modulation is an increase or decrease in the activity of said cell; and/or
(e) block binding of CD40L to CD40, reduce binding of CD40L to CD40, or does not block or reduce binding of CD40L to CD40.

An antibody of the invention may comprise one or more of the CDR sequences of any one of the specific antibodies as shown in Table 1. An antibody of the invention may comprise one or more heavy chain CDR sequences and alternatively or additionally one or more light chain CDR sequences of said specific antibody. An antibody of the invention may comprise one, two or all three of the heavy chain CDR sequences of a specific antibody as shown in Table 1 and alternatively or additionally one, two or all three of the light chain CDR sequences of said specific antibody. An antibody of the invention may comprises all six CDR sequences of a specific antibody as shown in Table 1. By way of example, where the specific antibody of Table 1 is the antibody 1146/1147, an antibody of the invention may comprise one or more of SEQ ID NOs: 1, 2, 3, 4, 5 and 6. An antibody of the invention may comprise one, two or all three of SEQ ID NOs: 1, 2 and 3 and/or one, two or all three of SEQ ID NOs: 4, 5 and 6. An antibody of the invention may comprise all six of SEQ ID NOs: 1 to 6.

An antibody of the invention may alternatively be or may comprise a variant of one of these specific sequences. For example, a variant may be a substitution, deletion or addition variant of any of the above amino acid sequences.

A variant antibody may comprise 1, 2, 3, 4, 5, up to 10, up to 20, up to 30 or more amino acid substitutions and/or deletions from the specific sequences and fragments discussed above. "Deletion" variants may comprise the deletion of individual amino acids, deletion of small groups of amino acids such as 2, 3, 4 or 5 amino acids, or deletion of larger amino acid regions, such as the deletion of specific amino acid domains or other features. "Substitution" variants preferably involve the replacement of one or more amino acids with the same number of amino acids and making conservative amino acid substitutions. For example, an amino acid may be substituted with an alternative amino acid having similar properties, for example, another basic amino acid, another acidic amino acid, another neutral amino acid, another charged amino acid, another hydrophilic amino acid, another hydrophobic amino acid, another polar amino acid, another aromatic amino acid or another aliphatic amino acid. Some properties of the 20 main amino acids which can be used to select suitable substituents are as follows:

| | | | |
|---|---|---|---|
| Ala | aliphatic, hydrophobic, neutral | Met | hydrophobic, neutral |
| Cys | polar, hydrophobic, neutral | Asn | polar, hydrophilic, neutral |
| Asp | polar, hydrophilic, charged (−) | Pro | hydrophobic, neutral |
| Glu | polar, hydrophilic, charged (−) | Gln | polar, hydrophilic, neutral |
| Phe | aromatic, hydrophobic, neutral | Arg | polar, hydrophilic, charged (+) |
| Gly | aliphatic, neutral | Ser | polar, hydrophilic, neutral |
| His | aromatic, polar, hydrophilic, charged (+) | Thr | polar, hydrophilic, neutral |
| Ile | aliphatic, hydrophobic, neutral | Val | aliphatic, hydrophobic, neutral |
| Lys | polar, hydrophilic, charged(+) | Trp | aromatic, hydrophobic, neutral |
| Leu | aliphatic, hydrophobic, neutral | Tyr | aromatic, polar, hydrophobic |

Preferred "derivatives" or "variants" include those in which instead of the naturally occurring amino acid the amino acid which appears in the sequence is a structural analog thereof. Amino acids used in the sequences may also be derivatized or modified, e.g. labelled, providing the function of the antibody is not significantly adversely affected.

Derivatives and variants as described above may be prepared during synthesis of the antibody or by post-production modification, or when the antibody is in recombinant form using the known techniques of site-directed mutagenesis, random mutagenesis, or enzymatic cleavage and/or ligation of nucleic acids.

Preferably variant antibodies according to the invention have an amino acid sequence which has more than 60%, or more than 70%, e.g. 75 or 80%, preferably more than 85%, e.g. more than 90 or 95% amino acid identity to the VL or VH domain, or a fragment thereof, of an antibody disclosed herein. This level of amino acid identity may be seen across the full length of the relevant SEQ ID NO sequence or over a part of the sequence, such as across 20, 30, 50, 75, 100, 150, 200 or more amino acids, depending on the size of the full length polypeptide.

In connection with amino acid sequences, "sequence identity" refers to sequences which have the stated value when assessed using ClustalW (Thompson et al., 1994, supra) with the following parameters:

Pairwise alignment parameters—Method: accurate, Matrix: PAM, Gap open penalty: 10.00, Gap extension penalty: 0.10;

Multiple alignment parameters—Matrix: PAM, Gap open penalty: 10.00, % identity for delay: 30, Penalize end gaps: on, Gap separation distance: 0, Negative matrix: no, Gap extension penalty: 0.20, Residue-specific gap penalties: on, Hydrophilic gap penalties: on, Hydrophilic residues: G, P, S, N, D, Q, E, K, and R. Sequence identity at a particular residue is intended to include identical residues which have simply been derivatized.

The present invention thus provides antibodies having specific VH and VL amino acid sequences and variants and fragments thereof which maintain the function or activity of these VH and VL domains.

Accordingly, an antibody of the invention may comprise:

(a) a heavy chain variable region amino acid sequence of SEQ ID NO: SEQ ID NO: 61, 63, 65, 67, 69, 71, 73, 75, 77 or 79;

(b) a fragment of at least 7 amino acids of (a), wherein the antibody retains the ability to specifically bind to CD40; or (c) a variant of (a) having at least 70% amino acid sequence identity to a sequence of (a), wherein the antibody retains the ability to specifically bind to CD40.

An antibody of the invention may comprise:

(a) a light chain variable region amino acid sequence of SEQ ID NO: 62, 64, 66, 68, 70, 72, 74, 76, 78 or 80;

(b) a fragment of at least 7 amino acids of (a), wherein the antibody retains the ability to specifically bind to CD40; or (c) a variant of (a) having at least 70% amino acid sequence identity to a sequence of (a), wherein the antibody retains the ability to specifically bind to CD40.

An antibody of the invention may comprise:

(a) the heavy chain variable region and the light chain variable region of a specific antibody as disclosed in Table 1;

(b) a variant of (a) in which one or both of the heavy chain and light chain sequences is modified such that it comprises a fragment of at least 7 amino acids of the sequence specified in (a); or (c) a variant of (a) or (b) in which one or both of the heavy and light chain sequences is modified such that it has at least 70% amino acid sequence identity to a sequence of (a) or (b);

wherein the antibody retains the ability to specifically bind to CD40.

By way of example, where the specific antibody of Table 1 is the antibody designated 1146/1147, an antibody of the invention may comprise:

(a) the heavy chain variable region of SEQ ID NO: 61 and the light chain variable region of SEQ ID NO: 62;

(b) a variant of (a) in which one or both of the heavy chain and light chain sequences is modified such that it comprises a fragment of at least 7 amino acids of the sequence specified in (a); or (c) a variant of (a) or (b) in which one or both of the heavy and light chain sequences is modified such that it has at least 70% amino acid sequence identity to a sequence of (a) or (b);

wherein the antibody retains the ability to specifically bind to CD40.

As explained above, an antibody of the invention may bind to the same epitope or region as another antibody of the invention. Thus it will be seen that such an antibody may bind to the same epitope or region of CD40 as any of the specific antibodies, fragments and variants described herein.

It is preferred that a high proportion of the antibody or fragment of the invention will be retained within a tumour microenvironment in vivo for an extended period of time following local administration of said antibody or fragment to a tumour site. That is, it is preferred that the antibody or fragment exhibit reduced leakage from the tumour site into vascular or lymphatic circulation. Preferably at least 30% of an antibody dose administered to a tumour site is retained in the tumour site at four hours after administration, more preferably at least 40% of the dose is retained at four hours after administration and most preferably at least 50% of the dose is retained at four hours after administration. Antibody retention in a tumour micoenvironment can be studied by injecting the antibody into tumours in murine models and measuring the serum levels of the antibody over time after administration. Alternatively the distribution of the antibody can be measured using radiolabeled antibodies injected into tumors in murine models.

The pH in a tumour microenvironment in vivo is significantly more acidic than that of healthy tissues. Ranges for tumours are reported as around pH 6.5 to 7.2 or 6.6 to 7.0, as compared to 7.2 to 7.4 for healthy tissues. This acidity is primarily due to anaerobic glycolysis in tumor regions subjected to short-term or long-term hypoxia as a result of poorly organized vasculature with diminished chaotic blood flow, and aerobic glycolysis (the Warburg effect), a common cancer phenotypic property in which the glycolytic metabolic pathways are used even in the presence of oxygen. Given this acidity, it is preferred that the antibody of the invention has a high isolectric point because this will lead to improved retention in the tumour microenvironment relative to a similar antibody with a lower isoelectric point.

Isoelectric point of an antibody may be determined by any suitable method. It may be determined in vitro, for example by electrophoretic methods. Alternatively, isoelectric point may be calculated from basic principles. In this case the resulting isoelectric point is typically referred to as a theoretical isoelectric point. Numerous software programs exist for the in silico calculation of theoretical isoelectric point, for example GP-MAW (version 9.2, from Lighthouse Data). An antibody of the invention preferably has a theoretical isoelectric point (pI) of 9.0 or above, preferably 9.1 or above, more preferably 9.2 or above, most preferably 9.25 or above.

Antibodies of the invention may typically be divided into three groups or classes with different binding profiles to the CD40 receptor, based on their capacity to compete with CD40L for binding to CD40. Competition between an antibody and CD40L for binding to CD40 may be assessed by any suitable method, such as those described herein including in the Examples.

The first class of antibody clones, designated CDRH3A, includes the 1107/1108 clone. Antibodies in this class completely block binding of CD40L to CD40. They bind an epitope close to the CD40L binding site, and/or bind to CD40 in a way that affects the CD40L binding site on CD40 by inducing conformational changes. Antibodies in this class typically comprise a binding domain which binds to module A of domain 2 of human CD40.

The second class of antibody clones, designated CDRH3B, includes 1140/1135, 1138/1135, 1134/1135, 1142/1135. The antibodies in this class do not block CD40L binding to CD40, and thus bind to a separate epitope distinct from the CD40L binding site and the CDRH3A class. The CDRH3B class share a common CDRH3 length of 12 amino acids, and a consensus loop sequence of A, R, G, P, F/V/A, Y, S, S/T, V/Y/F, F/I/L, D, Y (SEQ ID NO: 109). Moreover, the CDRH3B class have the CDRL3 and CDRH1 regions in common. Antibodies in this class typically bind to module B of domain 3 of human CD40.

The third class of antibody clones, designated CDRH3C, includes 1148/1149, 1132/1133, 1146/1147, and 1136/1137. The antibodies in this class exhibit medium competition with CD40L (that is they reduce CD40L binding to CD40), and bind an epitope partly overlapping with that of CD40L or partly affect the CD40L binding to CD40 by inducing conformational changes. This class have a consensus sequence in CDRH3, containing a FG motif. The consensus amino acids, in positions 105-117, are A, R, A/Y/R, V, -/N, F, G, F/M/I, D, Y (SEQ ID NO: 110). The consensus CDRH3 loop size is 9 or 10 amino acids. Antibodies in this class typically bind to module B of domain 1 of human CD40.

Thus, each of the three CDRH3A-C classes represents advantageous properties of CD40 binding which may complement each other, for example in cancer therapy. A therapy based on a mix of the CDRH3A-C antibody classes may induce a strong and potentially synergistic clustering to CD40, resulting in potent and effective immune activation with the potential to produce a potent anti-tumor effect. The mix may consist of two or all three of the disclosed antibody classes. Accordingly the invention also provides a composition comprising at least a first antibody, or fragment thereof; and a second antibody, or fragment thereof, wherein each said antibody is from a different class selected from CDRH3A, CDRH3B and CDRH3C. For example, the composition may comprise an antibody of class CDRH3B and an antibody of class CDRH3C. The invention also provides a composition comprising at least a first antibody, or fragment thereof; a second antibody, or fragment thereof; and a third antibody, or fragment thereof, wherein each said antibody is from a different class selected from CDRH3A, CDRH3B and CDRH3C. Any such a composition may be for use in the treatment of cancer. Such a composition may additionally include a pharmaceutically acceptable carrier. The optimal mix of CDRH3A, B and C classes can be tested by assaying potency in B-cell proliferation. Suitable methods for assaying potency in B-cell proliferation are disclosed in the Examples.

The invention also relates to polynucleotides that encode antibodies of the invention. Thus, a polynucleotide of the invention may encode any antibody as described herein. The terms "nucleic acid molecule" and "polynucleotide" are used interchangeably herein and refer to a polymeric form of nucleotides of any length, either deoxyribonucleotides or ribonucleotides, or analogs thereof. Non-limiting examples of polynucleotides include a gene, a gene fragment, messenger RNA (mRNA), cDNA, recombinant polynucleotides, plasmids, vectors, isolated DNA of any sequence, isolated RNA of any sequence, nucleic acid probes, and primers. A polynucleotide of the invention may be provided in isolated or purified form.

A nucleic acid sequence which "encodes" a selected polypeptide is a nucleic acid molecule which is transcribed (in the case of DNA) and translated (in the case of mRNA) into a polypeptide in vivo when placed under the control of appropriate regulatory sequences. The boundaries of the coding sequence are determined by a start codon at the 5' (amino) terminus and a translation stop codon at the 3' (carboxy) terminus. For the purposes of the invention, such nucleic acid sequences can include, but are not limited to, cDNA from viral, prokaryotic or eukaryotic mRNA, genomic sequences from viral or prokaryotic DNA or RNA, and even synthetic DNA sequences. A transcription termination sequence may be located 3' to the coding sequence.

In one embodiment, a polynucleotide of the invention comprises a sequence which encodes a VH or VL amino acid sequence as described above. The polynucleotide may encode the VH or VL sequence of a specific antibody as disclosed in Table 1. For example, a polynucleotide of the invention may encode a polypeptide comprising the sequence of SEQ ID NO: 61, 63, 65, 67, 69, 71, 73, 75, 77 or 79; or may encode a polypeptide comprising the sequence of SEQ ID NO: 62, 64, 66, 68, 70, 72, 74, 76, 78 or 80; or a variant or fragment of any thereof as described above. A polynucleotide of the invention may encode both the sequences of SEQ ID NOs: 61 and 62; SEQ ID NOs:63 and 64; SEQ ID NOs: 65 and 66; SEQ ID NOs:67 and 68; SEQ ID NOs:69 and 70; SEQ ID NOs:71 and 72; SEQ ID NOs:73 and 74; SEQ ID NOs:75 and 76; SEQ ID NOs:77 and 78; or SEQ ID NOs:79 and 80.

Such a polynucleotide may consist of or comprise a nucleic acid sequence of any one of SEQ ID NOs: 81, 83, 85, 87, 89, 91, 93, 95, 97 or 99; or SEQ ID NOs: 82, 84, 86, 88, 90, 92, 94, 96, 98 or 100. A polynucleotide of the invention may comprise or consist of both the sequences of SEQ ID NOs: 81 and 82; SEQ ID NOs: 83 and 84; SEQ ID NOs: 85 and 86; SEQ ID NOs: 87 and 88; SEQ ID NOs: 89 and 90; SEQ ID NOs:91 and 92; SEQ ID NOs:93 and 94; SEQ ID NOs:95 and 96; SEQ ID NOs:97 and 98; or SEQ ID NOs:99 and 100.

A suitable polynucleotide sequence may alternatively be a variant of one of these specific polynucleotide sequences. For example, a variant may be a substitution, deletion or addition variant of any of the above nucleic acid sequences. A variant polynucleotide may comprise 1, 2, 3, 4, 5, up to 10, up to 20, up to 30, up to 40, up to 50, up to 75 or more nucleic acid substitutions and/or deletions from the sequences given in the sequence listing.

Suitable variants may be at least 70% homologous to a polynucleotide of any one of nucleic acid sequences disclosed in Table 1, preferably at least 80 or 90% and more preferably at least 95%, 97% or 99% homologous thereto. Preferably homology and identity at these levels is present at least with respect to the coding regions of the polynucleotides. Methods of measuring homology are well known in the art and it will be understood by those of skill in the art that in the present context, homology is calculated on the basis of nucleic acid identity. Such homology may exist over a region of at least 15, preferably at least 30, for instance at least 40, 60, 100, 200 or more contiguous nucleotides. Such homology may exist over the entire length of the unmodified polynucleotide sequence.

Methods of measuring polynucleotide homology or identity are known in the art. For example the UWGCG Package provides the BESTFIT program which can be used to calculate homology (e.g. used on its default settings) (Devereux et al (1984) Nucleic Acids Research 12, p 387-395).

The PILEUP and BLAST algorithms can also be used to calculate homology or line up sequences (typically on their default settings), for example as described in Altschul S. F. (1993) J Mol Evol 36:290-300; Altschul, S, F et al (1990) J Mol Biol 215:403-10.

Software for performing BLAST analysis is publicly available through the National Centre for Biotechnology Information (www.ncbi.nlm.nih.gov). This algorithm involves first identifying high scoring sequence pair (HSPs) by identifying short words of length W in the query sequence that either match or satisfy some positive-valued threshold score T when aligned with a word of the same length in a database sequence. T is referred to as the neighbourhood word score threshold (Altschul et al, supra). These initial neighbourhood word hits act as seeds for initiating searches to find HSPs containing them. The word hits are extended in both directions along each sequence for as far as the cumulative alignment score can be increased. Extensions for the word hits in each direction are halted when: the cumulative alignment score goes to zero or below, due to the accumulation of one or more negative-scoring residue alignments; or the end of either sequence is reached. The BLAST algorithm parameters W, T and X determine the sensitivity and speed of the alignment. The BLAST program uses as defaults a word length (W) of 11, the BLOSUM62 scoring matrix (see Henikoff and Henikoff (1992) Proc. Natl. Acad. Sci. USA 89:10915-10919) alignments (B) of 50, expectation (E) of 10, M=5, N=4, and a comparison of both strands.

The BLAST algorithm performs a statistical analysis of the similarity between two sequences; see e.g., Karlin and Altschul (1993) Proc. Natl. Acad. Sci. USA 90:5873-5787. One measure of similarity provided by the BLAST algorithm is the smallest sum probability (P(N)), which provides an indication of the probability by which a match between two nucleotide or amino acid sequences would occur by chance. For example, a sequence is considered similar to another sequence if the smallest sum probability in comparison of the first sequence to the second sequence is less than about 1, preferably less than about 0.1, more preferably less than about 0.01, and most preferably less than about 0.001.

The homologue may differ from a sequence in the relevant polynucleotide by less than 3, 5, 10, 15, 20 or more mutations (each of which may be a substitution, deletion or insertion). These mutations may be measured over a region of at least 30, for instance at least 40, 60 or 100 or more contiguous nucleotides of the homologue.

In one embodiment, a variant sequence may vary from the specific sequences given in the sequence listing by virtue of the redundancy in the genetic code. The DNA code has 4 primary nucleic acid residues (A, T, C and G) and uses these to "spell" three letter codons which represent the amino acids the proteins encoded in an organism's genes. The linear sequence of codons along the DNA molecule is translated into the linear sequence of amino acids in the protein(s) encoded by those genes. The code is highly degenerate, with 61 codons coding for the 20 natural amino acids and 3 codons representing "stop" signals. Thus, most amino acids are coded for by more than one codon—in fact several are coded for by four or more different codons. A variant polynucleotide of the invention may therefore encode the same polypeptide sequence as another polynucleotide of the invention, but may have a different nucleic acid sequence due to the use of different codons to encode the same amino acids.

Polynucleotide "fragments" according to the invention may be made by truncation, e.g. by removal of one or more nucleotides from one or both ends of a polynucleotide. Up to 10, up to 20, up to 30, up to 40, up to 50, up to 75, up to 100, up to 200 or more amino acids may be removed from the 3' and/or 5' end of the polynucleotide in this way. Fragments may also be generated by one or more internal deletions. Such fragments may be derived from a sequence of SEQ ID NOs: 2 and 8 or may be derived from a variant polynucleotide as described herein. Preferably such fragments are between 30 and 300 residues in length, e.g. 30 to 300, 30 to 200, 30 to 100, 100 to 200 or 200 to 300 residues. Alternatively, fragments of the invention may be longer sequences, for example comprising at least 50%, at least 60%, at least 70%, at least 80% or at least 90% of a full length polynucleotide of the invention.

An antibody of the invention may thus be produced from or delivered in the form of a polynucleotide which encodes, and is capable of expressing, it. Where the antibody comprises two or more chains, a polynucleotide of the invention may encode one or more antibody chains. For example, a polynucleotide of the invention may encode an antibody light chain, an antibody heavy chain or both. Two polynucleotides may be provided, one of which encodes an antibody light chain and the other of which encodes the corresponding antibody heavy chain. Such a polynucleotide or pair of polynucleotides may be expressed together such that an antibody of the invention is generated.

Polynucleotides of the invention can be synthesised according to methods well known in the art, as described by way of example in Sambrook et al (1989, Molecular Cloning—a laboratory manual; Cold Spring Harbor Press).

The nucleic acid molecules of the present invention may be provided in the form of an expression cassette which includes control sequences operably linked to the inserted sequence, thus allowing for expression of the antibody of the invention in vivo. These expression cassettes, in turn, are typically provided within vectors (e.g., plasmids or recombinant viral vectors). Such an expression cassette may be administered directly to a host subject. Alternatively, a vector comprising a polynucleotide of the invention may be administered to a host subject. Preferably the polynucleotide is prepared and/or administered using a genetic vector. A suitable vector may be any vector which is capable of carrying a sufficient amount of genetic information, and allowing expression of a polypeptide of the invention.

The present invention thus includes expression vectors that comprise such polynucleotide sequences. Such expression vectors are routinely constructed in the art of molecular biology and may for example involve the use of plasmid DNA and appropriate initiators, promoters, enhancers and other elements, such as for example polyadenylation signals which may be necessary, and which are positioned in the correct orientation, in order to allow for expression of a peptide of the invention. Other suitable vectors would be apparent to persons skilled in the art. By way of further example in this regard we refer to Sambrook et al.

The invention also includes cells that have been modified to express an antibody of the invention. Such cells include transient, or preferably stable higher eukaryotic cell lines, such as mammalian cells or insect cells, lower eukaryotic cells, such as yeast or prokaryotic cells such as bacterial cells. Particular examples of cells which may be modified by insertion of vectors or expression cassettes encoding for an antibody of the invention include mammalian HEK293T, CHO, HeLa, NS0 and COS cells. Preferably the cell line selected will be one which is not only stable, but also allows for mature glycosylation and cell surface expression of a polypeptide.

Such cell lines of the invention may be cultured using routine methods to produce an antibody of the invention, or may be used therapeutically or prophylactically to deliver antibodies of the invention to a subject. Alternatively, polynucleotides, expression cassettes or vectors of the invention may be administered to a cell from a subject ex vivo and the cell then returned to the body of the subject.

In another aspect, the present invention provides compositions and formulations comprising molecules of the invention, such as the antibodies, polynucleotides, vectors and cells described herein. For example, the invention provides a pharmaceutical composition comprising one or more molecules of the invention, such as one or more antibodies of the invention, formulated together with a pharmaceutically acceptable carrier.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for parenteral, e.g. intravenous, intramuscular or subcutaneous administration (e.g., by injection or infusion). Depending on the route of administration, the antibody may be coated in a material to protect the antibody from the action of acids and other natural conditions that may inactivate or denature the antibody.

Preferred pharmaceutically acceptable carriers comprise aqueous carriers or diluents. Examples of suitable aqueous carriers that may be employed in the pharmaceutical compositions of the invention include water, buffered water and saline. Examples of other carriers include ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants. In many cases, it will be preferable to include isotonic agents, for example, sugars, polyalcohols such as mannitol, sorbitol, or sodium chloride in the composition.

A pharmaceutical composition of the invention also may include a pharmaceutically acceptable anti-oxidant. These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Therapeutic compositions typically must be sterile and stable under the conditions of manufacture and storage. The composition can be formulated as a solution, microemulsion, liposome, or other ordered structure suitable to high drug concentration.

Sterile injectable solutions can be prepared by incorporating the active agent (e.g. antibody) in the required amount in an appropriate solvent with one or a combination of ingredients enumerated above, as required, followed by sterilization microfiltration. Generally, dispersions are prepared by incorporating the active agent into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active agent plus any additional desired ingredient from a previously sterile-filtered solution thereof.

Pharmaceutical compositions of the invention may comprise additional active ingredients as well as an antibody of the invention. As mentioned above, compositions of the invention may comprise one or more antibodies of the invention. They may also comprise additional therapeutic or prophylactic agents.

Also within the scope of the present invention are kits comprising antibodies or other compositions of the invention and instructions for use. The kit may further contain one ore more additional reagents, such as an additional therapeutic or prophylactic agent as discussed above.

The antibodies in accordance with the present invention maybe used in therapy. In therapeutic applications, antibodies or compositions are administered to a subject already suffering from a disorder or condition, in an amount sufficient to cure, alleviate or partially arrest the condition or one or more of its symptoms. Such therapeutic treatment may result in a decrease in severity of disease symptoms, or an increase in frequency or duration of symptom-free periods. An amount adequate to accomplish this is defined as "therapeutically effective amount". Effective amounts for a given purpose will depend on the severity of the disease or injury as well as the weight and general state of the subject. As used herein, the term "subject" includes any human.

In particular, antibodies to CD40 may be useful in the treatment of cancer. Accordingly, the invention provides an antibody of the invention, or fragment thereof, for use in the treatment of cancer. The invention also provides a method of treating cancer comprising administering to an individual an antibody of the invention, or a fragment thereof. The invention also provides an antibody of the invention, or fragment thereof, for use in the manufacture of a medicament for the treatment of cancer.

The cancer may be prostate cancer, breast cancer, colorectal cancer, pancreatic cancer, ovarian cancer, lung cancer, cervical cancer, rhabdomyosarcoma, neuroblastoma, multiple myeloma, leukemia, acute lymphoblastic leukemia, melanoma, bladder cancer, head and neck cancer, lymphoma, glioblastoma, lymphoma or skin cancer.

In particular embodiments, the antibody of the invention may be linked (directly or indirectly) to another moiety. The other moiety may be a therapeutic agent such as a cytotoxic moiety or a drug. The other moiety may be a detectable label. The other moiety may be a binding moiety, such as a tumour-specific antibody or a polypeptide binding domain specific for a therapeutic target, preferably a therapeutic target associated with cancer, which target is not human CD40. The resulting bispecific molecule may be for use in the treatment of cancer. A preferred therapeutic target which is not human CD40 is human CTLA-4. Other targets include PD1, PD-L1, CD27, HVEM, LAG3 and TNFR family members. Thus, as an example, the antibody of the invention, or an antigen binding fragment thereof, may be linked (directly or indirectly) to a polypeptide binding domain specific for human CTLA-4. Said binding domain may comprise or consist of (i) the amino acid sequence of SEQ ID NO: 105 (the sequence of the monocellular extracellular domain of wild-type human CD86); or (ii) an amino acid sequence in which at least one amino acid is changed when compared to the amino acid sequence of SEQ ID NO: 105 provided that said binding domain binds to human CTLA-4 with higher affinity than does wild-type human CD86. Preferred polypeptide binding domains specific for human CTLA-4 include the polypeptides which comprise or consist of the amino acid sequence of any one of SEQ ID NOS: 106, 107 and 108, each of which is a variant of the extracellular domain of wild-type human CD86.

The therapeutic agent or a detectable label may be directly attached, for example by chemical conjugation, to an antibody of the invention. Methods for conjugating agents or labels to an antibody are known in the art. For example, carbodiimide conjugation (Bauminger & Wilchek (1980) Methods Enzymol. 70, 151-159) may be used to conjugate a variety of agents, including doxorubicin, to antibodies or peptides. The water-soluble carbodiimide, 1-ethyl-3-(3-dimethylaminopropyl) carbodiimide (EDC) is particularly useful for conjugating a functional moiety to a binding moiety.

Other methods for conjugating a moiety to antibodies can also be used. For example, sodium periodate oxidation followed by reductive alkylation of appropriate reactants can be used, as can glutaraldehyde cross-linking. However, it is recognised that, regardless of which method of producing a conjugate of the invention is selected, a determination must be made that the antibody maintains its targeting ability and that the functional moiety maintains its relevant function.

A cytotoxic moiety may be directly and/or indirectly cytotoxic. By "directly cytotoxic" it is meant that the moiety is one which on its own is cytotoxic. By "indirectly cytotoxic" it is meant that the moiety is one which, although is not itself cytotoxic, can induce cytotoxicity, for example by its action on a further molecule or by further action on it. The cytotoxic moiety may be cytotoxic only when intracellular and is preferably not cytotoxic when extracellular.

Preferably, the invention provides an antibody or antigen-binding fragment, or a variant, fusion or derivative thereof, wherein the cytotoxic moiety is a directly cytotoxic chemotherapeutic agent. Optionally, the cytotoxic moiety is a directly cytotoxic polypeptide. Cytotoxic chemotherapeutic agents are well known in the art.

Cytotoxic chemotherapeutic agents, such as anticancer agents, include: alkylating agents including nitrogen mustards such as mechlorethamine (HN2), cyclophosphamide, ifosfamide, melphalan (L-sarcolysin) and chlorambucil; ethylenimines and methylmelamines such as hexamethylmelamine, thiotepa; alkyl sulphonates such as busulfan; nitrosoureas such as carmustine (BCNU), lomustine (CCNU), semustine (methyl-CCNU) and streptozocin (streptozotocin); and triazenes such as decarbazine (DTIC; dimethyltriazenoimidazole-carboxamide); Antimetabolites including folic acid analogues such as methotrexate (amethopterin); pyrimidine analogues such as fluorouracil (5-fluorouracil; 5-FU), floxuridine (fluorodeoxyuridine; FUdR) and cytarabine (cytosine arabinoside); and purine analogues and related inhibitors such as mercaptopurine (6-mercaptopurine; 6-MP), thioguanine (6-thioguanine; TG) and pentostatin (2'-deoxycoformycin). Natural Products including vinca alkaloids such as vinblastine (VLB) and vincristine; epipodophyllotoxins such as etoposide and teniposide; antibiotics such as dactinomycin (actinomycin D), daunorubicin (daunomycin; rubidomycin), doxorubicin, bleomycin, plicamycin (mithramycin) and mitomycin (mitomycin C); enzymes such as L-asparaginase; and biological response modifiers such as interferon alphenomes. Miscellaneous agents including platinum coordination complexes such as cisplatin (cis-DDP) and carboplatin; anthracenedione such as mitoxantrone and anthracycline; substituted urea such as hydroxyurea; methyl hydrazine derivative such as procarbazine (N-methylhydrazine, MIH); and adrenocortical suppressant such as mitotane (o,p'-DDD) and aminoglutethimide; taxol and analogues/derivatives; and hormone agonists/antagonists such as flutamide and tamoxifen.

In one embodiment of the invention, the cytotoxic moiety is a cytotoxic peptide or polypeptide moiety which leads to cell death. Cytotoxic peptide and polypeptide moieties are well known in the art and include, for example, ricin, abrin, *Pseudomonas* exotoxin, tissue factor and the like. Methods for linking them to targeting moieties such as antibodies are also known in the art. Other ribosome inactivating proteins are described as cytotoxic agents in WO 96/06641. *Pseudomonas* exotoxin may also be used as the cytotoxic polypeptide. Certain cytokines, such as TNFα and IL-2, may also be useful as cytotoxic agents.

Certain radioactive atoms may also be cytotoxic if delivered in sufficient doses. Thus, the cytotoxic moiety may comprise a radioactive atom which, in use, delivers a sufficient quantity of radioactivity to the target site so as to be cytotoxic. Suitable radioactive atoms include phosphorus-32, iodine-125, iodine-131, indium-111, rhenium-186, rhenium-188 or yttrium-90, or any other isotope which emits enough energy to destroy neighbouring cells, organelles or nucleic acid. Preferably, the isotopes and density of radioactive atoms in the agents of the invention are such that a dose of more than 4000 cGy (preferably at least 6000, 8000 or 10000 cGy) is delivered to the target site and, preferably, to the cells at the target site and their organelles, particularly the nucleus.

The radioactive atom may be attached to the antibody, antigen-binding fragment, variant, fusion or derivative thereof in known ways. For example, EDTA or another chelating agent may be attached to the binding moiety and used to attach 111In or 90Y. Tyrosine residues may be directly labelled with 125I or 131I.

The cytotoxic moiety may be a suitable indirectly-cytotoxic polypeptide. In a particularly preferred embodiment, the indirectly cytotoxic polypeptide is a polypeptide which has enzymatic activity and can convert a non-toxic and/or relatively non-toxic prodrug into a cytotoxic drug. With antibodies, this type of system is often referred to as ADEPT (Antibody-Directed Enzyme Prodrug Therapy). The system requires that the antibody locates the enzymatic portion to the desired site in the body of the patient and after allowing time for the enzyme to localise at the site, administering a prodrug which is a substrate for the enzyme, the end product of the catalysis being a cytotoxic compound. The object of the approach is to maximise the concentration of drug at the desired site and to minimise the concentration of drug in normal tissues. In a preferred embodiment, the cytotoxic moiety is capable of converting a non-cytotoxic prodrug into a cytotoxic drug.

The enzyme and prodrug of the system using a targeted enzyme as described herein may be any of those previously proposed. The cytotoxic substance may be any existing anti-cancer drug such as an alkylating agent; an agent which intercalates in DNA; an agent which inhibits any key enzymes such as dihydrofolate reductase, thymidine synthetase, ribonucleotide reductase, nucleoside kinases or topoisomerase; or an agent which effects cell death by interacting with any other cellular constituent. Etoposide is an example of a topoisomerase inhibitor.

Reported prodrug systems include those listed in Table 2, below.

Suitable enzymes for forming part of an enzymatic portion include: exopeptidases, such as carboxypeptidases G, G1 and G2 (for glutamylated mustard prodrugs), carboxypeptidases A and B (for MTX-based prodrugs) and aminopeptidases (for 2-α-aminocyl MTC prodrugs); endopeptidases, such as e.g. thrombolysin (for thrombin prodrugs); hydrolases, such as phosphatases (e.g. alkaline phosphatase) or sulphatases (e.g. aryl sulphatases) (for phosphylated or sulphated prodrugs); amidases, such as penicillin amidases and arylacyl amidase; lactamases, such as β-lactamases; glycosidases, such as β-glucuronidase (for β-glucuronamide anthracyclines), α-galactosidase (for amygdalin) and β-galactosidase (for β-galactose anthracycline); deaminases, such as cytosine deaminase (for 5FC); kinases, such as urokinase and thymidine kinase (for gancyclovir); reductases, such as nitroreductase (for CB1954 and analogues), azoreductase (for azobenzene mustards) and DT-diaphorase (for CB1954); oxidases, such as glucose oxidase (for glucose), xanthine oxidase (for xanthine) and lactoperoxidase; DL-racemases, catalytic antibodies and cyclodextrins.

Preferably, the prodrug is relatively non-toxic compared to the cytotoxic drug. Typically, it has less than 10% of the toxicity, preferably less than 1% of the toxicity as measured in a suitable in vitro cytotoxicity test.

It is likely that the moiety which is able to convert a prodrug to a cytotoxic drug will be active in isolation from the rest of the agent of the invention but it is necessary only for it to be active when (a) it is in combination with the rest of the agent of the invention and (b) the agent of the invention is attached to, adjacent to or internalised in target cells.

When each moiety is a polypeptide, the two portions may be linked together by any of the conventional ways of cross-linking polypeptides. For example, the antibody, antigen-binding fragment, variant, fusion or derivative thereof, may be enriched with thiol groups and the further moiety reacted with a bifunctional agent capable of reacting with those thiol groups, for example the N-hydroxysuccinimide ester of iodoacetic acid (NHIA) or N-succinimidyl-3-(2-pyridyldithio)propionate (SPDP). Amide and thioether bonds, for example achieved with m-maleimidobenzoyl-N-hydroxysuccinimide ester, are generally more stable in vivo than disulphide bonds.

Alternatively, the antibody, antigen-binding fragment, variant, fusion or derivative thereof, may be produced as a fusion compound by recombinant DNA techniques whereby a length of DNA comprises respect¬ive regions encoding the two moieties of the agent of the invention either adjacent one another or separated by a region encoding a linker peptide which does not destroy the desired properties of the agent. Conceivably, the two portions of the agent may overlap wholly or partly.

TABLE 2

| Enzyme | Prodrug |
| --- | --- |
| Carboxypeptidase G2 | Derivatives of L-glutamic acid and benzoic acid mustards, aniline mustards, phenol mustards and phenylenediamine mustards; fluorinated derivatives of these |
| Alkaline phosphatase | Etoposide phosphate |
|  | Mitomycin phosphate |
| Beta-glucuronidase | p-Hydroxyaniline mustard-glucuronide |
|  | Epirubicin-glucuronide |
| Penicillin-V-amidase | Adriamycin-N phenoxyacetyl |
| Penicillin-G-amidase | N-(4'-hydroxyphenyl acetyl) palytoxin |
|  | Doxorubicin and melphalan |
| Beta-lactamase | Nitrogen mustard-cephalosporin p-phenylenediamine; doxorubicin derivatives; vinblastine derivative-cephalosporin, cephalosporin mustard; a taxol derivative |
| Beta-glucosidase | Cyanophenylmethyl-beta-D-gluco-pyranosiduronic acid |
| Nitroreductase | 5-(Azaridin-1-yl-)-2,4-dinitrobenzamide |
| Cytosine deaminase | 5-Fluorocytosine |
| Carboxypeptidase A | Methotrexate-alanine |

The cytotoxic moiety may be a radiosensitizer. Radiosensitizers include fluoropyrimidines, thymidine analogues, hydroxyurea, gemcitabine, fludarabine, nicotinamide, halogenated pyrimidines, 3-aminobenzamide, 3-aminobenzodiamide, etanixadole, pimonidazole and misonidazole. Also, delivery of genes into cells can radiosensitise them, for example delivery of the p53 gene or cyclin D. The further moiety may be one which becomes cytotoxic, or releases a cytotoxic moiety, upon irradiation. For example, the boron-10 isotope, when appropriately irradiated, releases α particles which are cytotoxic. Similarly, the cytotoxic moiety may be one which is useful in photodynamic therapy such as photofrin.

The further moiety may comprise a nucleic acid molecule which is directly or indirectly cytotoxic. For example, the nucleic acid molecule may be an antisense oligonucleotide which, upon localisation at the target site is able to enter cells and lead to their death. The oligonucleotide, therefore, may be one which prevents expression of an essential gene, or one which leads to a change in gene expression which causes apoptosis. Alternatively, the cytotoxic moiety is a nucleic acid molecule encoding a directly and/or indirectly cytotoxic polypeptide. Examples of suitable oligonucleotides include those directed at bcl-2, DNA polymerase α and topoisomerase IIα. Peptide nucleic acids may be useful in place of conventional nucleic acids.

The antibody, antigen-binding fragment, variant, fusion or derivative thereof may be comprised in a delivery vehicle for delivering nucleic acid to the target. The delivery vehicle may be any suitable delivery vehicle. It may, for example, be a liposome containing nucleic acid, or it may be a virus or virus-like particle which is able to deliver nucleic acid. In these cases, the molecule to be delivered is typically present on the surface of the delivery vehicle. For example, an antibody or fragment may be present in the outer surface of a liposome and the nucleic acid to be delivered may be present in the interior of the liposome. As another example, a viral vector, such as a retroviral or adenoviral vector, is engineered so that the binding moiety is attached to or located in the surface of the viral particle thus enabling the viral particle to be targeted to the desired site. Immunoliposomes (antibody-directed liposomes) may be used. In one method for the preparation of immuno-liposomes, MPB-PE (N-[4-(p-maleimidophenyl)-butyryl]-phosphatidylethanolamine) is synthesised according to the method of Martin & Papahadjopoulos (1982) J. Biol. Chem. 257, 286-288. MPB-PE is incorporated into the liposomal bilayers to allow a covalent coupling of the antibody, or fragment thereof, to the liposomal surface. The liposome is conveniently loaded with the DNA or other genetic construct for delivery to the target cells, for example, by forming the said liposomes in a solution of the DNA or other genetic construct, followed by sequential extrusion through polycarbonate membrane filters with 0.6 μm and 0.2 μm pore size under nitrogen pressures up to 0.8 MPa. After extrusion, entrapped DNA construct is separated from free DNA construct by ultracentrifugation at 80 000×g for 45 min. Freshly prepared MPB-PE-liposomes in deoxygenated buffer are mixed with freshly prepared antibody (or fragment thereof) and the coupling reactions are carried out in a nitrogen atmosphere at 4° C. under constant end over end rotation overnight. The immunoliposomes are separated from unconjugated antibodies by ultracentrifugation at 80 000×g for 45 min. Immunoliposomes may be injected intraperitoneally or directly into the tumour.

The nucleic acid delivered to the target site may be any suitable DNA which leads, directly or indirectly, to cytotoxicity. For example, the nucleic acid may encode a ribozyme which is cytotoxic to the cell, or it may encode an enzyme which is able to convert a substantially non-toxic prodrug into a cytotoxic drug (this latter system is sometime called GDEPT: Gene Directed Enzyme Prodrug Therapy). Suitable ribozymes include polymerases, dephosphorylases, and restriction endonucleases. Suitable targets for ribozymes include transcription factors such as c-fos and c-myc, and bcl-2. Similar considerations concerning the choice of enzyme and prodrug apply to the GDEPT system as to the ADEPT system described above. The nucleic acid delivered to the target site may encode a directly cytotoxic polypeptide.

The therapeutic agent linked to the antibody may comprise a polypeptide or a polynucleotide encoding a polypeptide which is not either directly or indirectly cytotoxic but is of therapeutic benefit. Examples of such polypeptides include anti-proliferative or anti-inflammatory cytokines, and anti-proliferative, immunomodulatory or factors influencing blood clotting which may be of benefit in medicine, for example in the treatment of cancer. The agent may usefully be an inhibitor of angiogenesis such as the peptides angiostatin or endostatin. The agent may also usefully be an enzyme which converts a precursor polypeptide to angiostatin or endostatin. Human matrix metallo-proteases such as macrophage elastase, gelatinase and stromolysin convert plasminogen to angiostatin. Plasminogen is a precursor of angiostatin.

The antibody may be linked to a detectable label. By "detectable label" it is meant that the antibody is linked to a moiety which, when located at the target site following administration of the antibody into a patient, may be detected, typically non-invasively from outside the body and the site of the target located. Thus, the antibody may be useful in imaging and diagnosis.

Typically, the label is or comprises a radioactive atom which is useful in imaging. Suitable radioactive atoms include 99mTc and 123I for scintigraphic studies. Other labels include, for example, spin labels for magnetic resonance imaging (MRI) such as 123I again, 131I, 111In, 19F, 13C, 15N, 17O, gadolinium, manganese or iron. Clearly, the sufficient of the appropriate atomic isotopes must be linked to the antibody in order for the molecule to be readily detectable.

The radio- or other labels may be incorporated in known ways. For example, the antibody, or fragment thereof, may be biosynthesised or may be synthesised by chemical amino acid synthesis using suitable amino acid precursors involving, for example, fluorine-19 in place of hydrogen. Labels such as 99mTc, 123I, 186Rh, 188Rh and 111In can, for example, be attached via cysteine residues in polypeptides. Yttrium-90 can be attached via a lysine residue. Preferably, the detectable label comprises a radioactive atom, such as, for example technetium-99m or iodine-123. Alternatively, the detectable label may be selected from the group comprising: iodine-123; iodine-131; indium-111; fluorine-19; carbon-13; nitrogen-15; oxygen-17; gadolinium; manganese; iron.

In one embodiment, an antibody of the invention is able to bind selectively to a directly or indirectly cytotoxic moiety or to a detectable label. Thus, in this embodiment, the antibody is linked to a moiety which selectively binds to a further compound or component which is cytotoxic or readily detectable.

An antibody or fragment of the present invention, or a composition comprising said antibody or fragment, may be administered via one or more routes of administration using one or more of a variety of methods known in the art. As will be appreciated by the skilled artisan, the route and/or mode of administration will vary depending upon the desired results. Preferred routes of administration for antibodies or compositions of the invention include intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection. Alternatively, an antibody or composition of the invention can be administered via a non-parenteral route, such as a topical, epidermal or mucosal route of administration.

Local administration is preferred, including peritumoral, juxtatumoral, intratumoral, intralesional, perilesional, intra cavity infusion, intravesicle administration, and inhalation. However, the antibody or composition may also be administered systemically.

A suitable dosage of an antibody of the invention may be determined by a skilled medical practitioner. Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular antibody employed, the route of administration, the time of administration, the rate of excretion of the antibody, the duration of the treatment, other drugs, compounds and/or materials used in combination with the particular compositions employed, the age, sex, weight, condition, general health and prior medical history of the patient being treated, and like factors well known in the medical arts.

A suitable dose of an antibody of the invention may be, for example, in the range of from about 0.1 µg/kg to about 100 mg/kg body weight of the patient to be treated. For example, a suitable dosage may be from about 1 µg/kg to about 10 mg/kg body weight per day or from about 10 g/kg to about 5 mg/kg body weight per day.

Dosage regimens may be adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier.

Antibodies may be administered in a single dose or in multiple doses. The multiple doses may be administered via the same or different routes and to the same or different locations. Alternatively, antibodies can be administered as a sustained release formulation, in which case less frequent administration is required. Dosage and frequency may vary depending on the half-life of the antibody in the patient and the duration of treatment that is desired. The dosage and frequency of administration can also vary depending on whether the treatment is prophylactic or therapeutic. In prophylactic applications, a relatively low dosage may be administered at relatively infrequent intervals over a long period of time. In therapeutic applications, a relatively high dosage may be administered, for example until the patient shows partial or complete amelioration of symptoms of disease.

Combined administration of two or more agents may be achieved in a number of different ways. In one embodiment, the antibody and the other agent may be administered together in a single composition. In another embodiment, the antibody and the other agent may be administered in separate compositions as part of a combined therapy. For example, the antibody may be administered before, after or concurrently with the other agent. The antibody of the invention may be administered in combination with or sequentially to tumor targeting antibodies, target therapy, pathway inhibitors or other immunomodulatory antibodies targeting eg. PD-1, PD-L1, CD137, GITR, OX40, CTLA-4, CD27, HVEM, LtBR, and LAG3. Further the antibody of the invention may also be combined with local radiation.

The present invention is further illustrated by the following examples which should not be construed as further limiting. The contents of all figures and all references, patents and published patent applications cited throughout this application are expressly incorporated herein by reference.

EXAMPLES

Example 1—Selection of Antibody Clones from Human scFV Antibody Library

Selections for CD40 binding ScFv antibody clones were performed using a fully human ScFv library containing more than $1\times10^{10}$ unique members. The general procedure for selecting the CD40 binding antibody clones were as follows:

Phage stocks were initially pre-selected against streptavidin coated magnetic beads (Dynabeads M-280, Invitrogen, #112.06D) or against beriglobin-biotin ((ZBL Behring) pre-coupled streptavidin in order to remove non-specific binders. An excess of mIgG (Jackson 015-000-003) was present in all selection rounds in order to remove presumptive Fc-binders. Selections against biotinylated Fc-fused CD40 (Ancell 504-030) were performed for 5 selection rounds (concentration range 100 nM to 0.1 nM). Bovine serum albumin (BSA, #) was included as a blocking agent throughout the selection procedure at a final concentration of 1%.

The pre-selected ScFv phage library was incubated with either biotinylated CD40 for at least 1 h and thereafter, phage expressing CD40 binding ScFv were captured on streptavidin beads or the pre-selected scFv phage library were added to blocked eppendorf tubes containing CD40 antigen for 1 h. The different complexes were washed repeatedly with increased stringency. Trypsin (Lonza, #17-161E) digestion was used to elute binding phage from the streptavidin beads and Aprotinin Roche, #1023662401) was added. Eluted phage was used for infection of log-phase XL1-Blue cells (originating from #200228, Stratagene) for 30 min at 37° C. which were spread on QTrays (2×YT Agar/Ampicillin/Tetracycline/Glucose 50 µg/mL, 10 µg/mL, 1%) and incubated over-night at 37° C.

The following day, the Qtray/s was scraped, the bacteria's diluted and allowed to grow to log phase. Phage stock was made by infecting log phase XL1-Blue with an 20× excess of helper phage M13K07 (New England Biolabs, N0315S), the expression of phage surface displayed ScFv was induced by the addition of IPTG and the induced cultures were grown over-night at 30° C. Amplified phage stock was PEG/NaCl (20% w/v) precipitated prior to the next selection round. The number of phage eluted as well as the number of input phage in the selection rounds was monitored by titration (i. e infection of log phase XL1-Blue cells and counting of colony forming units).

Example 2—Screening and Sequence Determination of scFv Antibody Clones

Screening for antibody clones binding to CD40 target and subsequent sequencing were performed. Binders were identified by detecting binding to CD40 in a phage-ELISA assay. The identified antibody clones were sequenced and their CDRs (complementary determining regions) were determined—see Example 5.

Single clones from the later selection rounds were picked and cultured in 96-well plates and grown over-night. The following day, new plates were inoculated with the over-night cultures and grown in low glucose media (2×YT/Ampicillin/Tetracycline/Glucose 50 µg/mL, 10 µg/mL, 0.05%) and 20× excess of M13K07 helper phage (New England Biolabs, N0315S) was added when the cultures reached log-phase. The expression of phage surface displayed ScFv was induced by the addition of ITPG.

The next day, supernatants were collected and used in phage-ELISA. An empty vector was used as negative control and a phagemid encoding a known CD40 binder was included as a positive control. High binding plates (Greiner #781074) were coated with CD40 (R&D Systems #629-LR) at 0.1-1 µg/ml, or with Orencia® (Bristol Myer Scribb) (0.5 µg/ml). Coated wells were blocked and the phage containing supernatants were added. Binding phage was detected with anti M13-HRP (GE, 27-9421-01) and Super Signal™ Pico Chemiluminescent (Pierce, #37069) was used as substrate. Orencia® were included to exclude the possibility of selecting phages that bind to Fc-regions.

The theoretical isoelectric point, pI, was calculated for each antibody using GP-MAW software (version 9.2, from Lighthouse Data), assuming that all cysteines are oxidized (S-S bridges are formed). The results are shown in Table 3. The antibody clones of the invention have high theoretical pI values, which is favourable for local immunotherapy in treatment of cancer.

TABLE 3

| In silico determined isoelectric point | |
| --- | --- |
| Antibody Clone | Theoretical pI |
| 1136/1137 | 9.22 |
| 1132/1133 | 9.29 |
| 1148/1149 | 9.22 |
| 1140/1135 | 9.22 |
| 1138/1135 | 9.21 |
| 1134/1135 | 9.22 |
| 1107/1108 | 9.30 |
| 1142/1135 | 9.22 |
| 1146/1147 | 9.28 |
| 1150/1151 | 9.12 |

Purified full IgG molecules were analysed with ELISA. High binding flat bottom LIA plates (Greiner #655074) were coated with Fc-fused CD40 (Ancell, #504-820) at 0.05 µg/ml, and milk powder were used at 3% for blocking and at 1% for dilution. The antibodies to be tested were added in serial dilutions starting at 50 µg/ml and detection was carried out using HRP conjugated goat anti human Ig-Fc (Jackson ImmunoResearch, #109-035-098) and Super Signal™ Pico Chemiluminescent (ThermoScientific, #37069) was used as substrate. Results of the ELISA are shown in FIG. 1 and calculated EC50 in Table 4.

TABLE 4

| CD40 binding ELISA (EC50) in ng/ml | | | | | | | | | |
| --- | --- | --- | --- | --- | --- | --- | --- | --- | --- |
| Clone # | | | | | | | | | |
| 1138/1135 | 1136/1137 | 1146/1147 | 1148/1149 | 1132/1133 | 1134/1135 | 1142/1135 | 1140/1135 | 1107/1108 | 1150/1151 |
| EC50 970 | 1400 | 580 | 2200 | 280 | 25 | 560 | 310 | 34 | 41 |

The phagemids binding to CD40 were sequenced. DNA sequencing was performed according to standard methods at MWG (Germany). CDR regions were determined using the IMGT® system. Alignment tools are available at www.imgt.org/.

Example 3—Cloning to Full Antibody Format and Further Assaying for Binding to CD40

The CD40 binding antibody clones were re-cloned into full IgG format employing two expression vectors for VH and VL respectively. Plasmids were prepared and the constructs were verified by sequencing. 293 FreeStyle™ cells (Invitrogen, # R790-07) were transfected with the plasmids VH and VL and after 6 days, supernatants were collected and the expressed full IgG were purified on Protein A FF columns (GE Healthcare). The purified antibodies were analysed using SDS-PAGE, A280 and HPLC.

All antibodies bind CD40 and show no unspecific binding to Orencia® (data not shown). The affinity for CD40 for all antibodies has been confirmed with Surface Plasmon Resonance (see Example 6 below).

Figure 2:
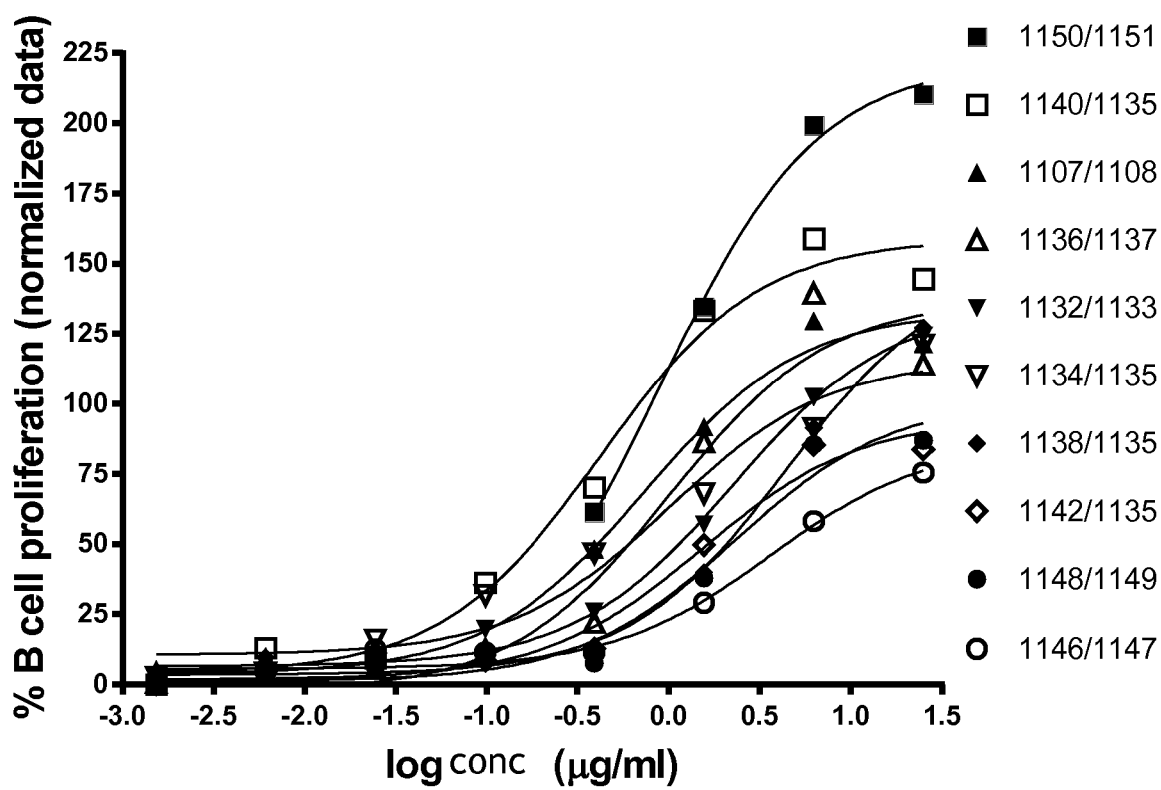
FIG. 2 shows the results of a B cell proliferation assay for the antibodies listed in the figure legend.

Binding of agonistic anti-CD40 antibodies to CD40 on B-cells results in B-cell activation and proliferation, homeotypic aggregation and up-regulation of surface markers such as CD23, CD30, CD80, CD86, Fas, major histocompatibility complex (MHC) II and soluble cytokines, e.g. IL-6, TNF-α and TNF-β (Schönbeck and Libby, 2001, Cell Mol Life 58(1), 4-43). Measuring CD40 induced B-cell proliferation is commonly used to evaluate CD40 agonistic antibodies (Pound et al, 1999, Int Immunol, (11), 11-20). Accordingly, a B cell proliferation assay was performed for the full IgG molecules. B-cells were isolated by leucocyte filters from 2-4 donors and incubated with the purified full IgG molecules and IL-4 for three days. Human IgG1 was used as a negative control. The B-cell proliferation was measured with Cell-Titer Glo™ (Promega, # G7571) measuring the ATP content in the cells. Results of the B cell proliferation assay for all antibodies are shown in FIG. 2 and calculated EC50 in Table 5. The antibody clones of the invention are all agonistic anti-CD40 antibodies.

TABLE 5

Potency B cell proliferation (EC50) in µg/ml

| | Clone # | | | | | | | | | |
|---|---|---|---|---|---|---|---|---|---|---|
| | 1138/ 1135 | 1136/ 1137 | 1146/ 1147 | 1148/ 1149 | 1142/ 1135 | 1132/ 1133 | 1134/ 1135 | 1140/ 1135 | 1107/ 1108 | 1150/ 1151 |
| EC50 | 4.5 | 1.0 | 3.6 | 2.3 | 1.5 | 2.2 | 1.0 | 0.4 | 0.7 | 0.9 |

Figure 3:
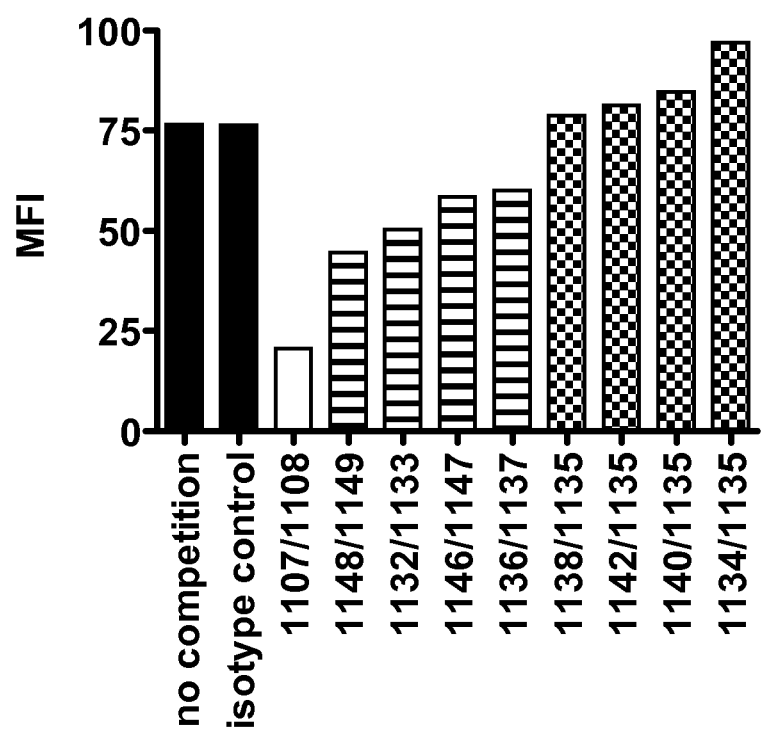
FIG. 3 shows the results of a assay which tested the ability of antibodies to compete with CD40L for binding to CD40. MFI=mean fluorescence intensity.

An epitope mapping experiment was performed in an assay which tested the ability of the antibodies to compete with CD40L for binding to CD40 on a cell surface. Wehi cells transfected with human CD40 were washed in FACS buffer (PBS, 0.5 FBS and 0.05% Sodium Azide) and pre-incubated with CD40 antibodies (25 µg/ml) or an isotype control (human IgG1, 25 µg/ml) for 30 min at +4° C. Human CD40L (0.5 µg/ml) was added to the cells without washing and incubated for 30 minutes at +4° C. The cells were washed and a secondary antibody anti-HA-PE, detecting CD40L, was added for another 15 minutes. The cells were washed three times before FACS analyses. The results are shown in FIG. 3. Solid black bars indicate no competition, open bar indicates strong competition, horizontally striped bar indicate medium competition, dotted black bars indicate low or no competition with CD40L for the target CD40 by the antibody clones.

The CD40 antibodies can be divided into three groups or classes with different binding profiles to the CD40 receptor, based on their capacity to compete with CD40L as illustrated in FIG. 3.

The first class of antibody clones, designated CDRH3A, includes the 1107/1108 clone. Antibodies in this class completely block binding of CD40L to CD40. They bind an epitope close to the CD40L binding site, and/or bind to CD40 in a way that affects the CD40L binding site on CD40 by inducing conformational changes.

The second class of antibody clones, designated CDRH3B, includes 1140/1135, 1138/1135, 1134/1135, 1142/1135. The antibodies in this class do not block CD40L binding to CD40, and thus bind to a separate epitope distinct from the CD40L binding site and the CDRH3A class. The CDRH3B class share a common CDRH3 length of 12 amino acids, and a consensus loop sequence of: A, R, G, P, F/V/A, Y, S, S/T, V/Y/F, F/I/L, D, Y (SEQ ID NO: 109). Moreover, the CDRH3B class have the CDRL3 and CDRH1 regions in common.

The third class of antibody clones, designated CDRH3C, includes 1148/1149, 1132/1133, 1146/1147, and 1136/1137. The antibodies in this class exhibit medium competition with CD40L, and bind an epitope partly overlapping with that of CD40L or partly affect the CD40L binding to CD40 by inducing conformational changes. This class have a consensus sequence in CDRH3, containing a FG motif. The consensus amino acids, in positions 105-117, are A, R, A/Y/R, V, -/N, F, G, F/M/I, D, Y (SEQ ID NO: 110). The consensus CDRH3 loop size is 9 amino acids.

Thus, each of the three CDRH3A-C classes represents advantageous properties of CD40 binding which may complement each other.

Example 4—In Vivo Effects of Anti-CD40 Antibody Administered by Different Routes This study investigated the the extent of activation of dendritic cells following intratumoural (local) versus intraperitoneal (systemic) administration of a single low dose of anti-CD40 antibody to mice with established tumours. The activation effect was assessed in tumours of a size of 220 mm³+/−100 (SD) mm².

MB49 bladder cancer cells were used to initiate tumors on 8-week-old female C57BL/6 mice (Taconic). On day 0, $0.25 \times 10^6$ tumor cells were inoculated subcutaneously into the right flank of the mouse. On day 14, mice were injected either intratumorally or intraperitoneally with anti-CD40 antibody FGK45 purchased from BioXcell (total of 1 µg, 30 µg of antibody per mouse, or untreated; 4 mice per group). On day 16, the mice were sacrificed by cervical dislocation. Tumor-draining lymph nodes were collected into full media, and two tumors or lymph nodes from each experimental group were pooled together.

Figure 4:
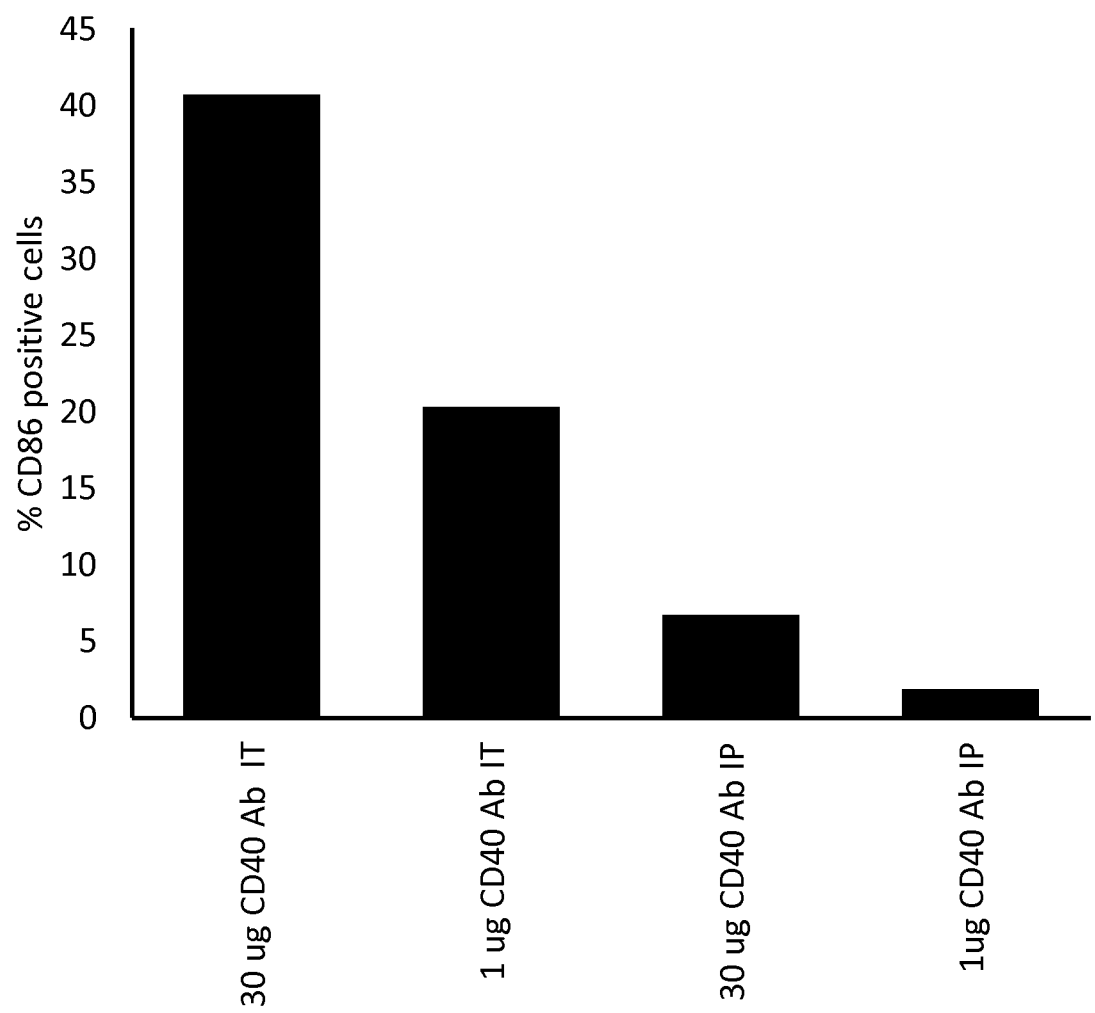
FIG. 4 shows the results of an assay for the activation of dendritic cells in the draining lymph nodes after different modes of administration of an anti-CD40 antibody in a mouse tumour model. Intratumoral administration (IT), intraperitoneal administration (IP). Activation is indicated by CD86 expression level, measured by mean fluorescent intensity (MFI).

Collected tissue was homogenized enzymatically and mechanically using Liberase™ TL (Roche) and nylon net filters (100 µm; Fischer Scientific). Membrane was thoroughly washed with RPMI media containing 3-10 mM EDTA and 0.1% fetal calf serum to prepare single-cell suspensions. Isolated cells were washed in PBS containing 0.5% bovine serum albumin, and unspecific Fc-binding was blocked by treating cells with mouse IgG (Sigma Aldrich). Cells were stained with anti-CD86-APC antibodies (BD Pharmingen) diluted 1:100, or with appropriate isotype-matched control antibodies (BD Pharmingen and Serotec). Stained murine spleen cells were used for compensation. Stained cells were analyzed by flow cytometry using FAC-Scalibur™ (Becton Dickinson) and CellQuest™ analysis software. The readout was the percentage of activated dendritic cells in the tumor draining lymph nodes measured 2 days after antibody injection, measured by determining the percentage of CD86 positive cells present. The % CD86 cells obtained from tumor draining lymph nodes of untreated mice was subtracted (background subtraction). The results are shown in FIG. 4.

The results suggest that intratumoral treatment produced a more than 30-fold increase in response. This was an unexpected result, in that there was a far greater difference between local and systemic administration than has been previously reported. The higher activation of dendritic cells in draining lymph nodes of tumour bearing animals suggests surprisingly increased potency and efficacy for local administration of anti-CD40 antibodies. Moreover, it suggests that a single low dose of 0.04 mg/kg anti-CD40 agonistic antibody will constitute a therapeutic dose if locally administered. The maximal obtained tumor concentration of the CD40 antibody in this experiment was 5 µg/ml (1/0.220) (assuming that the antibody does not leak out of the tumor).

This suggests that the therapeutic dose could be as low as 5 µg in man for treatment of a 1 cm³ tumor.

Example 5—Evaluation of Cross-Reactivity with Monkey CD40

The ability of the anti-CD40 antibodies to bind to monkey CD40 was assessed by measuring binding to HEK cells expressing cynomolgus CD40 on the cell surface.

HEK cells were transfected with 1 or 10 µg/ml cynomolgus CD40 inserted in the pcDNA 3.1 vector. Transfected cells were sorted by FACS. Binding to cynomolgus CD40 of the CD40 antibody clones was analyzed and compared to non-specific binding to HEK empty vector. Five of the assayed CD40 antibody clones were cross reactive with monkey CD40. The results are summarized in Table 6 which follows.

TABLE 6

| CD40 antibody clone | Cynomolgus monkey cross reactivity |
|---|---|
| 1107/1108 | + |
| 1132/1133 | + |
| 1140/1135 | + |
| 1150/1151 | + |
| 1134/1135 | + |

Example 6—Determination of Affinity Constants for the Anti-CD40 Antibodies by Surface Plasmon Resonance The affinity constants of purified antibodies were assessed by surface plasmon resonance using the Biacore™ 3000 instrument according to manufacturer's protocols. CD40hfc (R&Dsystems, USA) was immobilized to the BIAcore™ sensorchip, CM5, using conventional amine coupling. Association was followed for 3 minutes and dissociation for 12 minutes. Regeneration was performed twice using 50 mM NaOH for 30 seconds. The kinetic parameters and the affinity constants were calculated using BIAevaluation 4.1 software. The CD40 antibody clones were run over the sensor at a flow rate of 30 µl/min in HBS-P (GE, BR-1003-68) at concentration ranges between 1-100 or 1-300 nM and analyzed using 1:1 Langmuir with drifting baseline.

The affinity constant (KD) for binding to CD40 for each of the antibodies was shown to be in the range 1-10 nM. The association rate (ka) for each of the antibodies was in the range $0.4$-$3.4 \times 10^6$ 1/M. The dissociation rate (kd) for each of the antibodies was in the range $1$-$10 \times 10^{-3}$ 1/s. The results are shown Table 7 which follows.

TABLE 7

| CD40 antibody | ka (1/M) | kd (1/s) | KD (M) |
|---|---|---|---|
| 1107/1108 | $1.0 \times 10{+}06$ | $1.3 \times 10{-}03$ | $1.3 \times 10{-}09$ |
| 1132/1133 | $3.4 \times 10{+}06$ | $8.1 \times 10{-}03$ | $2.4 \times 10{-}09$ |
| 1134/1135 | $4.0 \times 10{+}05$ | $1.4 \times 10{-}03$ | $3.4 \times 10{-}09$ |
| 1136/1137 | $8.7 \times 10{+}05$ | $9.5 \times 10{-}03$ | $1.1 \times 10{-}08$ |
| 1140/1135 | $1.1 \times 10{+}06$ | $4.3 \times 10{-}03$ | $3.9 \times 10{-}09$ |
| 1150/1151 | $2.2 \times 10{+}06$ | $3.4 \times 10{-}03$ | $1.5 \times 10{-}09$ |

Example 7—Activation of Monocyte Derived Dendritic Cells

CD14 positive cells were obtained by positive selection from human peripheral blood mononuclear cells using magnetic beads (Miltenyi Biotech Norden AB, Lund, Sweden, 130-050-201). Monocyte derived dendritic cells (moDCs) were matured from CD14 positive cells by stimulation with 150 ng/ml GM-CSF (Life Technologies, cat no # PHC2011) and 50 ng/ml IL-4 (Life Technologies, Cat no # PHC0045) for 6 days. The monocyte derived dendritic cells were stimulated with test antibodies or control for 48 h. Supernatants were collected and DC activation was analyzed as increased production of IL12p40 with ELISA (BD Biosciences, Cat no #555171). The DC activation index was calculated by dividing the IL-12p40 levels obtained with the test antibodies at 10 µg/mL or 33 µg/ml with the IL-12p40 levels obtained with an isotype control at the corresponding concentrations.

DC activation was assessed for three test antibodies. Antibodies 1150/1151, 1107/1108 and 1132/1133 were shown to have good DC activation properties. Results are also shown in summary Table 9.

Example 8—Chimeric Domain Mapping

The extracellular part of CD40 consists of four domains, where each domain can be subdivided into two modules. By exchanging domains or modules in the human CD40 receptor with the corresponding murine CD40 sequence, functional chimeric receptors can be expressed. None of the antibodies tested in this assay bind to murine CD40. Thus, by identifying which chimeric constructs a test antibody is not able to bind to, the binding domain, or binding module(s) of each antibody in human CD40 can be identified. If two antibodies share the same pattern of binding to the different chimeras, this means that they depend on the same modules or domains of CD40 for binding.

Genes of CD40 human/mouse chimeras were synthesized (GenScript®). The different chimeras were designed by exchanging domains or modules of the human CD40 with corresponding mouse CD40 domains or modules. The chimeras were designed after evaluation of the human and mouse sequences and 3D analysis of human CD40. The constructs were cloned into pcDNA3.1 vector (Invitrogen) using the restriction sites for NotI and HindIII. The mouse/human chimeras were transiently transfected into FreeStyle™ 293-F cells (Invitrogen), incubated 48 hours in FreeStyle™ 293 expression medium (Invitrogen) 37 C, 8% CO2, 135 rpm. Expression was confirmed with polyclonal human or mouse CD40 antibodies.

The transfected cells were incubated with test anti-CD40 antibodies, human CD40L (hCD40L, RnD Systems), mouse CD40L (mCD40L, RnD Systems) and controls for 30 min 4° C. and then detected with a-huIgG-PE (Jackson Immunoresearch) 30 min 4° C. Cells were analyzed with FACSVerse™ (BD Biosciences). Binding to the different chimeric constructs were determined with MFI to be either positive (+) or negative (−). Results are shown in Table 9.

None of the tested anti-human CD40 antibodies bound to murine CD40. The tested antibodies bound to at least three distinct epitopes. The first epitope is located in module B of domain 1 of CD40 (positions 38-59) and is referred to as D1B when indicating "CD40 epitope" for the antibodies in summary Table 9. Antibodies binding to this epitope include 1132/1133 and 1150/1151. The second epitope is located in module A of domain 2 of CD40 (positions 62-77) and is referred to as D2A in summary Table 9. Antibodies binding to this epitope include 1107/1108. The third epitope is located in module B of domain 3 (positions 122-143) of CD40 and is referred to as D3B in summary Table 9. Antibodies binding to this epitope include 1140/1135.

TABLE 8

| Chimeric Construct and name | Construct description (amino acid sequence for mouse sequence in parenthesis) | CD40 antibody clones | | | |
|---|---|---|---|---|---|
| | | 1107/ 1108 | 1132/ 1133 | 1140/ 1135 | 1150/ 1151 |
| CD40 cys1 mouse | Human CD40 with mouse domain 1 (25-60) | + | − | + | − |
| CD40 cys2 mouse | Human CD40 with mouse domain 2 (61-103) | − | + | + | + |
| CD40 cys3 mouse | Human CD40 with mouse domain 3 (104-144) | + | + | − | + |
| CD40 cys4 mouse | Human CD40 with mouse domain 4 (145-187) | + | + | + | + |
| CD40 cys1A mouse | Human CD40 with mouse module A of domain 1 (26-37) | + | + | + | + |
| CD40 cys1B mouse | Human CD40 with mouse module B of domain 1 (38-59) | + | − | + | − |
| CD40 cys2A mouse | Human CD40 with mouse module A of domain 2 (62-77) | − | + | + | + |
| CD40 cys2B mouse | Human CD40 with mouse module B of domain 2 (80-103) | + | + | + | + |
| CD40 cys3A mouse | Human CD40 with mouse module A of domain 3 (105-119) | + | + | + | + |
| CD40 cys3B mouse | Human CD40 with mouse module B of domain 3 (122-143) | + | + | − | + |
| CD40 cys4A mouse | Human CD40 with mouse module A of domain 4 (146-161) | + | + | + | + |
| CD40 cys4B mouse | Human CD40 with mouse module B of domain 4 (164-186) | + | + | + | + |

The D1B, D2A and D3B epitopes were further assessed by carrying out a detailed comparison of the sequences of human and murine CD40 in the relevant regions of each protein. This comparison is shown below.

```
CD40 Positon 38-59 (D1B)
CSLCQPGQKLVSDCTEFTETEC - HUMAN     (SEQ ID NO: 111)
CDLCQPGSRLTSHCTALEKTQC - MOUSE     (SEQ ID NO: 112)

CD40 Position 62-77 (D2A)
CGESEFLDTWNRETHC - HUMAN           (SEQ ID NO: 113)
CDSGEFSAQWNREIRC - MOUSE           (SEQ ID NO: 114)

CD40 Positon 122-143 (D3B)
HRSCSPGFGVKQIATGVSDTIC - HUMAN     (SEQ ID NO: 115)
HTPCIPGFGVMEMATETTDTVC - MOUSE     (SEQ ID NO: 116)
```

The results of the binding experiment in this Example indicate that, when all of the residues in bold in a particular human CD40 domain are replaced with the corresponding murine amino acids, antibodies designated to bind to that particular domain lose their ability to bind. Some or all of these particular residues are therefore required for these antibodies to bind CD40.

The following Table 9 summarises the in vitro properties of the anti-CD40 antibodies tested in the preceding Examples.

TABLE 9

| In vitro property | 1150/1151 | 1107/1108 | 1146/1147 | 1148/1149 | 1132/1133 |
|---|---|---|---|---|---|
| CD40L blocking (see Example 3) | − | ++ | + | + | + |
| CDRH3 class (see Example 3) | B | A | C | C | C |
| CD40 epitope (see Example 8) | D1B | D2A | NT | NT | D1B |
| Affinity KD (M) × $10^{-9}$ (see Example 6) | 1.5 | 1.3 | NT | NT | 2.4 |
| On rate (ka) 1/Ms × $10^6$ (see Example 6) | 2.2 | 1 | NT | NT | 3.4 |
| Off rate (kd) 1/s × $10^{-3}$ (see Example 6) | 3.4 | 1.3 | NT | NT | 8.1 |
| B cell proliferation (see Example 3) | 0.9 | 0.7 | 3.6 | 2.3 | 2.2 |
| CD40 Binding ELISA EC50 (ng/ml) (see Example 3) | 41 | 34 | 580 | 2200 | 280 |
| Cynomolgus cross-reactivity (see Example 5) | Yes | Yes | NT | NT | Yes |
| DC activation (see Example 7) | 7.8 | 22.3 | NT | NT | 10.8 |

| In vitro property | 1136/1137 | 1138/1135 | 1142/1135 | 1140/1135 | 1134/1135 |
|---|---|---|---|---|---|
| CD40L blocking | + | − | − | − | − |
| CDRH3 class | C | B | B | B | B |
| CD40 epitope | NT | NT | NT | D3B | NT |
| Affinity KD (M) × $10^{-9}$ | 11 | NT | NT | 3.9 | 3.4 |
| On rate (ka) 1/Ms × $10^6$ | 0.9 | NT | NT | 1.1 | 0.4 |
| Off rate (kd) 1/s × $10^{-3}$ | 9.5 | NT | NT | 4.3 | 1.4 |
| B cell proliferation | 1.0 | 4.5 | 1.5 | 0.4 | 1.0 |
| CD40 Binding ELISA EC50 (ng/ml) | 1400 | 970 | 560 | 310 | 25 |
| Cynomolgus cross-reactivity | NT | NT | NT | Yes | Yes |
| DC activation | NT | NT | NT | NT | NT |

Example 9—In Vivo Activation of Tumor Infiltrating Myeloid Cells, Including Dendritic Cells, by Anti-CD40 Antibodies Administered by Different Routes MB49 bladder cancer cells were used to initiate tumors on 8-week-old female hCD40Tg mice (bred in-house). On day 0, $0.25 \times 10^6$ tumor cells were inoculated subcutaneously into the right flank of the mouse. On day 14, mice were injected either intratumorally or intraperitoneally with a test anti-CD40 antibody (total of 1 ug and 30 ug of antibody per mouse, or PBS; 4 mice per group). On day 16, 40 mice were sacrificed by cervical dislocation. Tumor-draining lymph nodes were collected into full media, and two tumors or lymph nodes from each experimental group were pooled together. Collected tissue was homogenized enzymatically and mechanically using Liberase™ TL (Roche) and nylon net filters (100 μm; Fischer Scientific). Membranes were thoroughly washed with RPMI media containing 3-10 mM EDTA and 0.1% fetal calf serum to prepare single-cell suspensions. Isolated cells were washed in PBS containing 0.5% bovine serum albumin, and unspecific Fc-binding was blocked by treating cells with mouse anti-CD16/32 (BD Bioscience).

CD86 expression levels (as a marker for activation) were separately analysed on CD11c-positive cells and CD11b-positive cells by flow cytometry. CD11c is a marker for dendritic cells. CD11b is expressed on monocytes, macrophages and subsets of dendritic cells. Cells were stained with the live/dead fixable stain FVS450 (BD Bioscience) and antibodies specific for CD11c-PE, CD11b-PECy7 and CD86-APC (BD Bioscience) diluted 1:100. After staining all cells were paraformaldehyde fixed using Cellfix (BD Bioscience). Staining for each sample was measured and calculated as CD86 (sample)−FMO (sample) and presented as % positive cells minus PBS control. Stained cells were analyzed using FACSVerse™ (Becton Dickinson) and FlowJo vX analysis software. The results are shown in FIGS. 5 (CD11c cells) and 6 (CD11b cells).

Figure 5:
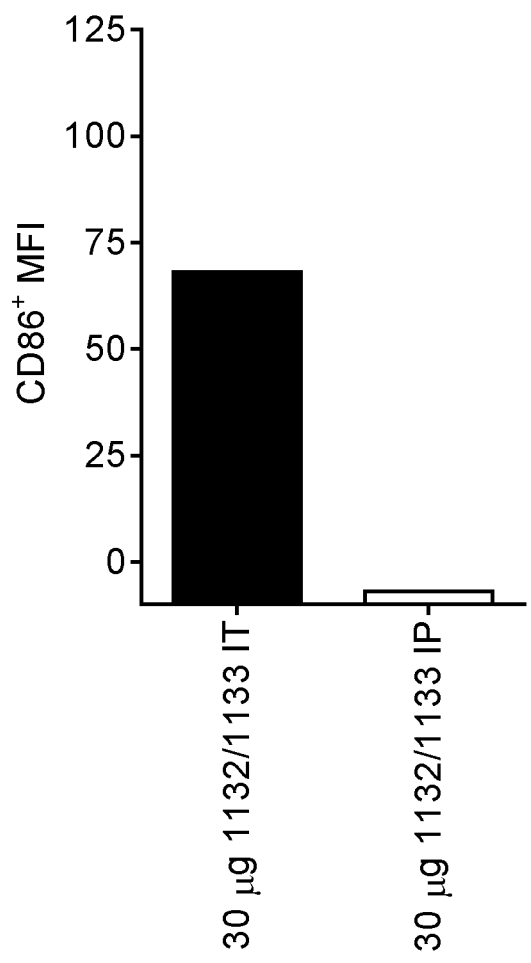
FIG. 5 shows the results of an assay for the activation of CD11c positive cells in the draining lymph nodes after different modes of administration of an anti-CD40 antibody in a mouse tumour model. Intratumoral administration (IT), intraperitoneal administration (IP). Activation is indicated by CD86 expression level, measured by mean fluorescent intensity (MFI).
Figure 6:
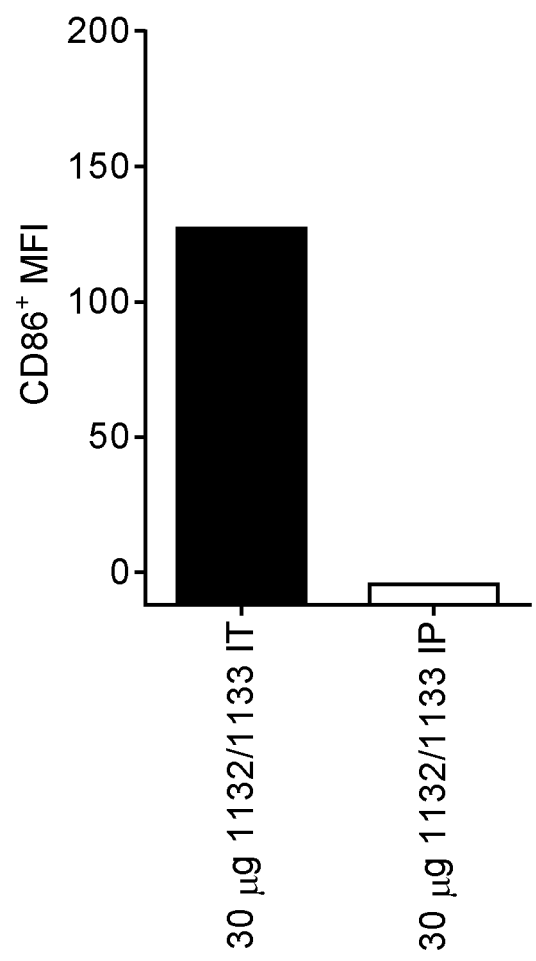
FIG. 6 shows shows the results of an assay for the activation of CD11b positive cells in the draining lymph nodes after different modes of administration of an anti-CD40 antibody in a mouse tumour model. Intratumoral administration (IT), intraperitoneal administration (IP). Activation is indicated by CD86 expression level, measured by mean fluorescent intensity (MFI).

The data in FIG. 5 show that treatment with anti-CD40 antibody increased the activation of dendritic cells measured by CD86 expression in the tumor. Overall, a stronger activation of dendritic cells in the tumor is obtained following intratumoral (IT) treatment compared to intraperitoneal (IP) treatment. The data in FIG. 6 shows that treatment with anti-CD40 antibody increased the activation of CD11b positive cells measured by CD86 expression in the tumor. Overall, a stronger activation of CD11b positive cells in the tumor is obtained following intratumoral (IT) treatment compared to intraperitoneal (IP) treatment.

Example 10—In Vivo Anti-Tumor Effect in Bladder Cancer Model

Figure 7:
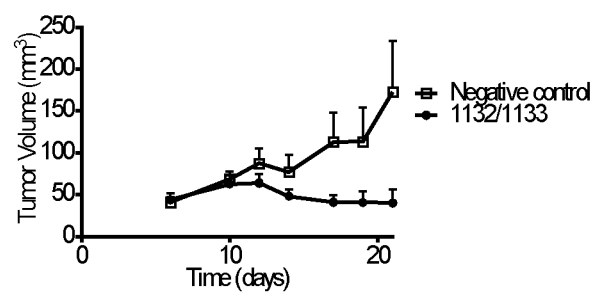
FIG. 7 shows the change in tumour volume over time in a mouse tumour model following treatment with anti-CD40 antibodies as shown, relative to an isotype control.
Figure 7:
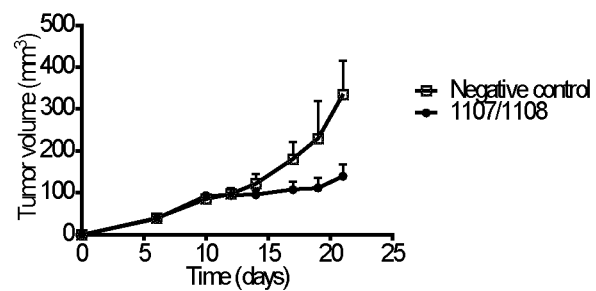
Figure 7:
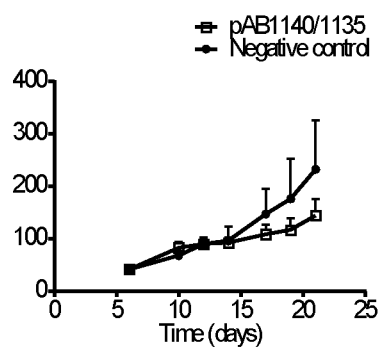
Figure 8:
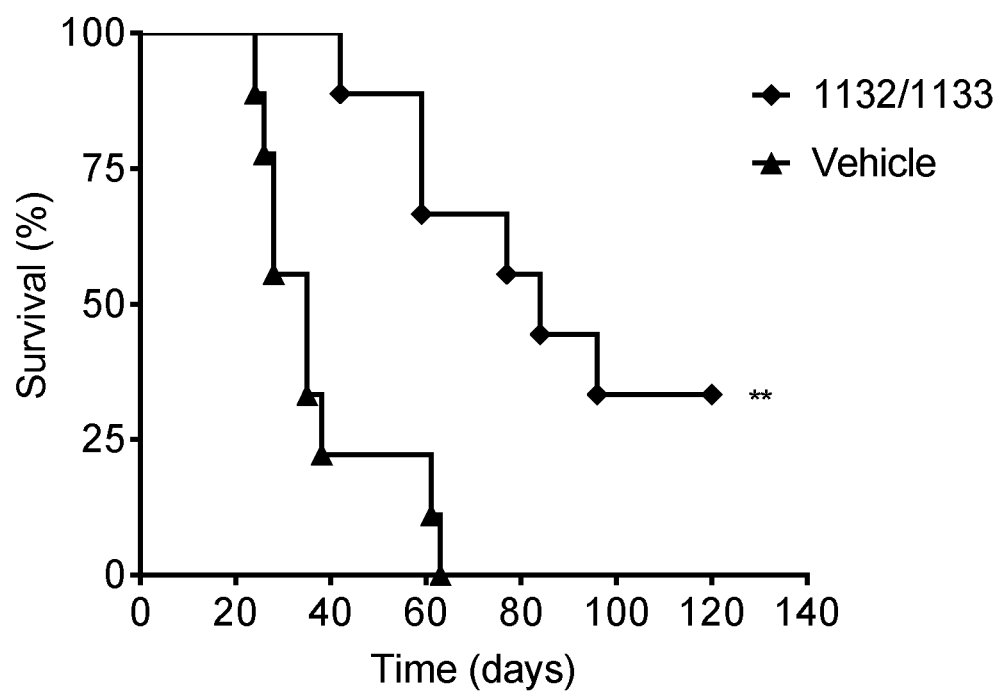
FIG. 8 shows survival over time in a mouse tumour model treated with CD40 antibody clone 1132/1133 (**, $p<0.01$). A significant survival for treated animals is observed relative to control.

Anti-CD40 antibodies were studied for anti-tumor activity in vivo in established MB49 murine bladder cell carcinoma cancer in human CD40 transgenic mice. MB49 bladder cancer cells ($2.5 \times 10^5$) were inoculated by injection of $2.5 \times 10^5$ cells in the flank at day 0, and the tumors were treated peritumorally with 30 μg antibody or an appropriate isotype control at day 7 and 10. Tumor growth and survival was followed over time, with tumor volumes measured at days 14, 17, 19 and 21. Tumor measurements (width, height, length) were taken by caliper and tumour volume calculated by the formular $w/2 \times l/2 \times h/2 \times pi \times (4/3)$. The animals were terminated before the tumor volume reached 2 cm$^3$, at tumor wounding, or when the health of the animal was affected. Relative tumor volumes were determined by calculating Treated/Control (T/C)=100×(mean tumor volume of the treated group)/(mean tumor volume of isotype control treated group). Results are shown in Table 10. Changes in tumour volume are shown in FIG. 7. Survival rates for mice treated with 1132/1133 versus control are shown in FIG. 8.

In summary, the tested antibodies 1132/1133, 1107/1108, and 1140/1135 showed anti-tumor activity. 1132/1133 and 1107/1108 generated significant anti-tumor activity vs. control (students t test).

TABLE 10

|  |  | D14 | D17 | D19 | D21 |
|---|---|---|---|---|---|
| Control | Mean | 77 | 113 | 114 | 173 |
|  | T/C | 100% | 100% | 100% | 100% |
| 1132/1133 | Mean | 48 | 41 | 41 | 40 |
|  | T/C | 63% | 36% | 36% | 23% |
| Control | Mean | 123 | 181 | 230 | 336 |
|  | T/C | 100% | 100% | 100% | 100% |
| 1107/1108 | Mean | 95 | 108 | 111 | 140 |
|  | T/C | 78% | 60% | 48% | 42% |
| Control | Mean | 96 | 147 | 176 | 232 |
|  | T/C | 100% | 100% | 100% | 100% |
| 1140/1135 | Mean | 92 | 109 | 117 | 144 |
|  | T/C | 96% | 74% | 66% | 62% |

Example 11—CD40 Antibodies Establish Anti-Tumor Immunological Memory In Vivo Mice previously treated for bladder cancer and cured with CD40 antibodies 1140/1135, 1132/1132 or 1107/1108 were re-challenged with bladder cancer cells. The treatment with CD40 antibodies was shown to have established an immunological memory for bladder cancer and hence immunity to tumors when the animals were re-challenged.

For this experiment, MB49 re-challenge was performed by injection of $2.5 \times 10^5$ cells in the flank of hCD40tg mice that had previously been cured of MB49 tumors by treatment with CD40 antibodies 1140/1135, 1132/1132 or 1107/1108 (as in Example 10). Naïve (i.e. not previously treated with CD40 antibodies or inoculated with tumor cells) hCD40tg mice were used as controls. Tumor growth was measured by caliper and survival was followed over time as in Example 10.

Figure 9:
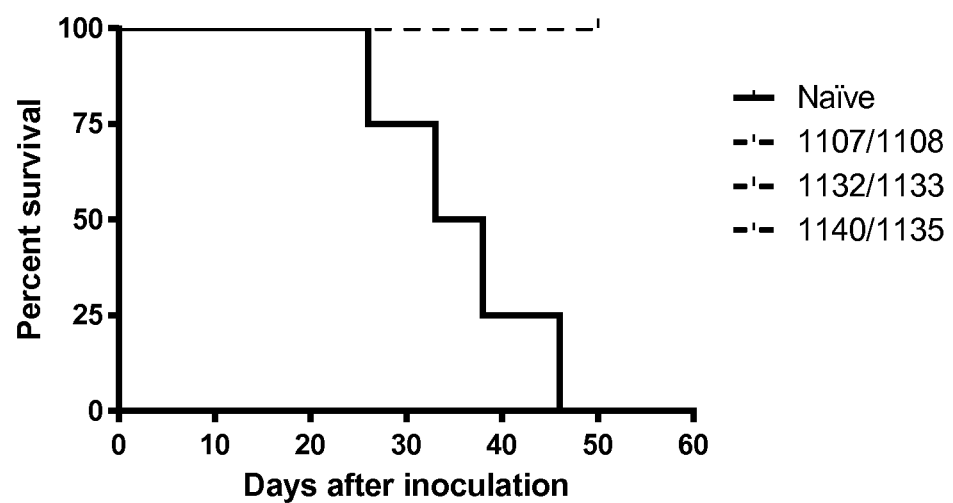
FIG. 9 shows survival over time in a model in which mice previously cured of tumour by anti-CD40 antibody treatment were re-challenged with tumour cells, as compared to naive mice (not previously challenged or treated). Immunological memory is present in the mice previously treated with anti-CD40.

As shown in FIG. 9, the previously treated, re-challenged mice had 100% survival and very low/zero tumor volume. Thus, the data shows that treatment with the CD40 antibodies induces immunity to tumor re-challenge with MB49 in hCD40tg mice. This demonstrates the presence of immunological memory. This result is significant, since such anti-tumour immunological memory is necessary to establish a long lasting treatment effect particularly against metastatic tumors Example 12—Summary of Sequence Information For each antibody described below, CDRs are underlined in the amino acid sequences. CDRs were identified using the IMGT® numbering system (www.imgt.org)

Antibody 1146/1147

Variable heavy chain (V_H) amino acid sequence
SEQ ID NO: 61
EVQLLESGGGLVQPGGSLRLSCAAS<u>GFTFSSYA</u>MSWVRQAPGKGLEWVS A<u>ISGSGGST</u>YYADSVKGRFTISRDNSKNTLYLQMNSLRAEDTAVYYCARR

VFGFDYWGQGTLVTVSS

Variable light chain (V_L) amino acid sequence
SEQ ID NO: 62
DIQMTQSPSSLSASVGDRVTITCRAS<u>QSISSY</u>LNWYQQKPGKAPKLLIY<u>A</u>

<u>AS</u>SLQSGVPSRFSGSGSGTDFTLTISSLQPEDFATYYC<u>QQYYYYPFT</u>FGQ

GTKLEIK

CDR amino acid sequences
V_H CDRs: CDR1: GFTFSSYA [SEQ ID NO: 1]
         CDR2: ISGSGGST [SEQ ID NO: 2]
         CDR3: ARRVFGFDY [SEQ ID NO: 3]

V_L CDRs: CDR1: QSISSY [SEQ ID NO: 4]
         CDR2: AAS [SEQ ID NO: 5]
         CDR3: QQYYYYPFT [SEQ ID NO: 6]

Variable heavy chain (V_H) nucleotide sequence
SEQ ID NO: 81
GAGGTGCAGCTGTTGGAGAGCGGGGGAGGCTTGGTACAGCCTGGGGGT

CCCTGCGCCTCTCCTGTGCAGCCAGCGGATTCACCTTTAGCAGCTATGC

CATGAGCTGGGTCCGCCAGGCTCCAGGGAAGGGGCTGGAGTGGGTCTCA

GCTATTAGTGGTAGTGGTGGTAGCACATACTATGCAGACTCCGTGAAGGG

CCGGTTCACCATCTCCCGTGACAATTCCAAGAACACGCTGTATCTGCAAA

TGAACAGCCTGCGTGCCGAGGACACGGCTGTATATTATTGTGCGCGCCG

TGTTTTCGGTTTTGACTATTGGGGCCAGGGAACCCTGGTCACCGTCTCC

TCA

Variable light chain (V_L) nucleotide sequence
SEQ ID NO: 82
GACATCCAGATGACCCAGTCTCCATCCTCCCTGAGCGCATCTGTAGGAG

ACCGCGTCACCATCACTTGCCGGGCAAGTCAGAGCATTAGCAGCTATTT

AAATTGGTATCAGCAGAAACCAGGGAAAGCCCCTAAGCTCCTGATCTAT

GCTGCATCCAGTTTGCAAAGTGGGGTCCCATCACGTTTCAGTGGCAGTG

GAAGCGGGACAGATTTCACTCTCACCATCAGCAGTCTGCAACCTGAAG

ATTTTGCAACTTATTACTGTCAACAGTACTACTACTACCCGTTCACTTTT

GGCCAGGGGACCAAGCTGGAGATCAAA

Antibody 1142/1135

Variable heavy chain (V_H) amino acid sequence
SEQ ID NO: 63
EVQLLESGGGLVQPGGSLRLSCAAS<u>GFTFSSYA</u>MSWVRQAPGKGLEWVS A<u>ISGSGGST</u>YYADSVKGRFTISRDNSKNTLYLQMNSLRAEDTAVYYC<u>AR</u>

<u>GPAYSTVLDY</u>WGQGTLVTVSS

Variable light chain (V_L) amino acid sequence
SEQ ID NO: 64
DIQMTQSPSSLSASVGDRVTITCRAS<u>QSISSY</u>LNWYQQKPGKAPKLLIY<u>A</u>

<u>AS</u>SLQSGVPSRFSGSGSGTDFTLTISSLQPEDFATYYC<u>QQSYSTPYT</u>FGQ

GTKLEIK

CDR amino acid sequences
V_H CDRs: CDR1: GFTFSSYA [SEQ ID NO: 7]
         CDR2: ISGSGGST [SEQ ID NO: 8]
         CDR3: ARGPAYSTVLDY [SEQ ID NO: 9]

V_L CDRs: CDR1: QSISSY [SEQ ID NO: 10]
         CDR2: AAS [SEQ ID NO: 11]
         CDR3: QQSYSTPYT [SEQ ID NO: 12]

Variable heavy chain (V_H) nucleotide sequence
SEQ ID NO: 83
GAGGTGCAGCTGTTGGAGAGCGGGGGAGGCTTGGTACAGCCTGGGGGG

TCCCTGCGCCTCTCCTGTGCAGCCAGCGGATTCACCTTTAGCAGCTATG

CCATGAGCTGGGTCCGCCAGGCTCCAGGGAAGGGGCTGGAGTGGGTCT

CAGCTATTAGTGGTAGTGGTGGTAGCACATACTATGCAGACTCCGTGAA

GGGCCGGTTCACCATCTCCCGTGACAATTCCAAGAACACGCTGTATCTG

CAAATGAACAGCCTGCGTGCCGAGGACACGGCTGTATATTATTGTGCGC

GCGGTCCGGCTTACTCTACTGTTTTGGACTATTGGGGCCAGGGAACCC

TGGTCACCGTCTCCTCA

Variable light chain (V_L) nucleotide sequence
SEQ ID NO: 84
GACATCCAGATGACCCAGTCTCCATCCTCCCTGAGCGCATCTGTAGGA

GACCGCGTCACCATCACTTGCCGGGCAAGTCAGAGCATTAGCAGCTAT

TTAAATTGGTATCAGCAGAAACCAGGGAAAGCCCCTAAGCTCCTGATCT

ATGCTGCATCCAGTTTGCAAAGTGGGGTCCCATCACGTTTCAGTGGCAG

TGGAAGCGGGACAGATTTCACTCTCACCATCAGCAGTCTGCAACCTGA

AGATTTTGCAACTTATTACTGTCAACAGAGTTACAGTACCCCTTATACTT

TTGGCCAGGGGACCAAGCTGGAGATCAAA

Antibody 1132/1133

Variable heavy chain (V_H) amino acid sequence
SEQ ID NO: 65
EVQLLESGGGLVQPGGSLRLSCAAS<u>GFTFSSYA</u>MSWVRQAPGKGLEWVS G<u>IGSYGGGT</u>YYADSVKGRFTISRDNSKNTLYLQMNSLRAEDTAVYYC<u>AR</u>

<u>YVNFGMDY</u>WGQGTLVTVSS

Variable light chain (V_L) amino acid sequence
SEQ ID NO: 66
DIQMTQSPSSLSASVGDRVTITCRAS<u>QSISSY</u>LNWYQQKPGKAPKLLIY <u>AAS</u>SLQSGVPSRFSGSGSGTDFTLTISSLQPEDFATYYC<u>QQYGRNPPT</u>

FGQGTKLEIK

CDR amino acid sequences
V_H CDRs: CDR1: GFTFSSYA [SEQ ID NO: 13]
         CDR2: IGSYGGGT [SEQ ID NO: 14]
         CDR3: ARYVNFGMDY [SEQ ID NO: 15]

V_L CDRs: CDR1: QSISSY [SEQ ID NO: 16]
         CDR2: AAS [SEQ ID NO: 17]
         CDR3: QQYGRNPPT [SEQ ID NO: 18]

-continued
Variable heavy chain (V<sub>H</sub>) nucleotide sequence
SEQ ID NO: 85
GAGGTGCAGCTGTTGGAGAGCGGGGGAGGCTTGGTACAGCCTGGGGGG

TCCCTGCGCCTCTCCTGTGCAGCCAGCGGATTCACCTTTAGCAGCTATG

CCATGAGCTGGGTCCGCCAGGCTCCAGGGAAGGGGCTGGAGTGGGTCT

CAGGTATTGGTTCTTACGGTGGTGGTACATACTATGCAGACTCCGTGAAG

GGCCGGTTCACCATCTCCCGTGACAATTCCAAGAACACGCTGTATCTGCA

AATGAACAGCCTGCGTGCCGAGGACACGGCTGTATATTATTGTGCGCGC

TACGTTAACTTCGGTATGGACTATTGGGGCCAGGGAACCCTGGTCACCG

TCTCCTCA

Variable light chain (V<sub>L</sub>) nucleotide sequence
SEQ ID NO: 86
GACATCCAGATGACCCAGTCTCCATCCTCCCTGAGCGCATCTGTAGGAG

ACCGCGTCACCATCACTTGCCGGGCAAGTCAGAGCATTAGCAGCTATTT

AAATTGGTATCAGCAGAAACCAGGGAAAGCCCCTAAGCTCCTGATCTA

TGCTGCATCCAGTTTGCAAAGTGGGGTCCCATCACGTTTCAGTGGCAGT

GGAAGCGGGACAGATTTCACTCTCACCATCAGCAGTCTGCAACCTGAA

GATTTTGCAACTTATTACTGTCAACAGTACGGTCGTAACCCGCCCACTTT

TGGCCAGGGGACCAAGCTGGAGATCAAA

Antibody 1148/1149

Variable heavy chain (V<sub>H</sub>) amino acid sequence
SEQ ID NO: 67
EVQLLESGGGLVQPGGSLRLSCAAS<u>GFTFSSYA</u>MSWVRQAPGKGLEWVS A<u>ISGSGGST</u>YYADSVKGRFTISRDNSKNTLYLQMNSLRAEDTAVYYC<u>AR</u>

<u>AVFGFDY</u>WGQGTLVTVSS

Variable light chain (V<sub>L</sub>) amino acid sequence
SEQ ID NO: 68
DIQMTQSPSSLSASVGDRVTITCRAS<u>QSISSY</u>LNWYQQKPGKAPKLLIY <u>AAS</u>SLQSGVPSRFSGSGSGTDFTLTISSLQPEDFATYYC<u>QQAYYFPHT</u>F

GQGTKLEIK

CDR amino acid sequences
V<sub>H</sub> CDRs: CDR1:  GFTFSSYA [SEQ ID NO: 19]
        CDR2:  ISGSGGST [SEQ ID NO: 20]
        CDR3:  ARAVFGFDY [SEQ ID NO: 21]

V<sub>L</sub> CDRs: CDR1:  QSISSY [SEQ ID NO: 22]
        CDR2:  AAS [SEQ ID NO: 23]
        CDR3:  QQAYYFPHT [SEQ ID NO: 24]

Variable heavy chain (V<sub>H</sub>) nucleotide sequence
SEQ ID NO: 87
GAGGTGCAGCTGTTGGAGAGCGGGGGAGGCTTGGTACAGCCTGGGGGG

TCCCTGCGCCTCTCCTGTGCAGCCAGCGGATTCACCTTTAGCAGCTATG

CCATGAGCTGGGTCCGCCAGGCTCCAGGGAAGGGGCTGGAGTGGGTCT

CAGCTATTAGTGGTAGTGGTGGTAGCACATACTATGCAGACTCCGTGAAG

GGCCGGTTCACCATCTCCCGTGACAATTCCAAGAACACGCTGTATCTG

CAAATGAACAGCCTGCGTGCCGAGGACACGGCTGTATATTATTGTGCG

CGCGCTGTTTTCGGTTTTGACTATTGGGGCCAGGGAACCCTGGTCACCG

TCTCCTCA

Variable light chain (V<sub>L</sub>) nucleotide sequence
SEQ ID NO: 88
GACATCCAGATGACCCAGTCTCCATCCTCCCTGAGCGCATCTGTAGGAG

ACCGCGTCACCATCACTTGCCGGGCAAGTCAGAGCATTAGCAGCTATTT

AAATTGGTATCAGCAGAAACCAGGGAAAGCCCCTAAGCTCCTGATCTAT

GCTGCATCCAGTTTGCAAAGTGGGGTCCCATCACGTTTCAGTGGCAGTG

GAAGCGGGACAGATTTCACTCTCACCATCAGCAGTCTGCAACCTGAAG

ATTTTGCAACTTATTACTGTCAACAGGCTTACTACTTCCCGCACACTTTT

GGCCAGGGGACCAAGCTGGAGATCAAA

Antibody 1138/1135

Variable heavy chain (V<sub>H</sub>) amino acid sequence
SEQ ID NO: 69
EVQLLESGGGLVQPGGSLRLSCAAS<u>GFTFSSYA</u>MSWVRQAPGKGLEWVS A<u>ISGSGGST</u>YYADSVKGRFTISRDNSKNTLYLQMNSLRAEDTAVYYC<u>AR</u>

<u>GFVYSSYIDY</u>WGQGTLVTVSS

Variable light chain (V<sub>L</sub>) amino acid sequence
SEQ ID NO: 70
DIQMTQSPSSLSASVGDRVTITCRAS<u>QSISSY</u>LNWYQQKPGKAPKLLIY <u>AAS</u>SLQSGVPSRFSGSGSGTDFTLTISSLQPEDFATYYC<u>QQSYSTPYT</u>

FGQGTKLEIK

CDR amino acid sequences
V<sub>H</sub> CDRs: CDR1:  GFTFSSYA [SEQ ID NO: 25]
        CDR2:  ISGSGGST [SEQ ID NO: 26]
        CDR3:  ARGFVYSSYIDY [SEQ ID NO: 27]

V<sub>L</sub> CDRs: CDR1:  QSISSY [SEQ ID NO: 28]
        CDR2:  AAS [SEQ ID NO: 29]
        CDR3:  QQSYSTPYT [SEQ ID NO: 30]

Variable heavy chain (V<sub>H</sub>) nucleotide sequence
SEQ ID NO: 89
GAGGTGCAGCTGTTGGAGAGCGGGGGAGGCTTGGTACAGCCTGGGGGG

TCCCTGCGCCTCTCCTGTGCAGCCAGCGGATTCACCTTTAGCAGCTATG

CCATGAGCTGGGTCCGCCAGGCTCCAGGGAAGGGGCTGGAGTGGGTCT

CAGCTATTAGTGGTAGTGGTGGTAGCACATACTATGCAGACTCCGTGAA

GGGCCGGTTCACCATCTCCCGTGACAATTCCAAGAACACGCTGTATCT

GCAAATGAACAGCCTGCGTGCCGAGGACACGGCTGTATATTATTGTGC

GCGCGGTTTCGTTTACTCTTCTTACATTGACTATTGGGGCCAGGGAACC

CTGGTCACCGTCTCCTCA

Variable light chain (V<sub>L</sub>) nucleotide sequence
SEQ ID NO: 90
GACATCCAGATGACCCAGTCTCCATCCTCCCTGAGCGCATCTGTAGGAG

ACCGCGTCACCATCACTTGCCGGGCAAGTCAGAGCATTAGCAGCTATTT

AAATTGGTATCAGCAGAAACCAGGGAAAGCCCCTAAGCTCCTGATCTATG

CTGCATCCAGTTTGCAAAGTGGGGTCCCATCACGTTTCAGTGGCAGTGGA

AGCGGGACAGATTTCACTCTCACCATCAGCAGTCTGCAACCTGAAGATTT

GCAACTTATTACTGTCAACAGAGTTACAGTACCCCTTATACTTTTGGC

CAGGGGACCAAGCTGGAGATCAAA

Antibody 1134/1135

Variable heavy chain (V_H) amino acid sequence
SEQ ID NO: 71
EVQLLESGGGLVQPGGSLRLSCAAS<u>GFTFSSYA</u>MSWVRQAPGKGLEWVS <u>SIYSGGGGT</u>SYADSVKGRFTISRDNSKNTLYLQMNSLRAEDTAVYYC<u>AR</u>

<u>GPAYSSFFDY</u>WGQGTLVTVSS

Variable light chain (V_L) amino acid sequence
SEQ ID NO: 72
DIQMTQSPSSLSASVGDRVTITCRAS<u>QSISSY</u>LNWYQQKPGKAPKLLIY <u>AAS</u>SLQSGVPSRFSGSGSGTDFTLTISSLQPEDFATYYC<u>QQSYSTPYT</u>

FGQGTKLEIK

CDR amino acid sequences
V_H CDRs: CDR1: GFTFSSYA [SEQ ID NO: 31]
         CDR2: IYSGGGGT [SEQ ID NO: 32]
         CDR3: ARGPAYSSFFDY [SEQ ID NO: 33]

V_L CDRs: CDR1: QSISSY [SEQ ID NO: 34]
         CDR2: AAS [SEQ ID NO: 35]
         CDR3: QQSYSTPYT [SEQ ID NO: 36]

Variable heavy chain (V_H) nucleotide sequence
SEQ ID NO: 91
GAGGTGCAGCTGTTGGAGAGCGGGGGAGGCTTGGTACAGCCTGGGGGTC

CCTGCGCCTCTCCTGTGCAGCCAGCGGATTCACCTTTAGCAGCTATGCCA

TGAGCTGGGTCCGCCAGGCTCCAGGGAAGGGGCTGGAGTGGGTCTCATC

TATTTACTCTGGTGGTGGTGGTACATCTTATGCAGACTCCGTGAAGGGC

CGGTTCACCATCTCCCGTGACAATTCCAAGAACACGCTGTATCTGCAAA

TGAACAGCCTGCGTGCCGAGGACACGGCTGTATATTATTGTGCGCGCGGT

CCGGCTTACTCTTCTTTCTTTGACTATTGGGGCCAGGGAACCCTGGTCAC

CGTCTCCTCA

Variable light chain (V_L) nucleotide sequence
SEQ ID NO: 92
GACATCCAGATGACCCAGTCTCCATCCTCCCTGAGCGCATCTGTAGGAG

ACCGCGTCACCATCACTTGCCGGGCAAGTCAGAGCATTAGCAGCTATTTA

AATTGGTATCAGCAGAAACCAGGGAAAGCCCCTAAGCTCCTGATCTATGC

TGCATCCAGTTTGCAAAGTGGGGTCCCATCACGTTTCAGTGGCAGTGGAA

GCGGGACAGATTTCACTCTCACCATCAGCAGTCTGCAACCTGAAGATTTT

GCAACTTATTACTGTCAACAGAGTTACAGTACCCCTTATACTTTTGGCCA

GGGGACCAAGCTGGAGATCAAA

Antibody 1136/1137

Variable heavy chain (V_H) amino acid sequence
SEQ ID NO: 73
EVQLLESGGGLVQPGGSLRLSCAAS<u>GFTFSSYA</u>MSWVRQAPGKGLEWVS <u>AISGSGGST</u>YYADSVKGRFTISRDNSKNTLYLQMNSLRAEDTAVYYC<u>AR</u>

<u>YVFGIDY</u>WGQGTLVTVSS

Variable light chain (V_L) amino acid sequence
SEQ ID NO: 74
DIQMTQSPSSLSASVGDRVTITCRAS<u>QSISSY</u>LNWYQQKPGKAPKLLIY<u>A</u>

<u>ASS</u>LQSGVPSRFSGSGSGTDFTLTISSLQPEDFATYYC<u>QQAYYAGLFT</u>F

GQGTKLEIK

CDR amino acid sequences
V_H CDRs: CDR1: GFTFSSYA [SEQ ID NO: 37]
         CDR2: ISGSGGST [SEQ ID NO: 38]
         CDR3: ARYVFGIDY [SEQ ID NO: 39]

V_L CDRs: CDR1: QSISSY [SEQ ID NO: 40]
         CDR2: AAS [SEQ ID NO: 41]
         CDR3: QQAYYAGLFT [SEQ ID NO: 42]

Variable heavy chain (V_H) nucleotide sequence
SEQ ID NO: 93
GAGGTGCAGCTGTTGGAGAGCGGGGGAGGCTTGGTACAGCCTGGGGGGT

CCCTGCGCCTCTCCTGTGCAGCCAGCGGATTCACCTTTAGCAGCTATGCC

ATGAGCTGGGTCCGCCAGGCTCCAGGGAAGGGGCTGGAGTGGGTCTCAG

CTATTAGTGGTAGTGGTGGTAGCACATACTATGCAGACTCCGTGAAGGGC

CGGTTCACCATCTCCCGTGACAATTCCAAGAACACGCTGTATCTGCAAAT

GAACAGCCTGCGTGCCGAGGACACGGCTGTATATTATTGTGCGCGCTACG

TTTTCGGTATTGACTATTGGGGCCAGGGAACCCTGGTCACCGTCTCCTCA

Variable light chain (V_L) nucleotide sequence
SEQ ID NO: 94
GACATCCAGATGACCCAGTCTCCATCCTCCCTGAGCGCATCTGTAGGAGA

CCGCGTCACCATCACTTGCCGGGCAAGTCAGAGCATTAGCAGCTATTTAA

ATTGGTATCAGCAGAAACCAGGGAAAGCCCCTAAGCTCCTGATCTATGCT

GCATCCAGTTTGCAAAGTGGGGTCCCATCACGTTTCAGTGGCAGTGGAAG

CGGGACAGATTTCACTCTCACCATCAGCAGTCTGCAACCTGAAGATTTTG

CAACTTATTACTGTCAACAGGCTTACTACGCTGGTCTGTTCACTTTTGGC

CAGGGGACCAAGCTGGAGATAAAA

Antibody 1140/1135

Variable heavy chain (V_H) amino acid sequence
SEQ ID NO: 75
EVQLLESGGGLVQPGGSLRLSCAAS<u>GFTFSSYA</u>MSWVRQAPGKGLEWVSA <u>ISGSGGST</u>YYADSVKGRFTISRDNSKNTLYLQMNSLRAEDTAVYYC<u>ARGP</u>

<u>VYSSVFDY</u>WGQGTLVTVSS

Variable light chain (V_L) amino acid sequence
SEQ ID NO: 76
DIQMTQSPSSLSASVGDRVTITCRAS<u>QSISSY</u>LNWYQQKPGKAPKLLIY<u>A</u>

<u>ASS</u>LQSGVPSRFSGSGSGTDFTLTISSLQPEDFATYYC<u>QQSYSTPYT</u>FGQ

GTKLEIK

CDR amino acid sequences
V_H CDRs: CDR1: GFTFSSYA [SEQ ID NO: 43]
         CDR2: ISGSGGST [SEQ ID NO: 44]
         CDR3: ARGPVYSSVFDY [SEQ ID NO: 45]

V_L CDRs: CDR1: QSISSY [SEQ ID NO: 46]
         CDR2: AAS [SEQ ID NO: 47]
         CDR3: QQSYSTPYT [SEQ ID NO: 48]

Variable heavy chain (V_H) nucleotide sequence
SEQ ID NO: 95
GAGGTGCAGCTGTTGGAGAGCGGGGGAGGCTTGGTACAGCCTGGGGGTC

CCTGCGCCTCTCCTGTGCAGCCAGCGGATTCACCTTTAGCAGCTATGCCA

TGAGCTGGGTCCGCCAGGCTCCAGGGAAGGGGCTGGAGTGGGTCTCAGCT

ATTAGTGGTAGTGGTGGTAGCACATACTATGCAGACTCCGTGAAGGGCCG

GTTCACCATCTCCCGTGACAATTCCAAGAACACGCTGTATCTGCAAATGA

-continued

ACAGCCTGCGTGCCGAGGACACGGCTGTATATTATTGTGCGCGGTCCG

GTTTACTCTTCTGTTTTTGACTATTGGGGCCAGGGAACCCTGGTCACCGT

CTCCTCA

Variable light chain (V_L) nucleotide sequence
SEQ ID NO: 96
GACATCCAGATGACCCAGTCTCCATCCTCCCTGAGCGCATCTGTAGGAGA

CCGCGTCACCATCACTTGCCGGGCAAGTCAGAGCATTAGCAGCTATTTAA

ATTGGTATCAGCAGAAACCAGGGAAAGCCCCTAAGCTCCTGATCTATGCT

GCATCCAGTTTGCAAAGTGGGGTCCCATCACGTTTCAGTGGCAGTGGAAG

CGGGACAGATTTCACTCTCACCATCAGCAGTCTGCAACCTGAAGATTTTG

CAACTTATTACTGTCAACAGAGTTACAGTACCCCTTATACTTTTGGCCAG

GGGACCAAGCTGGAGATCAAA

Antibody 1150/1151

Variable heavy chain (V_H) amino acid sequence
SEQ ID NO: 77
EVQLLESGGGLVQPGGSLRLSCAASGFTFSSYAMSWVRQAPGKGLEWVSG

IGGSSSYTSYADSVKGRFTISRDNSKNTLYLQMNSLRAEDTAVYYCARYY

SYHMDYWGQGTLVTVSS

Variable light chain (V_L) amino acid sequence
SEQ ID NO: 78
DIQMTQSPSSLSASVGDHVTITCRASQSISSYLNWYQQKPGKAPKLLIYA

ASSLQSGVPSRFSGSGSGTDFTLTISSLQPEDFATYYCQQYGSAPPTFGQ

GTKLEIK

CDR amino acid sequences
V_H CDRs: CDR1: GFTFSSYA [SEQ ID NO: 49]
         CDR2: IGGSSSYT [SEQ ID NO: 50]
         CDR3: ARYYSYHMDY [SEQ ID NO: 51]

V_L CDRs: CDR1: QSISSY [SEQ ID NO: 52]
          CDR2: AAS [SEQ ID NO: 53]
          CDR3: QQYGSAPPT [SEQ ID NO: 54]

Variable heavy chain (V_H) nucleotide sequence
SEQ ID NO: 97
GAGGTGCAGCTGTTGGAGAGCGGGGGAGGCTTGGTACAGCCTGGGGGGTC

CCTGCGCCTCTCCTGTGCAGCCAGCGGATTCACCTTTAGCAGCTATGCCA

TGAGCTGGGTCCGCCAGGCTCCAGGGAAGGGGCTGGAGTGGGTCTCAGGT

ATTGGTGGTTCTTCTTCTTACACATCTTATGCAGACTCCGTGAAGGGCCG

GTTCACCATCTCCCGTGACAATTCCAAGAACACGCTGTATCTGCAAATGA

ACAGCCTGCGTGCCGAGGACACGGCTGTATATTATTGTGCGCGCTACTAC

TCTTACCATATGGACTATTGGGGCCAGGGAACCCTGGTCACCGTCTCCTC

A

Variable light chain (V_L) nucleotide sequence
SEQ ID NO: 98
GACATCCAGATGACCCAGTCTCCATCCTCCCTGAGCGCATCTGTAGGAGA

CCACGTCACCATCACTTGCCGGGCAAGTCAGAGCATTAGCAGCTATTTAA

ATTGGTATCAGCAGAAACCAGGGAAAGCCCCTAAGCTCCTGATCTATGCT

GCATCCAGTTTGCAAAGTGGGGTCCCATCACGTTTCAGTGGCAGTGGAAG

CGGGACAGATTTCACTCTCACCATCAGCAGTCTGCAACCTGAAGATTTTG

CAACTTATTACTGTCAACAGTACGGTTCTGCTCCGCCCACTTTTGGCCAG

GGGACCAAGCTGGAGATCAAA

Antibody 1107/1108

Variable heavy chain (V_H) amino acid sequence
SEQ ID NO: 79
EVQLLESGGGLVQPGGSLRLSCAASGFTFSSYAMSWVRQAPGKGLEWVSA

ISGSGGSTYYADSVKGRFTISRDNSKNTLYLQMNSLRAEDTAVYYCARRV

WGFDYWGQGTLVTVSS

Variable light chain (V_L) amino acid sequence
SEQ ID NO: 80
DIQMTQSPSSLSASVGDRVTITCRASQSISSYLNWYQQKPGKAPKLLIYA

ASSLQSGVPSRFSGSGSGTDFTLTISSLQPEDFATYYCQQYGVYPFTFGQ

GTKLEIK

CDR amino acid sequences
V_H CDRs: CDR1: GFTFSSYA [SEQ ID NO: 55]
         CDR2: ISGSGGST [SEQ ID NO: 56]
         CDR3: ARRVWGFDY [SEQ ID NO: 57]

V_L CDRs: CDR1: QSISSY [SEQ ID NO: 58]
          CDR2: AAS [SEQ ID NO: 59]
          CDR3: QQYGVYPFT [SEQ ID NO: 60]

Variable heavy chain (V_H) nucleotide sequence
SEQ ID NO: 99
GAGGTGCAGCTGTTGGAGAGCGGGGGAGGCTTGGTACAGCCTGGGGGGTC

CCTGCGCCTCTCCTGTGCAGCCAGCGGATTCACCTTTAGCAGCTATGCCA

TGAGCTGGGTCCGCCAGGCTCCAGGGAAGGGGCTGGAGTGGGTCTCAGCT

ATTAGTGGTAGTGGTGGTAGCACATACTATGCAGACTCCGTGAAGGGCCG

GTTCACCATCTCCCGTGACAATTCCAAGAACACGCTGTATCTGCAAATGA

ACAGCCTGCGTGCCGAGGACACGGCTGTATATTATTGTGCGCGCCGTGTT

TGGGGTTTTGACTATTGGGGCCAGGGAACCCTGGTCACCGTCTCCTCAGG

Variable light chain (V_L) nucleotide sequence
SEQ ID NO: 100
GACATCCAGATGACCCAGTCTCCATCCTCCCTGAGCGCATCTGTAGGAGA

CCGCGTCACCATCACTTGCCGGGCAAGTCAGAGCATTAGCAGCTATTTAA

ATTGGTATCAGCAGAAACCAGGGAAAGCCCCTAAGCTCCTGATCTATGCT

GCATCCAGTTTGCAAAGTGGGGTCCCATCACGTTTCAGTGGCAGTGGAAG

CGGGACAGATTTCACTCTCACCATCAGCAGTCTGCAACCTGAAGATTTTG

CAACTTATTACTGTCAACAGTACGGTGTTTACCCGTTCACTTTTGGCCAG

GGGACCAAGCTGGAGATCAAA

Exemplary Constant Regions of Antibodies of the Invention
Constant Heavy Chain (C_H) Amino Acid Sequence (Igγ 2-4_HUMAN)—SEQ ID NO:101
Published in Mueller J. P. et al. Molecular Immunology vol. 34 no. 6 pp 441-452, 1997

ASTKGPSVFPLAPCSRSTSESTAALGCLVKDYFPEPVTVSWNSGALTSGV

HTFPAVLQSSGLYSLSSVVTVPSSNFGTQTYTCNVDHKPSNTKVDKTVER

KCCVECPPCPAPPVAGPSVFLFPPKPKDTLMISRTPEVTCVVVDVSQEDP

EVQFNWYVDGVEVHNAKTKPREEQFNSTYRVVSVLTVLHQDWLNGKEYKC

-continued

KVSNKGLPSSIEKTISKAKGQPREPQVYTLPPSQEEMTKNQVSLTCLVKG

FYPSDIAVEWESNGQPENNYKTTPPVLDSDGSFFLYSRLTVDKSRWQEGN

VFSCSVMHEALHNHYTQKSLSLSLGK

Constant Heavy Chain ($C_H$) Amino Acid Sequence (Igγ-1_Uniprot Accession number:P01857_HUMAN)—SEQ ID NO:102

ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTC

LVKGFYPSDIAVEWESNGQPENNYKTTPPVLDSDGSFFLYSKLTVDKSRW

QQGNVFSCSVMHEALHNHYTQKSLSLSPGK

Constant Light Chain ($C_L$) Amino Acid Sequence (Igκ Chain C Region Genbank Accession Number: AAA58989.1_HUMAN)—SEQ ID NO:103

TVAAPSVFIFPPSDEQLKSGTASVVCLLNNFYPREAKVQWKVDNALQSGN

SQESVTEQDSKDSTYSLSSTLTLSKADYEKHKVYACEVTHQGLSSPVTKS

FNRGEC

Antibodies of the invention may include an Fc region (e.g. a heavy or light chain constant region) into which mutations have been introduced, for example to increase affinity for FcγR and/or decrease affinity for FcRn. Increased affinity for for FcγR may result in enhanced activity of an agonistic anti-CD40 antibody. By contrast, decreased affinity for FcRn may result in reduced serum half-life, which may be advantageous in the context of local, particularly intratumoral, cancer treatment. Examples of such mutated Fc regions include:

A $C_H$ region of IgG1 with mutation H435R;
A $C_H$ region of IgG1 with mutations H435R and S239D;
A $C_H$ region of IgG1 with mutations H435R and S239D and I322E; and
A $C_H$ region of IgG1 with mutations H435R and K290A The H435R mutation is based on the presence of R in the corresponding position of the $C_H$ region of IgG3. All positions in the above mutations are numbered in accordance with the EU numbering scheme of Kabat et al Antibody Target: The Human CD40 Molecule, TNF Receptor Superfamily Member 5

SEQ ID NO: 104
MVRLPLQCVLWGCLLTAVHPEPPTACREKQYLINSQCCSLCQPGQKLVSD

CTEFTETECLPCGESEFLDTWNRETHCHQHKYCDPNLGLRVQQKGTSETD

TICTCEEGWHCTSEACESCVLHRSCSPGFGVKQIATGVSDTICEPCPVGF

FSNVSSAFEKCHPWTSCETKDLVVQQAGTNKTDVVCGPQDRLRALVVIPI

IFGILFAILLVLVFIKKVAKKPTNKAPHPKQEPQEINFPDDLPGSNTAAP

VQETLHGCQPVTQEDGKESRISVQERQ

Exemplary CTLA-4 Binding Regions (wild-type extracellular region of human CD86)
SEQ ID NO: 105
APLKIQAYFNETADLPCQFANSQNQSLSELVVFWQDQENLVLNEVYLGKE

KFDSVHSKYMGRTSFDSDSWTLRLHNLQIKDKGLYQCIIHHKKPTGMIRI

HQMNSELSVLA (variant of SEQ ID NO: 105)
SEQ ID NO: 106
LKIQAYFNETADLPCQFANSQNQSLSELIVFWQDQENLVLNEVYLGKERF

DAVDSKYMGRTSFDSDSWTLRLHNLQIKDKGIYQCIIHHKKPSGMVKIHQ

MDSELSVLA (variant of SEQ ID NO: 105)
SEQ ID NO: 107
APLKIQAYFNETADLPCQFANSQNLSLSELVVFWQDQENLVLNEVYLGKE

RFDSVDSKYMGRTSFDSDSWTLRLHNLQIKDKGRYQCIIHHKKPTGMINI

HQMNSELSVLA (variant of SEQ ID NO: 105)
SEQ ID NO: 108
APLKIQAYFNETADLPCQFANSQNLTLSELVVFWQDQENLVLNEVYLGKE

KFDSVSSKYMGRTSFDSDSWTLRLHNLQIKDKGIYQCIIHHKKPTGMIKI

HEMSSELSVLA

The invention claimed is:

1. A human antibody or fragment thereof, wherein the antibody or fragment thereof comprises the complementarity determining regions (CDRs) of:
   (i) SEQ ID NOs 43, 44, 45, 46, 47 and 48; or
   (ii) SEQ ID NOs 13, 14, 15, 16, 17 and 18; or
   (iii) SEQ ID NOs 31, 32, 33, 34, 35 and 36; or
   (iv) SEQ ID NOs 37, 38, 39, 40, 41 and 42; or
   (v) SEQ ID NOs 49, 50, 51, 52, 53 and 54; or
   (vi) SEQ ID NOs 55, 56, 57, 58, 59 and 60,
wherein said antibody or fragment thereof:
   (a) binds to human CD40 when localised on the surface of a cell; and/or
   (b) enhances antibody dependent cellular cytotoxicity (ADCC)-mediated lysis of a cell expressing CD40; and/or
   (c) enhances apoptosis of a cell expressing CD40; and/or
   (d) modulates the activity of a cell expressing CD40, wherein said modulation is an increase or decrease in the activity of said cell; and/or
   (e) blocks binding of CD40L to CD40, reduces binding of CD40L to CD40, or does not block or reduce binding of CD40L to CD40.

2. The antibody or fragment according to claim 1 that increases the activity of a CD11c-positive cell or a CD11b-positive cell, optionally wherein said increase in activity is indicated by an increase in CD86 expression by said cell.

3. The antibody or fragment thereof according to claim 1, wherein the antibody or fragment thereof further comprises a heavy chain variable region amino acid sequence of SEQ ID NO: 75, 65, 71, 73, 77 or 79.

4. The antibody or fragment thereof according to claim 1, wherein the antibody or fragment thereof further comprises a light chain variable region amino acid sequence of SEQ ID NO: 76, 66, 72, 74, 78 or 80.

5. The antibody or fragment thereof according to claim 1, wherein the antibody or fragment thereof comprises:
   (a) the heavy chain variable region of SEQ ID NO: 75 and the light chain variable region of SEQ ID NO: 76; or
   (b) the heavy chain variable region of SEQ ID NO: 65 and the light chain variable region of SEQ ID NO: 66; or
   (c) the heavy chain variable region of SEQ ID NO: 71 and the light chain variable region of SEQ ID NO: 72; or
   (d) the heavy chain variable region of SEQ ID NO: 73 and the light chain variable region of SEQ ID NO: 74; or
   (e) the heavy chain variable region of SEQ ID NO: 77 and the light chain variable region of SEQ ID NO: 78; or
   (f) the heavy chain variable region of SEQ ID NO: 79 and the light chain variable region of SEQ ID NO: 80.

6. The antibody or fragment according to claim 1 which comprises an Fc region which is an IgG1, IgG2, IgG3 or IgG4 region.

7. The antibody or fragment thereof according to claim 1 conjugated to an additional moiety, wherein the additional moiety is a polypeptide binding domain specific for human CTLA-4, wherein said binding domain comprises the amino acid sequence of SEQ ID NO: 105.

8. A composition comprising an antibody or fragment thereof according to claim 1 and at least one pharmaceutically acceptable diluent or carrier.

* * * * *

SEQUENCE LISTING

```
<160> NUMBER OF SEQ ID NOS: 116

<210> SEQ ID NO 1
<211> LENGTH: 8
<212> TYPE: PRT
<213> ORGANISM: Homo sapiens

<400> SEQUENCE: 1

Gly Phe Thr Phe Ser Ser Tyr Ala
1               5

<210> SEQ ID NO 2
<211> LENGTH: 8
<212> TYPE: PRT
<213> ORGANISM: Homo sapiens
```

<400> SEQUENCE: 2

Ile Ser Gly Ser Gly Gly Ser Thr
1               5

<210> SEQ ID NO 3
<211> LENGTH: 9
<212> TYPE: PRT
<213> ORGANISM: Homo sapiens

<400> SEQUENCE: 3

Ala Arg Arg Val Phe Gly Phe Asp Tyr
1               5

<210> SEQ ID NO 4
<211> LENGTH: 6
<212> TYPE: PRT
<213> ORGANISM: Homo sapiens

<400> SEQUENCE: 4

Gln Ser Ile Ser Ser Tyr
1               5

<210> SEQ ID NO 5
<211> LENGTH: 3
<212> TYPE: PRT
<213> ORGANISM: Homo sapiens

<400> SEQUENCE: 5

Ala Ala Ser
1

<210> SEQ ID NO 6
<211> LENGTH: 9
<212> TYPE: PRT
<213> ORGANISM: Homo sapiens

<400> SEQUENCE: 6

Gln Gln Tyr Tyr Tyr Tyr Pro Phe Thr
1               5

<210> SEQ ID NO 7
<211> LENGTH: 8
<212> TYPE: PRT
<213> ORGANISM: Homo sapiens

<400> SEQUENCE: 7

Gly Phe Thr Phe Ser Ser Tyr Ala
1               5

<210> SEQ ID NO 8
<211> LENGTH: 8
<212> TYPE: PRT
<213> ORGANISM: Homo sapiens

<400> SEQUENCE: 8

Ile Ser Gly Ser Gly Gly Ser Thr
1               5

<210> SEQ ID NO 9
<211> LENGTH: 12
<212> TYPE: PRT
<213> ORGANISM: Homo sapiens

<400> SEQUENCE: 9

Ala Arg Gly Pro Ala Tyr Ser Thr Val Leu Asp Tyr
1               5                   10

<210> SEQ ID NO 10
<211> LENGTH: 6
<212> TYPE: PRT
<213> ORGANISM: Homo sapiens

<400> SEQUENCE: 10

Gln Ser Ile Ser Ser Tyr
1               5

<210> SEQ ID NO 11
<211> LENGTH: 3
<212> TYPE: PRT
<213> ORGANISM: Homo sapiens

<400> SEQUENCE: 11

Ala Ala Ser
1

<210> SEQ ID NO 12
<211> LENGTH: 9
<212> TYPE: PRT
<213> ORGANISM: Homo sapiens

<400> SEQUENCE: 12

Gln Gln Ser Tyr Ser Thr Pro Tyr Thr
1               5

<210> SEQ ID NO 13
<211> LENGTH: 8
<212> TYPE: PRT
<213> ORGANISM: Homo sapiens

<400> SEQUENCE: 13

Gly Phe Thr Phe Ser Ser Tyr Ala
1               5

<210> SEQ ID NO 14
<211> LENGTH: 8
<212> TYPE: PRT
<213> ORGANISM: Homo sapiens

<400> SEQUENCE: 14

Ile Gly Ser Tyr Gly Gly Gly Thr
1               5

<210> SEQ ID NO 15
<211> LENGTH: 10
<212> TYPE: PRT
<213> ORGANISM: Homo sapiens

<400> SEQUENCE: 15

Ala Arg Tyr Val Asn Phe Gly Met Asp Tyr
1               5                   10

<210> SEQ ID NO 16
<211> LENGTH: 6
<212> TYPE: PRT
<213> ORGANISM: Homo sapiens

<400> SEQUENCE: 16

Gln Ser Ile Ser Ser Tyr
1               5

<210> SEQ ID NO 17
<211> LENGTH: 3
<212> TYPE: PRT
<213> ORGANISM: Homo sapiens

<400> SEQUENCE: 17

Ala Ala Ser
1

<210> SEQ ID NO 18
<211> LENGTH: 9
<212> TYPE: PRT
<213> ORGANISM: Homo sapiens

<400> SEQUENCE: 18

Gln Gln Tyr Gly Arg Asn Pro Pro Thr
1               5

<210> SEQ ID NO 19
<211> LENGTH: 8
<212> TYPE: PRT
<213> ORGANISM: Homo sapiens

<400> SEQUENCE: 19

Gly Phe Thr Phe Ser Ser Tyr Ala
1               5

<210> SEQ ID NO 20
<211> LENGTH: 8
<212> TYPE: PRT
<213> ORGANISM: Homo sapiens

<400> SEQUENCE: 20

Ile Ser Gly Ser Gly Gly Ser Thr
1               5

<210> SEQ ID NO 21
<211> LENGTH: 9
<212> TYPE: PRT
<213> ORGANISM: Homo sapiens

<400> SEQUENCE: 21

Ala Arg Ala Val Phe Gly Phe Asp Tyr
1               5

<210> SEQ ID NO 22
<211> LENGTH: 6
<212> TYPE: PRT
<213> ORGANISM: Homo sapiens

<400> SEQUENCE: 22

Gln Ser Ile Ser Ser Tyr
1               5

<210> SEQ ID NO 23
<211> LENGTH: 3
<212> TYPE: PRT
<213> ORGANISM: Homo sapiens

<400> SEQUENCE: 23

Ala Ala Ser
1

```
<210> SEQ ID NO 24
<211> LENGTH: 9
<212> TYPE: PRT
<213> ORGANISM: Homo sapiens

<400> SEQUENCE: 24

Gln Gln Ala Tyr Tyr Phe Pro His Thr
1               5

<210> SEQ ID NO 25
<211> LENGTH: 8
<212> TYPE: PRT
<213> ORGANISM: Homo sapiens

<400> SEQUENCE: 25

Gly Phe Thr Phe Ser Ser Tyr Ala
1               5

<210> SEQ ID NO 26
<211> LENGTH: 8
<212> TYPE: PRT
<213> ORGANISM: Homo sapiens

<400> SEQUENCE: 26

Ile Ser Gly Ser Gly Gly Ser Thr
1               5

<210> SEQ ID NO 27
<211> LENGTH: 12
<212> TYPE: PRT
<213> ORGANISM: Homo sapiens

<400> SEQUENCE: 27

Ala Arg Gly Phe Val Tyr Ser Ser Tyr Ile Asp Tyr
1               5                   10

<210> SEQ ID NO 28
<211> LENGTH: 6
<212> TYPE: PRT
<213> ORGANISM: Homo sapiens

<400> SEQUENCE: 28

Gln Ser Ile Ser Ser Tyr
1               5

<210> SEQ ID NO 29
<211> LENGTH: 3
<212> TYPE: PRT
<213> ORGANISM: Homo sapiens

<400> SEQUENCE: 29

Ala Ala Ser
1

<210> SEQ ID NO 30
<211> LENGTH: 9
<212> TYPE: PRT
<213> ORGANISM: Homo sapiens

<400> SEQUENCE: 30

Gln Gln Ser Tyr Ser Thr Pro Tyr Thr
1               5

<210> SEQ ID NO 31
<211> LENGTH: 8
```

```
<212> TYPE: PRT
<213> ORGANISM: Homo sapiens

<400> SEQUENCE: 31

Gly Phe Thr Phe Ser Ser Tyr Ala
1               5

<210> SEQ ID NO 32
<211> LENGTH: 8
<212> TYPE: PRT
<213> ORGANISM: Homo sapiens

<400> SEQUENCE: 32

Ile Tyr Ser Gly Gly Gly Gly Thr
1               5

<210> SEQ ID NO 33
<211> LENGTH: 12
<212> TYPE: PRT
<213> ORGANISM: Homo sapiens

<400> SEQUENCE: 33

Ala Arg Gly Pro Ala Tyr Ser Ser Phe Phe Asp Tyr
1               5                   10

<210> SEQ ID NO 34
<211> LENGTH: 6
<212> TYPE: PRT
<213> ORGANISM: Homo sapiens

<400> SEQUENCE: 34

Gln Ser Ile Ser Ser Tyr
1               5

<210> SEQ ID NO 35
<211> LENGTH: 3
<212> TYPE: PRT
<213> ORGANISM: Homo sapiens

<400> SEQUENCE: 35

Ala Ala Ser
1

<210> SEQ ID NO 36
<211> LENGTH: 9
<212> TYPE: PRT
<213> ORGANISM: Homo sapiens

<400> SEQUENCE: 36

Gln Gln Ser Tyr Ser Thr Pro Tyr Thr
1               5

<210> SEQ ID NO 37
<211> LENGTH: 8
<212> TYPE: PRT
<213> ORGANISM: Homo sapiens

<400> SEQUENCE: 37

Gly Phe Thr Phe Ser Ser Tyr Ala
1               5

<210> SEQ ID NO 38
<211> LENGTH: 8
<212> TYPE: PRT
<213> ORGANISM: Homo sapiens
```

<400> SEQUENCE: 38

Ile Ser Gly Ser Gly Gly Ser Thr
1               5

<210> SEQ ID NO 39
<211> LENGTH: 9
<212> TYPE: PRT
<213> ORGANISM: Homo sapiens

<400> SEQUENCE: 39

Ala Arg Tyr Val Phe Gly Ile Asp Tyr
1               5

<210> SEQ ID NO 40
<211> LENGTH: 6
<212> TYPE: PRT
<213> ORGANISM: Homo sapiens

<400> SEQUENCE: 40

Gln Ser Ile Ser Ser Tyr
1               5

<210> SEQ ID NO 41
<211> LENGTH: 3
<212> TYPE: PRT
<213> ORGANISM: Homo sapiens

<400> SEQUENCE: 41

Ala Ala Ser
1

<210> SEQ ID NO 42
<211> LENGTH: 10
<212> TYPE: PRT
<213> ORGANISM: Homo sapiens

<400> SEQUENCE: 42

Gln Gln Ala Tyr Tyr Ala Gly Leu Phe Thr
1               5                   10

<210> SEQ ID NO 43
<211> LENGTH: 8
<212> TYPE: PRT
<213> ORGANISM: Homo sapiens

<400> SEQUENCE: 43

Gly Phe Thr Phe Ser Ser Tyr Ala
1               5

<210> SEQ ID NO 44
<211> LENGTH: 8
<212> TYPE: PRT
<213> ORGANISM: Homo sapiens

<400> SEQUENCE: 44

Ile Ser Gly Ser Gly Gly Ser Thr
1               5

<210> SEQ ID NO 45
<211> LENGTH: 12
<212> TYPE: PRT
<213> ORGANISM: Homo sapiens

<400> SEQUENCE: 45

Ala Arg Gly Pro Val Tyr Ser Ser Val Phe Asp Tyr
1               5                   10

<210> SEQ ID NO 46
<211> LENGTH: 6
<212> TYPE: PRT
<213> ORGANISM: Homo sapiens

<400> SEQUENCE: 46

Gln Ser Ile Ser Ser Tyr
1               5

<210> SEQ ID NO 47
<211> LENGTH: 3
<212> TYPE: PRT
<213> ORGANISM: Homo sapiens

<400> SEQUENCE: 47

Ala Ala Ser
1

<210> SEQ ID NO 48
<211> LENGTH: 9
<212> TYPE: PRT
<213> ORGANISM: Homo sapiens

<400> SEQUENCE: 48

Gln Gln Ser Tyr Ser Thr Pro Tyr Thr
1               5

<210> SEQ ID NO 49
<211> LENGTH: 8
<212> TYPE: PRT
<213> ORGANISM: Homo sapiens

<400> SEQUENCE: 49

Gly Phe Thr Phe Ser Ser Tyr Ala
1               5

<210> SEQ ID NO 50
<211> LENGTH: 8
<212> TYPE: PRT
<213> ORGANISM: Homo sapiens

<400> SEQUENCE: 50

Ile Gly Gly Ser Ser Ser Tyr Thr
1               5

<210> SEQ ID NO 51
<211> LENGTH: 10
<212> TYPE: PRT
<213> ORGANISM: Homo sapiens

<400> SEQUENCE: 51

Ala Arg Tyr Tyr Ser Tyr His Met Asp Tyr
1               5                   10

<210> SEQ ID NO 52
<211> LENGTH: 6
<212> TYPE: PRT
<213> ORGANISM: Homo sapiens

<400> SEQUENCE: 52

Gln Ser Ile Ser Ser Tyr

```
1               5
```

<210> SEQ ID NO 53
<211> LENGTH: 3
<212> TYPE: PRT
<213> ORGANISM: Homo sapiens
<400> SEQUENCE: 53

```
Ala Ala Ser
1
```

<210> SEQ ID NO 54
<211> LENGTH: 9
<212> TYPE: PRT
<213> ORGANISM: Homo sapiens
<400> SEQUENCE: 54

```
Gln Gln Tyr Gly Ser Ala Pro Pro Thr
1               5
```

<210> SEQ ID NO 55
<211> LENGTH: 8
<212> TYPE: PRT
<213> ORGANISM: Homo sapiens
<400> SEQUENCE: 55

```
Gly Phe Thr Phe Ser Ser Tyr Ala
1               5
```

<210> SEQ ID NO 56
<211> LENGTH: 8
<212> TYPE: PRT
<213> ORGANISM: Homo sapiens
<400> SEQUENCE: 56

```
Ile Ser Gly Ser Gly Gly Ser Thr
1               5
```

<210> SEQ ID NO 57
<211> LENGTH: 9
<212> TYPE: PRT
<213> ORGANISM: Homo sapiens
<400> SEQUENCE: 57

```
Ala Arg Arg Val Trp Gly Phe Asp Tyr
1               5
```

<210> SEQ ID NO 58
<211> LENGTH: 6
<212> TYPE: PRT
<213> ORGANISM: Homo sapiens
<400> SEQUENCE: 58

```
Gln Ser Ile Ser Ser Tyr
1               5
```

<210> SEQ ID NO 59
<211> LENGTH: 3
<212> TYPE: PRT
<213> ORGANISM: Homo sapiens
<400> SEQUENCE: 59

```
Ala Ala Ser
1
```

<210> SEQ ID NO 60
<211> LENGTH: 9
<212> TYPE: PRT
<213> ORGANISM: Homo sapiens

<400> SEQUENCE: 60

Gln Gln Tyr Gly Val Tyr Pro Phe Thr
1               5

<210> SEQ ID NO 61
<211> LENGTH: 116
<212> TYPE: PRT
<213> ORGANISM: Homo sapiens

<400> SEQUENCE: 61

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Val Phe Gly Phe Asp Tyr Trp Gly Gln Gly Thr Leu Val
            100                 105                 110

Thr Val Ser Ser
        115

<210> SEQ ID NO 62
<211> LENGTH: 107
<212> TYPE: PRT
<213> ORGANISM: Homo sapiens

<400> SEQUENCE: 62

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Tyr Pro Phe
                85                  90                  95

Thr Phe Gly Gln Gly Thr Lys Leu Glu Ile Lys
            100                 105

<210> SEQ ID NO 63
<211> LENGTH: 119
<212> TYPE: PRT
<213> ORGANISM: Homo sapiens

<400> SEQUENCE: 63

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Pro Ala Tyr Ser Thr Val Leu Asp Tyr Trp Gly Gln Gly
            100                 105                 110

Thr Leu Val Thr Val Ser Ser
            115

<210> SEQ ID NO 64
<211> LENGTH: 107
<212> TYPE: PRT
<213> ORGANISM: Homo sapiens

<400> SEQUENCE: 64

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Tyr
                85                  90                  95

Thr Phe Gly Gln Gly Thr Lys Leu Glu Ile Lys
            100                 105

<210> SEQ ID NO 65
<211> LENGTH: 117
<212> TYPE: PRT
<213> ORGANISM: Homo sapiens

<400> SEQUENCE: 65

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Gly Ile Gly Ser Tyr Gly Gly Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

```
Ala Arg Tyr Val Asn Phe Gly Met Asp Tyr Trp Gly Gln Gly Thr Leu
            100                 105                 110

Val Thr Val Ser Ser
            115

<210> SEQ ID NO 66
<211> LENGTH: 107
<212> TYPE: PRT
<213> ORGANISM: Homo sapiens

<400> SEQUENCE: 66

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Gly Arg Asn Pro Pro
                85                  90                  95

Thr Phe Gly Gln Gly Thr Lys Leu Glu Ile Lys
            100                 105

<210> SEQ ID NO 67
<211> LENGTH: 116
<212> TYPE: PRT
<213> ORGANISM: Homo sapiens

<400> SEQUENCE: 67

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Val Phe Gly Phe Asp Tyr Trp Gly Gln Gly Thr Leu Val
            100                 105                 110

Thr Val Ser Ser
            115

<210> SEQ ID NO 68
<211> LENGTH: 107
<212> TYPE: PRT
<213> ORGANISM: Homo sapiens

<400> SEQUENCE: 68

Asp Ile Gln Met Thr Gln Ser Pro Ser Ser Leu Ser Ala Ser Val Gly
1               5                   10                  15
```

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Tyr Tyr Phe Pro His
                85                  90                  95

Thr Phe Gly Gln Gly Thr Lys Leu Glu Ile Lys
            100                 105

<210> SEQ ID NO 69
<211> LENGTH: 119
<212> TYPE: PRT
<213> ORGANISM: Homo sapiens

<400> SEQUENCE: 69

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Phe Val Tyr Ser Ser Tyr Ile Asp Tyr Trp Gly Gln Gly
            100                 105                 110

Thr Leu Val Thr Val Ser Ser
        115

<210> SEQ ID NO 70
<211> LENGTH: 107
<212> TYPE: PRT
<213> ORGANISM: Homo sapiens

<400> SEQUENCE: 70

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Tyr
                85                  90                  95

Thr Phe Gly Gln Gly Thr Lys Leu Glu Ile Lys
            100                 105

<210> SEQ ID NO 71
<211> LENGTH: 119
<212> TYPE: PRT
<213> ORGANISM: Homo sapiens

<400> SEQUENCE: 71

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Tyr Ser Gly Gly Gly Thr Ser Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Pro Ala Tyr Ser Ser Phe Phe Asp Tyr Trp Gly Gln Gly
            100                 105                 110

Thr Leu Val Thr Val Ser Ser
        115

<210> SEQ ID NO 72
<211> LENGTH: 107
<212> TYPE: PRT
<213> ORGANISM: Homo sapiens

<400> SEQUENCE: 72

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Tyr
                85                  90                  95

Thr Phe Gly Gln Gly Thr Lys Leu Glu Ile Lys
            100                 105

<210> SEQ ID NO 73
<211> LENGTH: 116
<212> TYPE: PRT
<213> ORGANISM: Homo sapiens

<400> SEQUENCE: 73

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val

```
                    50                  55                  60
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                     85                  90                  95

Ala Arg Tyr Val Phe Gly Ile Asp Tyr Trp Gly Gln Gly Thr Leu Val
                    100                 105                 110

Thr Val Ser Ser
            115
```

<210> SEQ ID NO 74
<211> LENGTH: 108
<212> TYPE: PRT
<213> ORGANISM: Homo sapiens

<400> SEQUENCE: 74

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Ser Ile Ser Ser Tyr
                 20                  25                  30

Leu Asn Trp Tyr Gln Gln Lys Pro Gly Lys Ala Pro Lys Leu Leu Ile
             35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ala Tyr Tyr Ala Gly Leu
                 85                  90                  95

Phe Thr Phe Gly Gln Gly Thr Lys Leu Glu Ile Lys
             100                 105
```

<210> SEQ ID NO 75
<211> LENGTH: 119
<212> TYPE: PRT
<213> ORGANISM: Homo sapiens

<400> SEQUENCE: 75

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
                 20                  25                  30

Ala Met Ser Trp Val Arg Gln Ala Pro Gly Lys Gly Leu Glu Trp Val
             35                  40                  45

Ser Ala Ile Ser Gly Ser Gly Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Pro Val Tyr Ser Ser Val Phe Asp Tyr Trp Gly Gln Gly
             100                 105                 110

Thr Leu Val Thr Val Ser Ser
            115
```

<210> SEQ ID NO 76
<211> LENGTH: 107
<212> TYPE: PRT

<213> ORGANISM: Homo sapiens

<400> SEQUENCE: 76

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Tyr
                85                  90                  95

Thr Phe Gly Gln Gly Thr Lys Leu Glu Ile Lys
            100                 105

<210> SEQ ID NO 77
<211> LENGTH: 117
<212> TYPE: PRT
<213> ORGANISM: Homo sapiens

<400> SEQUENCE: 77

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Gly Ile Gly Gly Ser Ser Tyr Thr Ser Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Tyr Ser Tyr His Met Asp Tyr Trp Gly Gln Gly Thr Leu
            100                 105                 110

Val Thr Val Ser Ser
        115

<210> SEQ ID NO 78
<211> LENGTH: 107
<212> TYPE: PRT
<213> ORGANISM: Homo sapiens

<400> SEQUENCE: 78

Asp Ile Gln Met Thr Gln Ser Pro Ser Ser Leu Ser Ala Ser Val Gly
1               5                   10                  15

Asp His Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Gly Ser Ala Pro Pro
                85                  90                  95

Thr Phe Gly Gln Gly Thr Lys Leu Glu Ile Lys
            100                 105

<210> SEQ ID NO 79
<211> LENGTH: 116
<212> TYPE: PRT
<213> ORGANISM: Homo sapiens

<400> SEQUENCE: 79

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Val Trp Gly Phe Asp Tyr Trp Gly Gln Gly Thr Leu Val
            100                 105                 110

Thr Val Ser Ser
        115

<210> SEQ ID NO 80
<211> LENGTH: 107
<212> TYPE: PRT
<213> ORGANISM: Homo sapiens

<400> SEQUENCE: 80

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Gly Val Tyr Pro Phe
                85                  90                  95

Thr Phe Gly Gln Gly Thr Lys Leu Glu Ile Lys
            100                 105

<210> SEQ ID NO 81
<211> LENGTH: 348
<212> TYPE: DNA
<213> ORGANISM: Homo sapiens

<400> SEQUENCE: 81
gaggtgcagc tgttggagag cggggggaggc ttggtacagc ctggggggtc cctgcgcctc    60
tcctgtgcag ccagcggatt cacctttagc agctatgcca tgagctgggt ccgccaggct   120

```
ccagggaagg ggctggagtg ggtctcagct attagtggta gtggtggtag cacatactat    180
gcagactccg tgaagggccg gttcaccatc tcccgtgaca attccaagaa cacgctgtat    240
ctgcaaatga acagcctgcg tgccgaggac acggctgtat attattgtgc gcgccgtgtt    300
ttcggttttg actattgggg ccagggaacc ctggtcaccg tctcctca                 348
```

<210> SEQ ID NO 82  
<211> LENGTH: 321  
<212> TYPE: DNA  
<213> ORGANISM: Homo sapiens

<400> SEQUENCE: 82

```
gacatccaga tgacccagtc tccatcctcc ctgagcgcat ctgtaggaga ccgcgtcacc    60
atcacttgcc gggcaagtca gagcattagc agctatttaa attggtatca gcagaaacca    120
gggaaagccc ctaagctcct gatctatgct gcatccagtt tgcaaagtgg ggtcccatca    180
cgtttcagtg gcagtggaag cgggacagat ttcactctca ccatcagcag tctgcaacct    240
gaagattttg caacttatta ctgtcaacag tactactact acccgttcac ttttggccag    300
gggaccaagc tggagatcaa a                                              321
```

<210> SEQ ID NO 83  
<211> LENGTH: 357  
<212> TYPE: DNA  
<213> ORGANISM: Homo sapiens

<400> SEQUENCE: 83

```
gaggtgcagc tgttggagag cgggggaggc ttggtacagc ctggggggtc cctgcgcctc    60
tcctgtgcag ccagcggatt caccttta gc agctatgcca tgagctgggt ccgccaggct    120
ccagggaagg ggctggagtg ggtctcagct attagtggta gtggtggtag cacatactat    180
gcagactccg tgaagggccg gttcaccatc tcccgtgaca attccaagaa cacgctgtat    240
ctgcaaatga acagcctgcg tgccgaggac acggctgtat attattgtgc gcgcggtccg    300
gcttactcta ctgttttgga ctattggggc cagggaaccc tggtcaccgt ctcctca      357
```

<210> SEQ ID NO 84  
<211> LENGTH: 321  
<212> TYPE: DNA  
<213> ORGANISM: Homo sapiens

<400> SEQUENCE: 84

```
gacatccaga tgacccagtc tccatcctcc ctgagcgcat ctgtaggaga ccgcgtcacc    60
atcacttgcc gggcaagtca gagcattagc agctatttaa attggtatca gcagaaacca    120
gggaaagccc ctaagctcct gatctatgct gcatccagtt tgcaaagtgg ggtcccatca    180
cgtttcagtg gcagtggaag cgggacagat ttcactctca ccatcagcag tctgcaacct    240
gaagattttg caacttatta ctgtcaacag agttacagta ccccttatac ttttggccag    300
gggaccaagc tggagatcaa a                                              321
```

<210> SEQ ID NO 85  
<211> LENGTH: 351  
<212> TYPE: DNA  
<213> ORGANISM: Homo sapiens

<400> SEQUENCE: 85

```
gaggtgcagc tgttggagag cgggggaggc ttggtacagc ctggggggtc cctgcgcctc    60
```

```
tcctgtgcag ccagcggatt cacctttagc agctatgcca tgagctgggt ccgccaggct    120
ccagggaagg ggctggagtg ggtctcaggt attggttctt acggtggtgg tacatactat    180
gcagactccg tgaagggccg gttcaccatc tcccgtgaca attccaagaa cacgctgtat    240
ctgcaaatga acagcctgcg tgccgaggac acggctgtat attattgtgc gcgctacgtt    300
aacttcggta tggactattg gggccaggga accctggtca ccgtctcctc a             351
```

<210> SEQ ID NO 86
<211> LENGTH: 321
<212> TYPE: DNA
<213> ORGANISM: Homo sapiens

<400> SEQUENCE: 86

```
gacatccaga tgacccagtc tccatcctcc ctgagcgcat ctgtaggaga ccgcgtcacc     60
atcacttgcc gggcaagtca gagcattagc agctatttaa attggtatca gcagaaacca    120
gggaaagccc ctaagctcct gatctatgct gcatccagtt tgcaaagtgg ggtcccatca    180
cgtttcagtg gcagtggaag cgggacagat ttcactctca ccatcagcag tctgcaacct    240
gaagattttg caacttatta ctgtcaacag tacggtcgta acccgcccac ttttggccag    300
gggaccaagc tggagatcaa a                                              321
```

<210> SEQ ID NO 87
<211> LENGTH: 348
<212> TYPE: DNA
<213> ORGANISM: Homo sapiens

<400> SEQUENCE: 87

```
gaggtgcagc tgttggagag cggggggaggc ttggtacagc ctggggggtc cctgcgcctc    60
tcctgtgcag ccagcggatt cacctttagc agctatgcca tgagctgggt ccgccaggct    120
ccagggaagg ggctggagtg ggtctcagct attagtggta gtggtggtag cacatactat    180
gcagactccg tgaagggccg gttcaccatc tcccgtgaca attccaagaa cacgctgtat    240
ctgcaaatga acagcctgcg tgccgaggac acggctgtat attattgtgc gcgcgctgtt    300
ttcggttttg actattgggg ccagggaacc ctggtcaccg tctcctca                 348
```

<210> SEQ ID NO 88
<211> LENGTH: 321
<212> TYPE: DNA
<213> ORGANISM: Homo sapiens

<400> SEQUENCE: 88

```
gacatccaga tgacccagtc tccatcctcc ctgagcgcat ctgtaggaga ccgcgtcacc     60
atcacttgcc gggcaagtca gagcattagc agctatttaa attggtatca gcagaaacca    120
gggaaagccc ctaagctcct gatctatgct gcatccagtt tgcaaagtgg ggtcccatca    180
cgtttcagtg gcagtggaag cgggacagat ttcactctca ccatcagcag tctgcaacct    240
gaagattttg caacttatta ctgtcaacag gcttactact cccgcacac ttttggccag     300 gggaccaagc tggagatcaa a                                              321
```

<210> SEQ ID NO 89
<211> LENGTH: 357
<212> TYPE: DNA
<213> ORGANISM: Homo sapiens

<400> SEQUENCE: 89

```
gaggtgcagc tgttggagag cggggggaggc ttggtacagc ctggggggtc cctgcgcctc    60
```

```
tcctgtgcag ccagcggatt cacctttagc agctatgcca tgagctgggt ccgccaggct    120
ccagggaagg ggctggagtg ggtctcagct attagtggta gtggtggtag cacatactat    180
gcagactccg tgaagggccg gttcaccatc tcccgtgaca attccaagaa cacgctgtat    240
ctgcaaatga acagcctgcg tgccgaggac acggctgtat attattgtgc gcgcggtttc    300
gtttactctt cttacattga ctattggggc cagggaaccc tggtcaccgt ctcctca       357
```

<210> SEQ ID NO 90
<211> LENGTH: 321
<212> TYPE: DNA
<213> ORGANISM: Homo sapiens

<400> SEQUENCE: 90

```
gacatccaga tgacccagtc tccatcctcc ctgagcgcat ctgtaggaga ccgcgtcacc     60
atcacttgcc gggcaagtca gagcattagc agctatttaa attggtatca gcagaaacca    120
gggaaagccc ctaagctcct gatctatgct gcatccagtt tgcaaagtgg ggtcccatca    180
cgtttcagtg gcagtggaag cgggacagat ttcactctca ccatcagcag tctgcaacct    240
gaagattttg caacttatta ctgtcaacag agttacagta ccccttatac ttttggccag    300
gggaccaagc tggagatcaa a                                              321
```

<210> SEQ ID NO 91
<211> LENGTH: 357
<212> TYPE: DNA
<213> ORGANISM: Homo sapiens

<400> SEQUENCE: 91

```
gaggtgcagc tgttggagag cggggggaggc ttggtacagc ctgggggggtc cctgcgcctc     60 tcctgtgcag ccagcggatt cacctttagc agctatgcca tgagctgggt ccgccaggct    120
ccagggaagg ggctggagtg ggtctcatct atttactctg gtggtggtgg tacatcttat    180
gcagactccg tgaagggccg gttcaccatc tcccgtgaca attccaagaa cacgctgtat    240
ctgcaaatga acagcctgcg tgccgaggac acggctgtat attattgtgc gcgcggtccg    300
gcttactctt ctttctttga ctattggggc cagggaaccc tggtcaccgt ctcctca       357
```

<210> SEQ ID NO 92
<211> LENGTH: 321
<212> TYPE: DNA
<213> ORGANISM: Homo sapiens

<400> SEQUENCE: 92

```
gacatccaga tgacccagtc tccatcctcc ctgagcgcat ctgtaggaga ccgcgtcacc     60
atcacttgcc gggcaagtca gagcattagc agctatttaa attggtatca gcagaaacca    120
gggaaagccc ctaagctcct gatctatgct gcatccagtt tgcaaagtgg ggtcccatca    180
cgtttcagtg gcagtggaag cgggacagat ttcactctca ccatcagcag tctgcaacct    240
gaagattttg caacttatta ctgtcaacag agttacagta ccccttatac ttttggccag    300
gggaccaagc tggagatcaa a                                              321
```

<210> SEQ ID NO 93
<211> LENGTH: 348
<212> TYPE: DNA
<213> ORGANISM: Homo sapiens

<400> SEQUENCE: 93

```
gaggtgcagc tgttggagag cggggggaggc ttggtacagc ctggggggtc cctgcgcctc    60
tcctgtgcag ccagcggatt cacctttagc agctatgcca tgagctgggt ccgccaggct   120
ccagggaagg ggctggagtg ggtctcagct attagtggta gtggtggtag cacatactat   180
gcagactccg tgaagggccg gttcaccatc tcccgtgaca attccaagaa cacgctgtat   240
ctgcaaatga acagcctgcg tgccgaggac acggctgtat attattgtgc gcgctacgtt   300
ttcggtattg actattgggg ccagggaacc ctggtcaccg tctcctca               348
```

<210> SEQ ID NO 94
<211> LENGTH: 324
<212> TYPE: DNA
<213> ORGANISM: Homo sapiens

<400> SEQUENCE: 94

```
gacatccaga tgacccagtc tccatcctcc ctgagcgcat ctgtaggaga ccgcgtcacc    60
atcacttgcc gggcaagtca gagcattagc agctatttaa attggtatca gcagaaacca   120
gggaaagccc ctaagctcct gatctatgct gcatccagtt tgcaaagtgg ggtcccatca   180
cgtttcagtg gcagtggaag cgggacagat ttcactctca ccatcagcag tctgcaacct   240
gaagattttg caacttatta ctgtcaacag gcttactacg ctggtctgtt cacttttggc   300
caggggacca agctggagat aaaa                                           324
```

<210> SEQ ID NO 95
<211> LENGTH: 357
<212> TYPE: DNA
<213> ORGANISM: Homo sapiens

<400> SEQUENCE: 95

```
gaggtgcagc tgttggagag cggggggaggc ttggtacagc ctggggggtc cctgcgcctc    60
tcctgtgcag ccagcggatt cacctttagc agctatgcca tgagctgggt ccgccaggct   120
ccagggaagg ggctggagtg ggtctcagct attagtggta gtggtggtag cacatactat   180
gcagactccg tgaagggccg gttcaccatc tcccgtgaca attccaagaa cacgctgtat   240
ctgcaaatga acagcctgcg tgccgaggac acggctgtat attattgtgc gcgcggtccg   300
gtttactctt ctgttttga ctattggggc cagggaaccc tggtcaccgt ctcctca       357
```

<210> SEQ ID NO 96
<211> LENGTH: 321
<212> TYPE: DNA
<213> ORGANISM: Homo sapiens

<400> SEQUENCE: 96

```
gacatccaga tgacccagtc tccatcctcc ctgagcgcat ctgtaggaga ccgcgtcacc    60
atcacttgcc gggcaagtca gagcattagc agctatttaa attggtatca gcagaaacca   120
gggaaagccc ctaagctcct gatctatgct gcatccagtt tgcaaagtgg ggtcccatca   180
cgtttcagtg gcagtggaag cgggacagat ttcactctca ccatcagcag tctgcaacct   240
gaagattttg caacttatta ctgtcaacag agttacagta ccccttatac ttttggccag   300
gggaccaagc tggagatcaa a                                              321
```

<210> SEQ ID NO 97
<211> LENGTH: 351
<212> TYPE: DNA
<213> ORGANISM: Homo sapiens

<400> SEQUENCE: 97

```
gaggtgcagc tgttggagag cgggggaggc ttggtacagc ctgggggtc cctgcgcctc      60
tcctgtgcag ccagcggatt cacctttagc agctatgcca tgagctgggt ccgccaggct    120
ccagggaagg ggctggagtg ggtctcaggt attggtggtt cttcttctta cacatcttat    180
gcagactccg tgaagggccg gttcaccatc tcccgtgaca attccaagaa cacgctgtat    240
ctgcaaatga acagcctgcg tgccgaggac acggctgtat attattgtgc gcgctactac    300
tcttaccata tggactattg gggccaggga accctggtca ccgtctcctc a             351
```

<210> SEQ ID NO 98
<211> LENGTH: 321
<212> TYPE: DNA
<213> ORGANISM: Homo sapiens

<400> SEQUENCE: 98

```
gacatccaga tgacccagtc tccatcctcc ctgagcgcat ctgtaggaga ccacgtcacc     60
atcacttgcc gggcaagtca gagcattagc agctatttaa attggtatca gcagaaacca   120
gggaaagccc ctaagctcct gatctatgct gcatccagtt tgcaaagtgg ggtcccatca   180
cgtttcagtg gcagtggaag cgggacagat ttcactctca ccatcagcag tctgcaacct   240
gaagattttg caacttatta ctgtcaacag tacggttctg ctccgcccac ttttggccag   300
gggaccaagc tggagatcaa a                                             321
```

<210> SEQ ID NO 99
<211> LENGTH: 350
<212> TYPE: DNA
<213> ORGANISM: Homo sapiens

<400> SEQUENCE: 99

```
gaggtgcagc tgttggagag cgggggaggc ttggtacagc ctgggggtc cctgcgcctc      60
tcctgtgcag ccagcggatt cacctttagc agctatgcca tgagctgggt ccgccaggct   120
ccagggaagg ggctggagtg ggtctcagct attagtggta gtggtggtag cacatactat   180
gcagactccg tgaagggccg gttcaccatc tcccgtgaca attccaagaa cacgctgtat   240
ctgcaaatga acagcctgcg tgccgaggac acggctgtat attattgtgc gcgccgtgtt   300
tggggttttg actattgggg ccagggaacc ctggtcaccg tctcctcagg              350
```

<210> SEQ ID NO 100
<211> LENGTH: 321
<212> TYPE: DNA
<213> ORGANISM: Homo sapiens

<400> SEQUENCE: 100

```
gacatccaga tgacccagtc tccatcctcc ctgagcgcat ctgtaggaga ccgcgtcacc     60
atcacttgcc gggcaagtca gagcattagc agctatttaa attggtatca gcagaaacca   120
gggaaagccc ctaagctcct gatctatgct gcatccagtt tgcaaagtgg ggtcccatca   180
cgtttcagtg gcagtggaag cgggacagat ttcactctca ccatcagcag tctgcaacct   240
gaagattttg caacttatta ctgtcaacag tacggtgttt acccgttcac ttttggccag   300
gggaccaagc tggagatcaa a                                             321
```

<210> SEQ ID NO 101
<211> LENGTH: 326
<212> TYPE: PRT
<213> ORGANISM: Homo sapiens

<400> SEQUENCE: 101

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
130                 135                 140

Val Ser Gln Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Gly Leu Pro
        195                 200                 205

Ser Ser Ile Glu Lys Thr Ile Ser Lys Ala Lys Gly Gln Pro Arg Glu
210                 215                 220

Pro Gln Val Tyr Thr Leu Pro Pro Ser Gln Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Arg
        275                 280                 285

Leu Thr Val Asp Lys Ser Arg Trp Gln Glu Gly Asn Val Phe Ser Cys
290                 295                 300

Ser Val Met His Glu Ala Leu His Asn His Tyr Thr Gln Lys Ser Leu
305                 310                 315                 320

Ser Leu Ser Leu Gly Lys
                325

<210> SEQ ID NO 102
<211> LENGTH: 330
<212> TYPE: PRT
<213> ORGANISM: Homo sapiens

<400> SEQUENCE: 102

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

```
Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 103
<211> LENGTH: 106
<212> TYPE: PRT
<213> ORGANISM: Homo sapiens

<400> SEQUENCE: 103

Thr Val Ala Ala Pro Ser Val Phe Ile Phe Pro Pro Ser Asp Glu Gln
  1               5                  10                  15

Leu Lys Ser Gly Thr Ala Ser Val Val Cys Leu Leu Asn Asn Phe Tyr
             20                  25                  30

Pro Arg Glu Ala Lys Val Gln Trp Lys Val Asp Asn Ala Leu Gln Ser
         35                  40                  45

Gly Asn Ser Gln Glu Ser Val Thr Glu Gln Asp Ser Lys Asp Ser Thr
 50                  55                  60

Tyr Ser Leu Ser Ser Thr Leu Thr Leu Ser Lys Ala Asp Tyr Glu Lys
 65                  70                  75                  80
```

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 104
<211> LENGTH: 277
<212> TYPE: PRT
<213> ORGANISM: Homo sapiens

<400> SEQUENCE: 104

Met Val Arg Leu Pro Leu Gln Cys Val Leu Trp Gly Cys Leu Leu Thr
1               5                   10                  15

Ala Val His Pro Glu Pro Pro Thr Ala Cys Arg Glu Lys Gln Tyr Leu
            20                  25                  30

Ile Asn Ser Gln Cys Cys Ser Leu Cys Gln Pro Gly Gln Lys Leu Val
        35                  40                  45

Ser Asp Cys Thr Glu Phe Thr Glu Thr Glu Cys Leu Pro Cys Gly Glu
    50                  55                  60

Ser Glu Phe Leu Asp Thr Trp Asn Arg Glu Thr His Cys His Gln His
65                  70                  75                  80

Lys Tyr Cys Asp Pro Asn Leu Gly Leu Arg Val Gln Gln Lys Gly Thr
                85                  90                  95

Ser Glu Thr Asp Thr Ile Cys Thr Cys Glu Glu Gly Trp His Cys Thr
            100                 105                 110

Ser Glu Ala Cys Glu Ser Cys Val Leu His Arg Ser Cys Ser Pro Gly
        115                 120                 125

Phe Gly Val Lys Gln Ile Ala Thr Gly Val Ser Asp Thr Ile Cys Glu
    130                 135                 140

Pro Cys Pro Val Gly Phe Phe Ser Asn Val Ser Ser Ala Phe Glu Lys
145                 150                 155                 160

Cys His Pro Trp Thr Ser Cys Glu Thr Lys Asp Leu Val Val Gln Gln
                165                 170                 175

Ala Gly Thr Asn Lys Thr Asp Val Val Cys Gly Pro Gln Asp Arg Leu
            180                 185                 190

Arg Ala Leu Val Val Ile Pro Ile Ile Phe Gly Ile Leu Phe Ala Ile
        195                 200                 205

Leu Leu Val Leu Val Phe Ile Lys Lys Val Ala Lys Lys Pro Thr Asn
    210                 215                 220

Lys Ala Pro His Pro Lys Gln Glu Pro Gln Glu Ile Asn Phe Pro Asp
225                 230                 235                 240

Asp Leu Pro Gly Ser Asn Thr Ala Ala Pro Val Gln Glu Thr Leu His
                245                 250                 255

Gly Cys Gln Pro Val Thr Gln Glu Asp Gly Lys Glu Ser Arg Ile Ser
            260                 265                 270

Val Gln Glu Arg Gln
        275

<210> SEQ ID NO 105
<211> LENGTH: 111
<212> TYPE: PRT
<213> ORGANISM: Homo sapiens

<400> SEQUENCE: 105

Ala Pro Leu Lys Ile Gln Ala Tyr Phe Asn Glu Thr Ala Asp Leu Pro
1               5                   10                  15

Cys Gln Phe Ala Asn Ser Gln Asn Gln Ser Leu Ser Glu Leu Val Val
                20                  25                  30

Phe Trp Gln Asp Gln Glu Asn Leu Val Leu Asn Glu Val Tyr Leu Gly
            35                  40                  45

Lys Glu Lys Phe Asp Ser Val His Ser Lys Tyr Met Gly Arg Thr Ser
    50                  55                  60

Phe Asp Ser Asp Ser Trp Thr Leu Arg Leu His Asn Leu Gln Ile Lys
65                  70                  75                  80

Asp Lys Gly Leu Tyr Gln Cys Ile Ile His His Lys Lys Pro Thr Gly
                85                  90                  95

Met Ile Arg Ile His Gln Met Asn Ser Glu Leu Ser Val Leu Ala
                100                 105                 110

<210> SEQ ID NO 106
<211> LENGTH: 109
<212> TYPE: PRT
<213> ORGANISM: Artificial Sequence
<220> FEATURE:
<223> OTHER INFORMATION: Sequence of CTLA-4 binding clone number 904

<400> SEQUENCE: 106

Leu Lys Ile Gln Ala Tyr Phe Asn Glu Thr Ala Asp Leu Pro Cys Gln
1               5                   10                  15

Phe Ala Asn Ser Gln Asn Gln Ser Leu Ser Glu Leu Ile Val Phe Trp
                20                  25                  30

Gln Asp Gln Glu Asn Leu Val Leu Asn Glu Val Tyr Leu Gly Lys Glu
            35                  40                  45

Arg Phe Asp Ala Val Asp Ser Lys Tyr Met Gly Arg Thr Ser Phe Asp
    50                  55                  60

Ser Asp Ser Trp Thr Leu Arg Leu His Asn Leu Gln Ile Lys Asp Lys
65                  70                  75                  80

Gly Ile Tyr Gln Cys Ile Ile His His Lys Lys Pro Ser Gly Met Val
                85                  90                  95

Lys Ile His Gln Met Asp Ser Glu Leu Ser Val Leu Ala
                100                 105

<210> SEQ ID NO 107
<211> LENGTH: 111
<212> TYPE: PRT
<213> ORGANISM: Artificial Sequence
<220> FEATURE:
<223> OTHER INFORMATION: Sequence of CTLA-4 binding clone number 1040

<400> SEQUENCE: 107

Ala Pro Leu Lys Ile Gln Ala Tyr Phe Asn Glu Thr Ala Asp Leu Pro
1               5                   10                  15

Cys Gln Phe Ala Asn Ser Gln Asn Leu Ser Leu Ser Glu Leu Val Val
                20                  25                  30

Phe Trp Gln Asp Gln Glu Asn Leu Val Leu Asn Glu Val Tyr Leu Gly
            35                  40                  45

Lys Glu Arg Phe Asp Ser Val Asp Ser Lys Tyr Met Gly Arg Thr Ser
    50                  55                  60

Phe Asp Ser Asp Ser Trp Thr Leu Arg Leu His Asn Leu Gln Ile Lys
65                  70                  75                  80

Asp Lys Gly Arg Tyr Gln Cys Ile Ile His His Lys Lys Pro Thr Gly
                85                  90                  95

Met Ile Asn Ile His Gln Met Asn Ser Glu Leu Ser Val Leu Ala

-continued

```
                100                 105                 110
```

<210> SEQ ID NO 108
<211> LENGTH: 111
<212> TYPE: PRT
<213> ORGANISM: Artificial Sequence
<220> FEATURE:
<223> OTHER INFORMATION: Sequence of CTLA-4 binding clone number 1044

<400> SEQUENCE: 108

```
Ala Pro Leu Lys Ile Gln Ala Tyr Phe Asn Glu Thr Ala Asp Leu Pro
1               5                   10                  15

Cys Gln Phe Ala Asn Ser Gln Asn Leu Thr Leu Ser Glu Leu Val Val
            20                  25                  30

Phe Trp Gln Asp Gln Glu Asn Leu Val Leu Asn Glu Val Tyr Leu Gly
        35                  40                  45

Lys Glu Lys Phe Asp Ser Val Ser Ser Lys Tyr Met Gly Arg Thr Ser
    50                  55                  60

Phe Asp Ser Asp Ser Trp Thr Leu Arg Leu His Asn Leu Gln Ile Lys
65                  70                  75                  80

Asp Lys Gly Ile Tyr Gln Cys Ile Ile His His Lys Lys Pro Thr Gly
                85                  90                  95

Met Ile Lys Ile His Glu Met Ser Ser Glu Leu Ser Val Leu Ala
                100                 105                 110
```

<210> SEQ ID NO 109
<211> LENGTH: 12
<212> TYPE: PRT
<213> ORGANISM: Artificial Sequence
<220> FEATURE:
<223> OTHER INFORMATION: heavy chain CDR3 consensus sequence
<220> FEATURE:
<221> NAME/KEY: VARIANT
<222> LOCATION: 5
<223> OTHER INFORMATION: Xaa is Phe, Val, or Ala
<220> FEATURE:
<221> NAME/KEY: VARIANT
<222> LOCATION: 8
<223> OTHER INFORMATION: Xaa is Ser or Thr
<220> FEATURE:
<221> NAME/KEY: VARIANT
<222> LOCATION: 9
<223> OTHER INFORMATION: Xaa is Val, Tyr, or Phe
<220> FEATURE:
<221> NAME/KEY: VARIANT
<222> LOCATION: 10
<223> OTHER INFORMATION: Xaa is Phe, Ile, or Leu

<400> SEQUENCE: 109

```
Ala Arg Gly Pro Xaa Tyr Ser Xaa Xaa Xaa Asp Tyr
1               5                   10
```

<210> SEQ ID NO 110
<211> LENGTH: 10
<212> TYPE: PRT
<213> ORGANISM: Artificial Sequence
<220> FEATURE:
<223> OTHER INFORMATION: heavy chain CDR3 consensus sequence
<220> FEATURE:
<221> NAME/KEY: VARIANT
<222> LOCATION: 3
<223> OTHER INFORMATION: Xaa is Ala, Tyr, or Arg
<220> FEATURE:
<221> NAME/KEY: VARIANT
<222> LOCATION: 5
<223> OTHER INFORMATION: Xaa is absent or Asn
<220> FEATURE:
<221> NAME/KEY: VARIANT

```
<222> LOCATION: 8
<223> OTHER INFORMATION: Xaa is Phe, Met, or Ile

<400> SEQUENCE: 110

Ala Arg Xaa Val Xaa Phe Gly Xaa Asp Tyr
1               5                   10

<210> SEQ ID NO 111
<211> LENGTH: 22
<212> TYPE: PRT
<213> ORGANISM: Homo sapiens

<400> SEQUENCE: 111

Cys Ser Leu Cys Gln Pro Gly Gln Lys Leu Val Ser Asp Cys Thr Glu
1               5                   10                  15

Phe Thr Glu Thr Glu Cys
            20

<210> SEQ ID NO 112
<211> LENGTH: 22
<212> TYPE: PRT
<213> ORGANISM: Mus musculus

<400> SEQUENCE: 112

Cys Asp Leu Cys Gln Pro Gly Ser Arg Leu Thr Ser His Cys Thr Ala
1               5                   10                  15

Leu Glu Lys Thr Gln Cys
            20

<210> SEQ ID NO 113
<211> LENGTH: 16
<212> TYPE: PRT
<213> ORGANISM: Homo sapiens

<400> SEQUENCE: 113

Cys Gly Glu Ser Glu Phe Leu Asp Thr Trp Asn Arg Glu Thr His Cys
1               5                   10                  15

<210> SEQ ID NO 114
<211> LENGTH: 16
<212> TYPE: PRT
<213> ORGANISM: Mus musculus

<400> SEQUENCE: 114

Cys Asp Ser Gly Glu Phe Ser Ala Gln Trp Asn Arg Glu Ile Arg Cys
1               5                   10                  15

<210> SEQ ID NO 115
<211> LENGTH: 22
<212> TYPE: PRT
<213> ORGANISM: Homo sapiens

<400> SEQUENCE: 115

His Arg Ser Cys Ser Pro Gly Phe Gly Val Lys Gln Ile Ala Thr Gly
1               5                   10                  15

Val Ser Asp Thr Ile Cys
            20

<210> SEQ ID NO 116
<211> LENGTH: 22
<212> TYPE: PRT
<213> ORGANISM: Mus musculus

<400> SEQUENCE: 116
```

```
His Thr Pro Cys Ile Pro Gly Phe Gly Val Met Glu Met Ala Thr Glu
1               5                   10                  15
Thr Thr Asp Thr Val Cys
            20
```